United States Patent
Gandhi et al.

(10) Patent No.: US 9,694,015 B2
(45) Date of Patent: Jul. 4, 2017

(54) METHODS FOR THE TREATMENT OF LOCALLY ADVANCED BREAST CANCER

(71) Applicant: Celgene Corporation, Summit, NJ (US)

(72) Inventors: Anita Gandhi, Bernardsville, NJ (US); Jorge Dimartino, Belmont, NJ (US); Rajesh Chopra, Summit, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/426,114

(22) PCT Filed: Sep. 9, 2013

(86) PCT No.: PCT/US2013/058744
§ 371 (c)(1),
(2) Date: Mar. 4, 2015

(87) PCT Pub. No.: WO2014/039960
PCT Pub. Date: Mar. 13, 2014

(65) Prior Publication Data
US 2015/0224104 A1    Aug. 13, 2015

Related U.S. Application Data

(60) Provisional application No. 61/699,170, filed on Sep. 10, 2012.

(51) Int. Cl.
| | | |
|---|---|---|
| *A61K 31/5377* | (2006.01) | |
| *A61K 45/06* | (2006.01) | |
| *A61K 31/445* | (2006.01) | |
| *A61K 31/454* | (2006.01) | |
| *A61K 31/517* | (2006.01) | |
| *G01N 33/574* | (2006.01) | |

(52) U.S. Cl.
CPC ........ *A61K 31/5377* (2013.01); *A61K 31/445* (2013.01); *A61K 31/454* (2013.01); *A61K 31/517* (2013.01); *A61K 45/06* (2013.01); *G01N 33/57415* (2013.01); *G01N 2333/4703* (2013.01)

(58) Field of Classification Search
CPC ............................ A61K 31/5377; A61K 31/454
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,810,643 A | 3/1989 | Souza | |
| 4,999,291 A | 3/1991 | Souza | |
| 5,059,595 A | 10/1991 | Le Grazie | |
| 5,073,543 A | 12/1991 | Marshall et al. | |
| 5,120,548 A | 6/1992 | McClelland et al. | |
| 5,134,127 A | 7/1992 | Stella et al. | |
| 5,229,496 A | 7/1993 | Deeley et al. | |
| 5,354,556 A | 10/1994 | Sparks et al. | |
| 5,391,485 A | 2/1995 | Deeley et al. | |
| 5,393,870 A | 2/1995 | Deeley et al. | |
| 5,580,755 A | 12/1996 | Souza | |
| 5,582,823 A | 12/1996 | Souza | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,281,230 B1 | 8/2001 | Muller et al. | |
| 6,316,471 B1 | 11/2001 | Muller et al. | |
| 6,395,754 B1 | 5/2002 | Muller et al. | |
| 6,555,554 B2 | 4/2003 | Muller et al. | |
| 7,091,353 B2 | 8/2006 | Robarge et al. | |
| 7,635,700 B2 * | 12/2009 | Muller ................. | C07D 401/14 514/266.22 |
| 7,709,502 B2 | 5/2010 | Muller et al. | |
| 7,812,169 B2 | 10/2010 | Treston et al. | |
| 8,802,685 B2 | 8/2014 | Muller et al. | |
| 8,906,932 B2 * | 12/2014 | Muller ................... | A61K 45/06 514/266.22 |
| 2004/0029832 A1 | 2/2004 | Zeldis | |
| 2011/0196150 A1 | 8/2011 | Man et al. | |
| 2014/0045843 A1 | 2/2014 | Schafer et al. | |
| 2014/0162282 A1 | 6/2014 | Schafer et al. | |

FOREIGN PATENT DOCUMENTS

| | | |
|---|---|---|
| WO | WO 98/54170 A1 | 3/1998 |
| WO | 2012/125459 A1 | 9/2012 |
| WO | 2012/149299 A2 | 11/2012 |

(Continued)

OTHER PUBLICATIONS

Vippagunta et al (2001).*
Wolff et al. (1976).*
U.S. Appl. No. 14/552,337, (filed Nov. 24, 2014).*
Burris et al., "Phase II study of capecitabine in combination with thalidomide in patients with metastatic breast cancer," Cancer Invest., 28:408-412 (2010).
Zhu et al., "Cereblon expression is required for the antimyeloma activity of lenalidomide and pomalidomide," Blood, 118(18):4771-4779 (2011).

(Continued)

*Primary Examiner* — Paul V Ward
(74) *Attorney, Agent, or Firm* — Jones Day

(57) ABSTRACT

Provided herein are methods of treating, preventing and/or managing locally advanced breast cancer, including inflammatory breast cancer, which comprise administering to a patient one or more immunomodulatory compounds or enantiomers or mixtures of enantiomers thereof, or pharmaceutically acceptable salts, solvates, hydrates, co-crystals, clathrates, or polymorphs thereof.

17 Claims, 18 Drawing Sheets

(56) References Cited

FOREIGN PATENT DOCUMENTS

WO    WO 2014/025960 A1    2/2014

OTHER PUBLICATIONS

Boehm et al., "Integrative genomic approaches identify IKBKE as a breast cancer oncogene," *Cell*, 129(6):1065-1079 (2007).
Brito et al., "Expression of Hypoxia-inducible factor 1-α and vascular endothelial growth factor-C in locally advanced breast cancer patients," *Clinics (Sao Paulo)*, 66(8):1313-1320 (2011).
Cairns et al., "Regulation of cancer cell metabolism," *Nature Rev.*, 11:85-95 (2011).
Carstensen, *Drug Stability: Principles & Practices*, Second Edition, Marcel Dekker, New York, NY, pp. 379-380 (1995).
Emens et al., "Chemotherapy: friend of foe to cancer vaccines," Curr. Opin. Mol. Ther., 3(1):77-84 (2001).
Kuo, "TNFα induces HIF-1alpha expression through activation of IKKbeta," *Biochem. Biophys. Res. Commun.*, 389(4):640-644 (2009).
Li et al., "Trimodal therapy for inflammatory breast cancer: a surgeon's perspective," *Oncology*, 79(1-2):3-12 (2010).
Mardis et al., "Recurring mutations found by sequencing an acute myeloid leukemia genome," *N. Engl. J. Med.*, 361(11):1058-1066 (2009).
National Cancer Institute, Fact Sheet on Inflammatory Breast Cancer, [retrieved on Mar. 22, 2016]. Retrieved from the internet <http://www.cancer.gov/cancertopics/factsheet/Sites-types/IBC>, 5 pages.
Parsons et al., "An integrated genomic analysis of human glioblastoma multiforme," *Science*, 321:1807-1812 (2008).
Penichet et al., "Antibody-cytokine fusion proteins for the therapy of cancer," *J. Immunol. Methods*, 284:91-101 (2001).
Roitt et al., *Immunology*, Third Edition, Mosby, St. Louis, MO, 17.1-17.12 (1993).
Shackelford et al., "The LKB1-AMPK pathway: metabolism and growth control in tumour suppression," *Nature Rev.*, 9:563-575 (2009).
Stockdale, *Medicine*, vol. 3, Rubenstein and Federman, eds., Chapter 12, Section IV and Section X (1998).
Therasse et al., "New guidelines to evaluate the response to treatment in solid tumors," *J. Natl. Cancer Inst.*, 92(3):205-216 (2000).
Wolff ed., *Burger's Medicinal Chemistry and Drug Discovery*, $5^{th}$ Edition, John Wiley & Sons, Inc., pp. 172-178, 949-982 (1995).

* cited by examiner

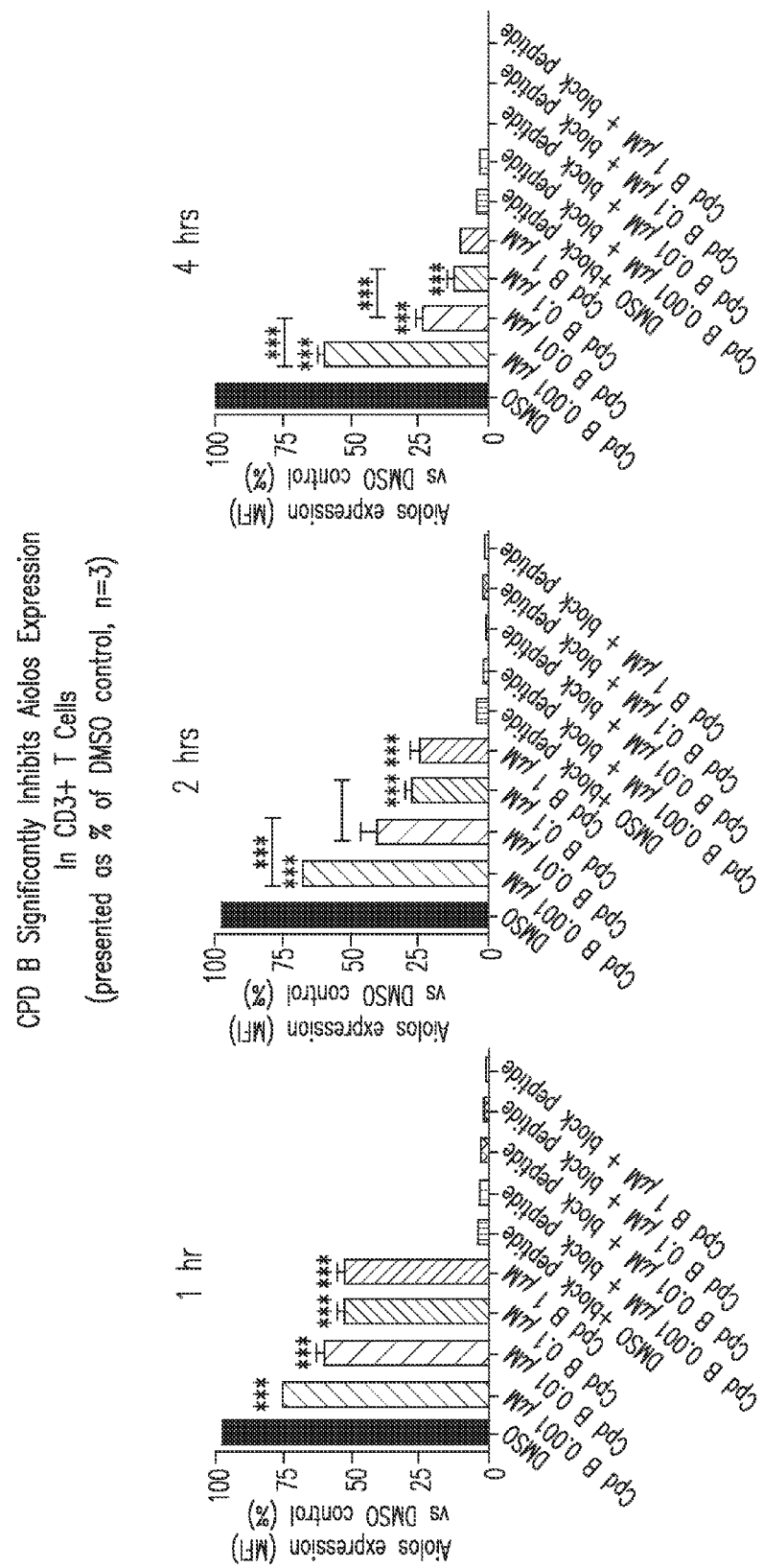

(AUC $_{24hr}$)=area under the curve from 0 to 34 hr; HNSTD=highest non-serverely toxic dose; HED=human equivalent dose; STD10=severely toxic dose in 10% of the animal.

[a] Day 23 (monkey) or Day 28 (rat) AUG$_{24hr}$ values from 28-day toxicity studies using sex with lowest AUC.

[b] Human AUC values are predicted based on allometric scaling.

[c] AUC values for in vitro data were calculated as IC50* 24 hours.

METHODS FOR THE TREATMENT OF LOCALLY ADVANCED BREAST CANCER

The present application is a 371 of International Application No. PCT/US2013/058744, filed Sep. 9, 2013, which claims priority to U.S. Provisional Patent Application No. 61/699,170, filed Sep. 10, 2012, the entirety of each of which is incorporated herein by reference.

1. FIELD

Provided herein are methods of treating, preventing and/or managing locally advanced breast cancer, including inflammatory breast cancer, which comprise administering to a patient one or more immunomodulatory compounds or enantiomers or mixtures of enantiomers thereof, or pharmaceutically acceptable salts, solvates, hydrates, co-crystals, clathrates, or polymorphs thereof.

2. BACKGROUND

2.1 Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J. and Kale, D., *Immunology*, 17.1-17.12 (3rd ed., Mosby, St. Louis, Mo., 1993).

There is an enormous variety of cancers which are described in detail in the medical literature. Examples include cancer of the breast, lung, colon, rectum, prostate, brain, and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and tumor necrosis factor alpha (TNF-α). Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

Pathobiology of Tumors

Solid tumors are abnormal masses of tissue that may, but usually do not contain cysts or liquid areas. Solid tumors may be benign (not cancer), or malignant (cancer). Different types of solid tumors are named for the type of cells that form them. Examples of types solid tumors include, but are not limited to malignant melanoma, adrenal carcinoma, breast carcinoma, renal cell cancer, carcinoma of the pancreas, non-small-cell lung carcinoma (NSCLC) and carcinoma of unknown primary.

Additionally, the link between cancer and altered cellular metabolism has been well established. See Cairns, R. A., et al. *Nature Rev.*, 2011, 11:85-95. Understanding tumor cell metabolism and the associated genetic changes thereof may lead to the identification of improved methods of cancer treatment. Id. For example, tumor cell survival and proliferation via increased glucose metabolism has been linked to the PIK3 pathway, whereby mutations in tumor suppressor genes such as PTEN activate tumor cell metabolism. Id. AKT1 (a.k.a., PKB) stimulates glucose metabolism associated with tumor cell growth by various interactions with PFKFB3, ENTPD5, mTOR and TSC2 (a.k.a., tuberin). Id.

Transcription factors HIF1 and HIF2 are largely responsible for cellular response to low oxygen conditions often associated with tumors. Id. Once activated, HIF1 promotes tumor cell capacity to carry out glycolysis. Id. Thus, inhibition of HIF1 may slow or reverse tumor cell metabolism. Activation of HIF1 has been linked to PI3K, tumor suppressor proteins such as VHL, succinate dehydrogenase (SDH) and fumarate hydratase. Id. HIF1 is also regulated by various inflammatory mediators, including TNF-α in various breast cancer cell lines. Kuo, H.-P. *BBRC* 2009, 389, 640. The oncogenic transcription factor MYC has also been linked to tumor cell metabolism, specifically glycolysis. Cairns. MYC also promotes cell proliferation by glutamine metabolic pathways. Id.

AMP-activated protein kinase (AMPK) functions as a metabolic check point which tumor cells must overcome in order to proliferate. Id. Several mutations have been identified which suppress AMPK signaling in tumor cells. See Shackelford, D. B. & Shaw, R. J., *Nature Rev. Cancer*, 2009, 9: 563-575. STK11 has been identified as a tumor suppressor gene related to the role of AMPK. See Cairns, R. A., et al. *Nature Rev.*, 2011, 11:85-95.

The transcription factor p53, a tumor suppressor, also has an important role in the regulation of cellular metabolism. Id. The loss of p53 in tumor cells may be a significant contributor to changes in tumor cell metabolism to the glycolytic pathway. Id. The OCT1 transcription factor, another potential target for chemotherapeutics, may cooperate with p53 in regulating tumor cell metabolism. Id.

Pyruvate kinate M2 (PKM2) promotes changes in cellular metabolism which confer metabolic advantages to cancer cells by supporting cell proliferation. Id. For example, lung cancer cells which express PKM2 over PKM1 have been found to have such an advantage. Id. In the clinic, PKM2 has been identified as being overexpressed in a number of cancer types. Id. Thus PKM2 may be a useful biomarker for the early detection of tumors.

Mutations in isocitrate dehydrogenases IDH1 and IDH2 have been linked to tumorigenesis, specifically, in glioblastoma and acute myeloid leukemia. See Mardis, E. R. et al., *N. Engl. J. Med.*, 2009, 361: 1058-1066; Parsons, D. W. et al., *Science*, 2008, 321: 1807-1812.

The incidence of cancer continues to climb as the general population ages, as new cancers develop, and as susceptible populations (e.g., people infected with AIDS, the elderly or excessively exposed to sunlight) grow. A tremendous demand therefore exists for new methods, treatments and compositions that can be used to treat patients with cancer including breast cancer.

Breast Cancer

Breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer, is the most common type of cancer experienced by women worldwide, accounting for approximately 23% of cancers experienced by women, and approximately 14% of all cancer-related deaths of women. (World cancer report-2008) The most common form of breast cancer originates in the lactiferous ducts, and other forms develop in the lobules or in other breast tissue. The different forms of breast cancer show different rates of tumor growth, and have disparate survival rates, depending on a variety of factors.

Locally advanced breast cancer accounts for approximately 10% of all diagnosed breast cancers. See Brito, L. G. O., *Clinical Science* 2011, 66, 1313. This form of breast cancer has a greater risk of metastasis and a worse long-term prognosis compared to most breast cancers. Though rare, the most metastatic variant of locally advanced breast cancer, inflammatory breast cancer (IBC), poses many unique challenges to treatment. IBC is an aggressive form of breast cancer, which is difficult to diagnose as it does not typically present as a lump which can be detected during a physical exam or a mammogram, and also due to ambiguous symptoms which can lead to a misdiagnosis. Additionally, the duel factors of a younger patent population combined with a quickly developing cancer can lead to patients with advanced stages of the disease at the time of diagnosis. These problems are reflected in the 5-year relative survival of breast cancer patients; women diagnosed with IBC have a 5-year survival of 34%, compared to the 87% 5-year survival rate of patients with other stages of invasive breast cancers. See National Cancer Institute Fact Sheet on Inflammatory Breast Cancer (http://www.cancer.gov/cancertopics/factsheet/Sites-Types/IBC).

Treatment for locally advanced breast cancer and inflammatory breast cancer usually follows a multimodal approach, which involves 1) chemotherapy to reduce the physical size of the tumor, followed by 2) surgery to remove the tumor, then 3) radiation therapy. The chemotherapy portion of treatment usually involves multiple cycles of antieoplastic drug(s) over the course of several months before any attempt to surgically remove the tumor is elected. The choice of therapeutic agents can be determined by targeted therapy, which studies have shown leads to better responses to treatment and better survival rates. See Li, B. D. et al. *Oncology* 2010, 79, 3)

The incidence of breast cancer continues to climb as the general population ages, and as susceptible populations (e.g., the nulliparous and obese) increase in number. A tremendous demand therefore exists for new methods, treatments and compositions that can be used to treat patients with locally advanced breast cancer, including inflammatory breast cancer.

Accordingly, compounds that can control and/or inhibit unwanted angiogenesis or inhibit the production of certain cytokines, including TNF-α, may be useful in the treatment and prevention of locally advanced breast cancer, including inflammatory breast cancer.

2.2 Methods of Treating Cancer

Current cancer therapy may involve surgery, chemotherapy, hormonal therapy and/or radiation treatment to eradicate neoplastic cells in a patient (see, for example, Stockdale, 1998, *Medicine*, vol. 3, Rubenstein and Federman, Eds., Chapter 12, Section IV). Recently, cancer therapy could also involve biological therapy or immunotherapy. All of these approaches may pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Certain biological and other therapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A number of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, Eds., Ch. 12, sect. 10, 1998. Almost all chemotherapeutic agents are toxic, and chemotherapy causes significant and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as multidrug resistance. Because of the drug resistance, many cancers prove refractory to standard chemotherapeutic treatment protocols.

There exists a significant need for safe and effective methods of treating, preventing and managing cancer, particularly for cancers that are refractory to standard treatments, such as surgery, radiation therapy, chemotherapy and hormonal therapy, while reducing or avoiding the toxicities and/or side effects associated with the conventional therapies.

3. SUMMARY OF THE INVENTION

Provided herein are methods of treating, preventing, and/or managing breast cancer, including locally advanced and inflammatory breast cancer, as well as breast cancer that is refractory or resistant to conventional chemotherapy, which comprise administering to a patient in need of such treatment or prevention a therapeutically or prophylactically effective amount of an immunomodulatory compound.

In some embodiments, the immunomodulatory compound is selected from the group consisting of lenalidomide, pomalidomide, thalidomide, 3-(5-amino-2-methyl-4-oxo-4H-quinazolin-3-yl)-piperidine-2,6-dione, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-di-hydro-isoindol-2-yl)-piperidine-2,6-dione, and combinations thereof, or enantiomers or a mixture of enantiomers thereof, or pharmaceutically acceptable salts, solvates, hydrates, co-crystals, clathrates, or polymorphs thereof as a single agent or as a part of a combination therapy.

Also provided herein are methods of managing breast cancer (e.g., preventing its recurrence, or lengthening the time of remission), which comprise administering to a patient in need of such management a therapeutically effective amount of a compound described herein, combinations thereof, or enantiomers or mixtures of enantiomers thereof, or pharmaceutically acceptable salts, solvates, hydrates, co-crystals, clathrates, or polymorphs thereof.

Further provided herein are methods of treating, preventing, or managing breast cancer, comprising administering to a patient in need of such treatment, prevention, or management a therapeutically or prophylactically effective amount of the compounds provided herein, or enantiomers or mixtures of enantiomers thereof, or pharmaceutically acceptable salts, solvates, hydrates, co-crystals, clathrates, or polymorphs thereof; in combination with a therapy conventionally used to treat, prevent, or manage breast cancer. Examples of such conventional therapies include, but are not limited to, surgery, chemotherapy, radiation therapy, hormonal therapy, biological therapy, and immunotherapy.

Further provided herein are kits which, comprise a dosage form of a compound provided herein, or enantiomers or mixtures of enantiomers thereof, or pharmaceutically acceptable salts, solvates, hydrates, co-crystals, clathrates, or polymorphs thereof. In certain embodiments, the kit provided herein further comprises additional active agents, or a pharmacologically active mutant or derivative thereof, or a combination thereof. In certain embodiments, the kit provided herein further comprises a device that is used to administer the active ingredients. Examples of such devices include, but are not limited to, syringes, drip bags, patches, and inhalers.

4. BRIEF DESCRIPTION OF THE FIGURES

5. DETAILED DESCRIPTION OF THE INVENTION

Figure 1:
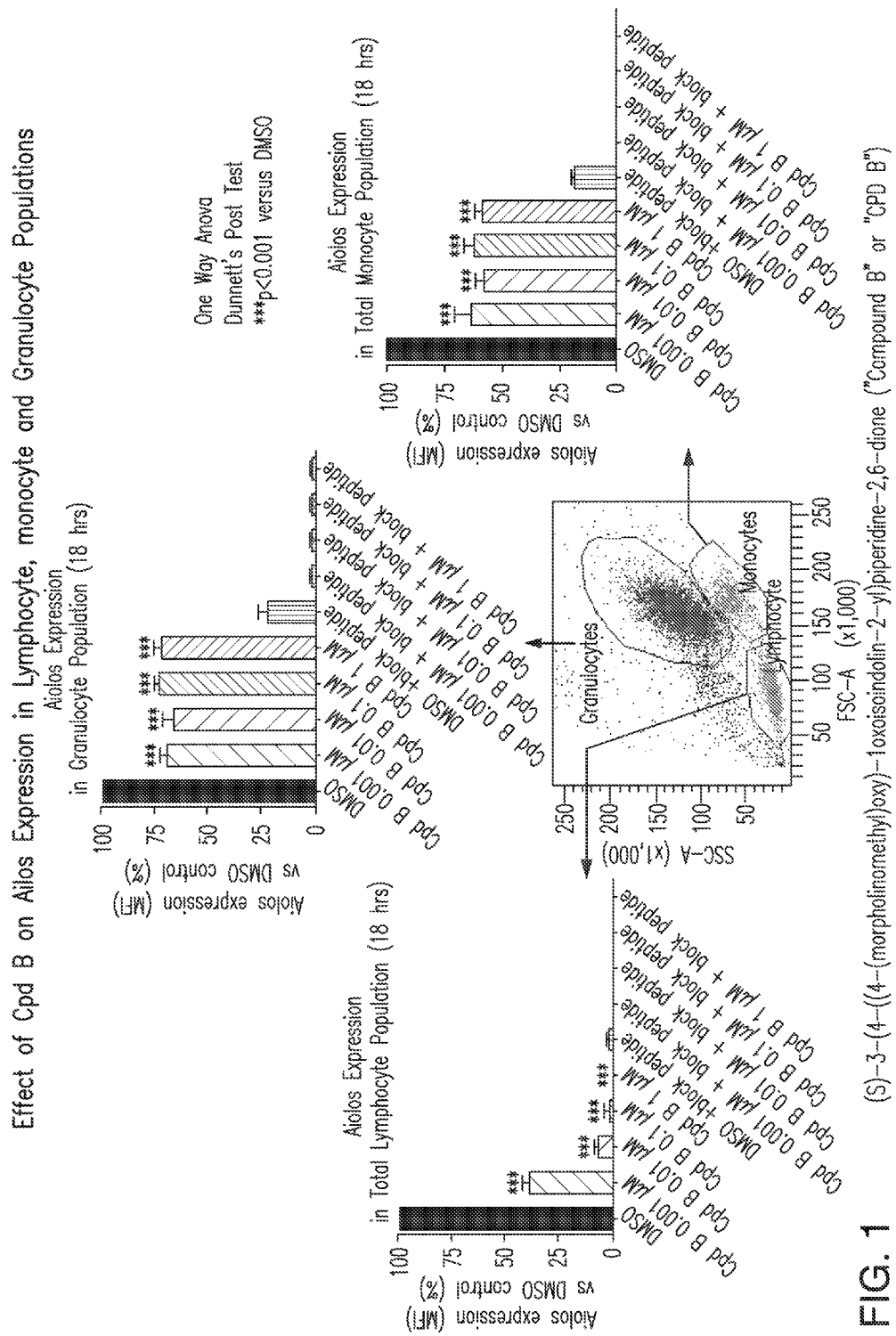
FIG. 1 illustrates the effect of (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione ("Compound B" or "CPD B") on inhibition of Aiolos expression in cell populations.

Provided herein are methods of treating, preventing, and/or managing breast cancer, including locally advanced and inflammatory breast cancer, as well as breast cancer that is refractory or resistant to conventional chemotherapy, which comprise administering to a patient in need of such treatment or prevention a therapeutically or prophylactically effective amount of an immunomodulatory compound.

In some embodiments, the immunomodulatory compound is selected from the group consisting of lenalidomide, pomalidomide, thalidomide, 3-(5-amino-2-methyl-4-oxo-4H-quinazolin-3-yl)-piperidine-2,6-dione, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-di-hydro-isoindol-2-yl)-piperidine-2,6-dione, and combinations thereof, or enantiomers or a mixture of enantiomers thereof, or pharmaceutically acceptable salts, solvates, hydrates, co-crystals, clathrates, or polymorphs thereof as a single agent or as a part of a combination therapy.

In some embodiments, the compounds provided herein block induction of HIF1α gene expression profile of IBC cells. Without being bound to a particular theory, it is believed that the compounds provided herein may be used, either independently, in combination, or in combination with other anti-cancer agents in the therapy of locally advanced breast cancer and/or inflammatory breast cancer based at least in part on their HIFα activity.

Further provided herein are methods of treating, preventing, and/or managing breast cancer, comprising orally administering to a patient in need of such treatment, prevention, or management, a dose of 0.5 mg to 20 mg of a compound provided herein, or an enantiomer or a mixture of enantiomers thereof, or a pharmaceutically acceptable salt, solvate, hydrate, co-crystal, clathrate, or a polymorph thereof; alone or in combination with a therapy conventionally used to treat, prevent, or manage breast cancer. Examples of such conventional therapies include, but are not limited to, DNA damaging chemothereapy, anti-mitotics (e.g. taxanes, *vinca* alkaloids), anti-metabolites, kinase inhibitors, epigenetic targeted agents, other cytotoxic or pathway targeted agents, and radiation thereapy.

In another embodiment, provided herein is a method of treating, preventing, and/or managing breast cancer, comprising orally administering to a patient in need of such treatment, prevention, or management, a continuous daily dose of 0.5 mg to 20 mg of a compound provided herein, until disease progression is intermittent.

Also provided herein are pharmaceutical compositions, single unit dosage forms, dosing regimens and kits which comprise one or more of the compounds provided herein, or enantiomers or mixtures of enantiomers thereof, or pharmaceutically acceptable salts, solvates, hydrates, co-crystals, clathrates, polymorphs, prodrugs thereof, and a second, or additional, active agent. Second active agents include specific combinations, or "cocktails," of drugs. Second active agents include small molecules and large molecules (e.g., proteins and antibodies), examples of which are provided herein, as well as stem cells. Methods or therapies that can be used in combination with the administration of the compound provided herein include, but are not limited to, surgery, blood transfusions, immunotherapy, biological therapy, radiation therapy, and other non-drug based therapies presently used to treat, prevent or manage disease and conditions associated with or characterized by undesired angiogenesis.

In one embodiment, the additional active agent is selected from the group consisting of an anti-mitotic agent, such as a taxane (e.g., paclitaxel (Taxol®), docetaxel (Taxotere®), protein-bound paclitaxel (Abraxane®)) or a *vinca* alkaloid (e.g., vincristine, vinblastine (Velban®), vindesine, vinorelbine); a cytidine analog (e.g., 5-azacytidine (Vidaza®); a topoisomerase inhibitor (e.g., doxorubicin (Adriamycin®), daunorubicin, mitoxantrone, amsacrine, aurintricarboxylic acid, irinotecan, topotecan, camtothecin, lamellarin D, etoposide, teniposide, elliptcines and HU-331), capecitabine (Xeloda®), gemcitabine (Gemzar®)); a HDAC inhibitor (e.g., romidepsin, vorinostat, panobinostat, valproic acid, belinostat, etinostat); a HER2 inhibitor (e.g., trastuzumab (Herceptin®), trastuzumab emtansine (T-DM1), lapatinib (Tykerb®), bevacizumab (Avastatin®), pertuzumab (Perjeta®)); a platin (e.g., cisplatin, carboplatin, oxaliplatin); a Bcl-2 inhibitor (e.g., navitoclax); PI3K/AKT/mTOR pathway inhibitors (e.g., GDC-0941, CC-223, CC-115); everolimus (Afinitor®), anastrozole (Arimidex®), exemestane (Aromacin®), cyclophosphamide (Cytoxan®), eribulin (Halaven®), fluoxymesterone (Halotestin®), fulvestrant (Faslodex®), letrozole (Femara®), tamoxifen (Nolvadex®), and methotrexate (Trexall®).

In one embodiment, a compound provided herein is administered in an amount of about 5 to about 50 mg per day.

In one embodiment, lenalidomide is administered in an amount of about 5, 10, 15, 25, 30 or 50 mg per day.

In one embodiment, pomalidomide is administered in an amount of about 5, 10, 15, 25, 30 or 50 mg per day.

In one embodiment, thalidomide is administered in an amount of about 5, 10, 15, 25, 30 or 50 mg per day.

In one embodiment, 3-(5-amino-2-methyl-4-oxo-4H-quinazolin-3-yl)-piperidine-2,6-dione is administered in an amount between 0.5 mg to 20 mg per day.

In one embodiment, 3-(4-((4-(morpholinomethyl)benzyl)oxy)-1-oxoisoindolin-2-yl)piperidine-2,6-dione is administered in an amount between 0.5 mg to 20 mg per day.

In one embodiment, (S)-3-(4-((4-(morpholinomethyl)benzyl)oxy)-1-oxoisoindolin-2-yl)piperidine-2,6-dione is administered in an amount between 0.5 mg to 20 mg per day.

In one embodiment, 3-(1-oxo-4-(4-(2-(pyrrolidin-1-yl)ethoxy)benzyloxy)isoindolin-2-yl)-piperidine-2,6-dione is administered in an amount between 0.5 mg to 20 mg per day.

In one embodiment, 3-(4-(4-(2-morpholin-4-yl-ethoxy)-benzyloxy)-1-oxoisoindolin-2-yl)-piperidine-2,6-dione is administered in an amount between 0.5 mg to 20 mg per day.

In one embodiment, 3-(4-(4-(2-morpholin-4-yl-ethyl)-benzyloxy)-1-oxo-1,3-dihydro-isoindol-2-yl)-piperidine-2,6-dione is administered in an amount between 0.5 mg to 20 mg per day.

In one embodiment, the compound provided herein are administered twice per day.

In one embodiment, the compound provided herein are orally administered.

In one embodiment, the compound provided herein are administered in a capsule or tablet.

In one embodiment, the compound provided herein are administered for 21 days followed by seven days rest in a 28 day cycle.

5.1 Compounds

Compounds suitable for use in the methods provided herein are lenalidomide, pomalidomide, thalidomide, 3-(5-amino-2-methyl-4-oxo-4H-quinazolin-3-yl)-piperidine-2,6-dione ("Compound A"), 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl)-piperidine-2,6-dione and/or other immunomodulatory compounds, or enantiomers or mixtures of enantiomers thereof; or pharmaceutically acceptable salts, solvates, hydrates, co-crystals, clathrates, or polymorphs thereof.

Compounds for the methods provided herein include, but are not limited to, the substituted 2-(2,6-dioxopiperidin-3-yl) phthalimides and substituted 2-(2,6-dioxopiperidin-3-yl)-1-oxoisoindoles described in U.S. Pat. Nos. 6,281,230 and 6,316,471, both to G. W. Muller, et al. Still other specific compounds disclosed herein belong to a class of isoindole-imides disclosed in U.S. Pat. Nos. 6,395,754, 6,555,554, 7,091,353, U.S. patent publication no. 2004/0029832, and International Publication No. WO 98/54170, each of which is incorporated herein by reference.

Compound A, 3-(5-amino-2-methyl-4-oxo-4H-quinazolin-3-yl)-piperidine-2,6-dione, has the following structure:

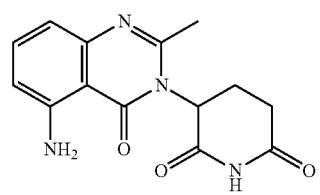

A

Compound A can be prepared according to the methods described in the Examples provided herein or as described in U.S. Pat. No. 7,635,700, the disclosure of which is incorporated herein by reference in its entirety. The compound can be also synthesized according to other methods apparent to those of skill in the art based upon the teaching herein. In certain embodiments, the solid Compound A is a crystalline solid as described in U.S. Provisional patent application Ser.

No. 13/417,055, filed Mar. 9, 2012, which is incorporated herein by reference in its entirety.

Also provided herein are compounds of formula (I):

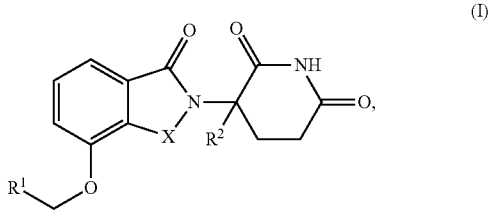

or a pharmaceutically acceptable salt, solvate or stereoisomer thereof, wherein:

X is C=O or CH$_2$;

R$^1$ is —Y—R$^3$;

R$^2$ is H or (C$_1$-C$_6$)alkyl;

Y is: 6 to 10 membered aryl, heteroaryl or heterocycle, each of which may be optionally substituted with one or more halogen; or a bond;

R$^3$ is: —(CH$_2$)$_n$-aryl, —O—(CH$_2$)$_n$-aryl or —(CH$_2$)$_n$—O-aryl, wherein the aryl is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen;

—(CH$_2$)$_n$-heterocycle, —O—(CH$_2$)$_n$-heterocycle or —(CH$_2$)$_n$—O-heterocycle, wherein the heterocycle is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; or —(CH$_2$)$_n$-heteroaryl, —O—(CH$_2$)$_n$-heteroaryl or —(CH$_2$)$_n$—O-heteroaryl, wherein the heteroaryl is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; and n is 0, 1, 2 or 3.

In one embodiment, examples of compounds of formula (I) include, but are not limited to the compounds described in U.S. Patent Publication No. 2011/0196150, the disclosure of which is incorporated by reference herein in its entirety. In some embodiments, the compound is selected from the group consisting of 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl)-piperidine-2,6-dione or enantiomers or mixtures of enantiomers thereof; or pharmaceutically acceptable salts, solvates, hydrates, co-crystals, clathrates, or polymorphs thereof.

In some embodiments, certain compounds provided herein can be prepared according to the methods described in the Examples provided herein or as described in U.S. Provisional Pat. App. No. 61/681,447 filed Aug. 9, 2012, the disclosure of which is incorporated herein by reference in its entirety.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure.

5.2 Definitions

To facilitate understanding of the disclosure set forth herein, a number of terms are defined below.

The term "subject" or "patient" refers to an animal, including, but not limited to, a mammal, including a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease, or lengthening the time during which the remains in remission.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation*, Gibson Ed., CRC Press LLC: Boca Raton, Fla., 2004).

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The term "relapsed" refers to a situation where a subject or a mammal, which has had a remission of cancer after therapy has a return of cancer cells.

As used herein, an "effective patient tumor response" refers to any increase in the therapeutic benefit to the patient. An "effective patient tumor response" can be, for example, a 5%, 10%, 25%, 50%, or 100% decrease in the rate of progress of the tumor. An "effective patient tumor response" can be, for example, a 5%, 10%, 25%, 50%, or 100% decrease in the physical symptoms of a cancer. An "effective patient tumor response" can also be, for example, a 5%, 10%, 25%, 50%, 100%, 200%, or more increase in the response of the patient, as measured by any suitable means, such as gene expression, cell counts, assay results, etc.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating a cancer in a patient or in a tumor cell culture. Similarly, the "monitoring," when used in connection with patient compliance, either individually, or in a clinical trial, refers to the tracking or confirming that the patient is actually taking the immunomodulatory compound being tested as prescribed. The monitoring can be performed, for example, by following the expression of mRNA or protein biomarkers.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

The term "refractory or resistant" refers to a circumstance where a subject or a mammal, even after intensive treatment, has residual cancer cells in his body.

The term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

The term "sensitivity" and "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least a 5%, or more, in the effectiveness of the tumor treatment.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide or a portion thereof.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition.

An mRNA from a patient sample can be "upregulated" when treated with an immunomodulatory compound, as compared to a non-treated control. This upregulation can be, for example, an increase of about 5%, 10%, 20%, 30%, 40%, 50%, 60%, 70%, 90%, 100%, 200%, 300%, 500%, 1,000%, 5,000% or more of the comparative control mRNA level.

Alternatively, an mRNA can be "downregulated", or expressed at a lower level, in response to administration of certain immunomodulatory compounds or other agents. A downregulated mRNA can be, for example, present at a level of about 99%, 95%, 90%, 80%, 70%, 60%, 50%, 40%, 30%, 20%, 10%, 1% or less of the comparative control mRNA level.

Similarly, the level of a polypeptide or protein biomarker from a patient sample can be increased when treated with an immunomodulatory compound, as compared to a non-treated control. This increase can be about 5%, 10%, 20%, 30%, 40%, 50%, 60%, 70%, 90%, 100%, 200%, 300%, 500%, 1,000%, 5,000% or more of the comparative control protein level.

Alternatively, the level of a protein biomarker can be decreased in response to administration of certain immunomodulatory compounds or other agents. This decrease can be, for example, present at a level of about 99%, 95%, 90%, 80%, 70%, 60%, 50%, 40%, 30%, 20%, 10%, 1% or less of the comparative control protein level.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulfonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of the compounds provided herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of the compounds provided herein that comprise —NO, —NO$_2$, —ONO, or —ONO$_2$ moieties. Prodrugs can be prepared using such methods as described in *Burger's Medicinal Chemistry and Drug Discovery*, 172-178, 949-982 (Manfred E. Wolff ed., 5th ed. 1995), and *Design of Prodrugs* (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," and "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. In certain embodiments, a stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, greater than about 70% by weight, or greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

5.3 Clinical Trials Endpoints for Cancer Approval

"Overall survival" is defined as the time from randomization until death from any cause, and is measured in the intent-to-treat population. Overall survival should be evaluated in randomized controlled studies. Demonstration of a statistically significant improvement in overall survival can be considered to be clinically significant if the toxicity profile is acceptable, and has often supported new drug approval.

Several endpoints are based on tumor assessments. These endpoints include disease free survival (DFS), objective response rate (ORR), time to progression (TTP), progression-free survival (PFS), and time-to-treatment failure (TTF). The collection and analysis of data on these time-dependent endpoints are based on indirect assessments, calculations, and estimates (e.g., tumor measurements).

Generally, "disease free survival" (DFS) is defined as the time from randomization until recurrence of tumor or death from any cause. Although overall survival is a conventional endpoint for most adjuvant settings, DFS can be an important endpoint in situations where survival may be prolonged, making a survival endpoint impractical. DFS can be a surrogate for clinical benefit or it can provide direct evidence of clinical benefit. This determination is based on the magnitude of the effect, its risk-benefit relationship, and the disease setting. The definition of DFS can be complicated, particularly when deaths are noted without prior tumor progression documentation. These events can be scored either as disease recurrences or as censored events. Although all methods for statistical analysis of deaths have some limitations, considering all deaths (deaths from all causes) as recurrences can minimize bias. DFS can be overestimated using this definition, especially in patients who die after a long period without observation. Bias can be introduced if the frequency of long-term follow-up visits is dissimilar between the study arms or if dropouts are not random because of toxicity.

"Objective response rate" (ORR) is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study. If available, standardized criteria should be used to ascertain response. A variety of response criteria have been considered appropriate (e.g., RECIST criteria) (Therasse et al., (2000) *J. Natl. Cancer Inst,* 92: 205-16). The significance of ORR is assessed by its magnitude and duration, and the percentage of complete responses (no detectable evidence of tumor).

"Time to progression" (TTP) and "progression-free survival" (PFS) have served as primary endpoints for drug approval. TTP is defined as the time from randomization until objective tumor progression; TTP does not include deaths. PFS is defined as the time from randomization until objective tumor progression or death. Compared with TTP, PFS is the preferred regulatory endpoint. PFS includes deaths and thus can be a better correlate to overall survival. PFS assumes patient deaths are randomly related to tumor progression. However, in situations where the majority of deaths are unrelated to cancer, TTP can be an acceptable endpoint.

As an endpoint to support drug approval, PFS can reflect tumor growth and be assessed before the determination of a survival benefit. Its determination is not confounded by subsequent therapy. For a given sample size, the magnitude of effect on PFS can be larger than the effect on overall survival. However, the formal validation of PFS as a surrogate for survival for the many different malignancies that exist can be difficult. Data are sometimes insufficient to allow a robust evaluation of the correlation between effects on survival and PFS. Cancer trials are often small, and proven survival benefits of existing drugs are generally modest. The role of PFS as an endpoint to support licensing approval varies in different cancer settings. Whether an improvement in PFS represents a direct clinical benefit or a surrogate for clinical benefit depends on the magnitude of the effect and the risk-benefit of the new treatment compared to available therapies.

"Time-to-treatment failure" (TTF) is defined as a composite endpoint measuring time from randomization to discontinuation of treatment for any reason, including disease progression, treatment toxicity, and death. TTF is not recommended as a regulatory endpoint for drug approval. TTF does not adequately distinguish efficacy from these additional variables. A regulatory endpoint should clearly distinguish the efficacy of the drug from toxicity, patient or physician withdrawal, or patient intolerance.

5.4 Second Active Agents

The compounds provided herein may be combined with one or more other pharmacologically active compounds ("second active agents") in methods and compositions provided herein. It is believed that certain combinations work synergistically in the treatment of particular types of cancer, and certain diseases and conditions associated with or characterized by undesired angiogenesis. The compounds provided herein can also work to alleviate adverse effects associated with certain second active agents, and some second active agents can be used to alleviate adverse effects associated with the compounds provided herein.

One or more second active ingredients or agents can be used in the methods and compositions provided herein with one or more of the compounds provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. In certain embodiments, large molecule active agents are biological molecules, such as naturally occurring or artificially made proteins. Proteins that are particularly useful in this disclosure include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the disclosure include, but are not limited to: filgrastim, which is sold in the United States under the trade name NEUPOGEN® (Amgen, Thousand Oaks, Calif.); sargramostim, which is sold in the United States under the trade name LEUKINE® (Immunex, Seattle, Wash.); and recombinant EPO, which is sold in the United States under the trade name EPGEN® (Amgen, Thousand Oaks, Calif.).

Recombinant and mutated forms of GM-CSF can be prepared as described in U.S. Pat. Nos. 5,391,485; 5,393,870; and 5,229,496; the disclosure of each of which is incorporated herein by reference in its entirety. Recombinant and mutated forms of G-CSF can be prepared as described in U.S. Pat. Nos. 4,810,643; 4,999,291; 5,528,823; and 5,580,755; the disclosure of each of which is incorporated herein by reference in its entirety.

This disclosure encompasses the use of native, naturally occurring, and recombinant proteins. The disclosure further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, PEGylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with the compounds provided herein include monoclonal and polyclonal antibodies. Examples of antibodies include, but are not limited to, trastuzumab (Herceptin®), rituximab (Rituxan®), bevacizumab (Avastin™), pertuzumab (Perjeta™), tositumomab (Bexxar®), edrecolomab (Panorex®), panitumumab and G250. The compounds provided herein can also be combined with or used in combination with anti-TNF-α antibodies.

Large molecule active agents may be administered in the form of anti-cancer vaccines. For example, vaccines that secrete, or cause the secretion of, cytokines such as IL-2, SCF, CXC14 (platelet factor 4), G-CSF, and GM-CSF can be used in the methods, pharmaceutical compositions, and kits of the disclosure. See, e.g., Emens, L. A., et al., *Curr. Opinion Mol. Ther.* 3(1):77-84 (2001).

Second active agents that are small molecules can also be used to alleviate adverse effects associated with the administration of the compounds provided herein. However, like some large molecules, many are believed to be capable of providing a synergistic effect when administered with (e.g., before, after or simultaneously) the compounds provided herein. Examples of small molecule second active agents include, but are not limited to, anti-cancer agents, antibiotics, immunosuppressive agents, and steroids.

Examples of anti-cancer agents include, but are not limited to: Abraxane®; ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; b-FGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g.,) GLEEVEC®, imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In some embodiments, the additional active agent is selected from the group consisting of oblimersen (GENASENSE®), remicade, docetaxel, celecoxib, melphalan, dexamethasone (DECADRON®), steroids, gemcitabine, cisplatinum, temozolomide, etoposide, cyclophosphamide, temodar, carboplatin, procarbazine, gliadel, tamoxifen, topotecan, methotrexate, ARISA®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel, ganciclovir, adriamycin, estramustine sodium phosphate (EMCYT®), sulindac, and etoposide.

In other embodiments, the additional active agent is selected from the group consisting of a taxane (e.g., paclitaxel (Taxol®), docetaxel (Taxotere®), protein-bound paclitaxel (Abraxane®)), a cytidine analog (e.g., 5-azacytidine (Vidaza®), capecitabine (Xeloda®), gemcitabine (Gemzar®)), a HDAC inhibitor (e.g., romidepsin, vorinostat, panobinostat, valproic acid, belinostat, etinostat), a HER2 inhibitor (e.g., trastuzumab (Herceptin®), trastuzumab emtansine (T-DM1), lapatinib (Tykerb®), bevacizumab (Avastatin®), pertuzumab (Perjeta®)), doxorubicin (Adriamycin®), everolimus (Afinitor®), anastrozole (Arimidex®), exemestane (Aromacin®), cyclophosphamide (Cytoxan®), eribulin (Halaven®), fluoxymesterone (Halotestin®), fulvestrant (Faslodex®), letrozole (Femara®), tamoxifen (Nolvadex®), vinblastine (Velban®), and methotrexate (Trexall®).

5.5 Biomarkers

Provided herein are methods relating to the use of mRNAs or proteins as biomarkers to ascertain the effectiveness of breast cancer therapy. mRNA or protein levels can be used to determine whether a particular agent is likely to be successful in the treatment of breast cancer.

A biological marker or "biomarker" is a substance whose detection indicates a particular biological state, such as, for example, the presence of cancer. In some embodiments, biomarkers can either be determined individually, or several biomarkers can be measured simultaneously.

In some embodiments, a "biomarker" indicates a change in the level of mRNA expression that may correlate with the risk or progression of a disease, or with the susceptibility of the disease to a given treatment. In some embodiments, the biomarker is a nucleic acid, such as a mRNA or cDNA.

In additional embodiments, a "biomarker" indicates a change in the level of polypeptide or protein expression that may correlate with the risk, susceptibility to treatment, or progression of a disease. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

In certain embodiments, the biomarker is protein associated with cereblon ("CRBN"), e.g., Aiolos (IKZF3) or Ikaros (IKZF1). Such proteins are described in U.S. Provisional Patent Application No. 61/666,703, filed Jun. 29, 2012, the disclosure of which is hereby incorporated by reference in its entirety.

Provided herein is a method for treating or managing locally advanced breast cancer, comprising:

(i) identifying a patient having locally advanced breast cancer sensitive to treatment with a compound selected from lenalidomide, pomalidomide, thalidomide, 3-(5-amino-2-methyl-4-oxo-4H-quinazolin-3-yl)-piperidine-2,6-dione, 3-(4-((4-(morpholinomethyl)benzyl)oxy)-1-oxoisoindolin-2-yl)piperidine-2,6-dione, (S)-3-(4-((4-(morpholinomethyl)benzyl)oxy-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2, 6-dione, 3-(4-(4-(2-morpholin-4-yl-ethyl)-benzyloxy)-1-oxo-1,3-dihydro-isoindol-2-yl)-piperidine-2,6-dione, or an enantiomer or mixture of enantiomers thereof or a pharmaceutically acceptable salt, solvate, hydrate, co-crystal, clathrate, or polymorph thereof; and (ii) administering to the patient a therapeutically effective amount the compound selected in step (i). In one embodiment, identifying a patient having locally advanced breast cancer sensitive to treatment comprises detecting the level of expression of CRBN, Aiolos (IKZF3) or Ikaros (IKZF1) expression within the cancer.

In another embodiment, provided herein is a method of selecting a group of locally advanced breast cancer patients based on the level of CRBN expression, or the levels of Aiolos (IKZF3) or Ikaros (IKZF1) expression within the cancer, for the purposes of predicting clinical response, monitoring clinical response, or monitoring patient compliance to dosing by 3-(5-amino-2-methyl-4-oxo-4H-quinazolin-3-yl)-piperidine-2,6-dione, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl)-piperidine-2,6-dione, or a stereoisomer thereof, or a pharmaceutically acceptable salt, solvate, hydrate, co-crystal, clathrate, or polymorph thereof.

Also provided herein are methods of identifying or monitoring locally advanced breast cancer patient resistance to 3-(5-amino-2-methyl-4-oxo-4H-quinazolin-3-yl)-piperidine-2,6-dione, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl) piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl)-piperidine-2,6-dione therapy, based on the presence or appearance of mutations within a CRBN gene, including but not limited to the Aiolos (IKZF3) or Ikaros (IKZF1) genes.

5.6 Methods of Treatment, Prevention and/or Management

In one embodiment, provided herein is a method of treating, preventing, and/or managing breast cancer, which comprises administering to a patient one or more of the compounds provided herein, or enantiomers or mixtures of enantiomers thereof, or pharmaceutically acceptable salts, solvates, hydrates, co-crystals, clathrates, or polymorphs thereof.

Also provided herein are methods of treating patients who have been previously treated for breast cancer but are non-responsive to standard therapies, as well as those who have not previously been treated. In some embodiments, provided herein are methods of treating patients regardless of patient's age, although some diseases or disorders are more common in certain age groups. In other embodiments, provided herein are methods of treating patients who have undergone surgery in an attempt to treat the disease or condition at issue, as well as those who have not. Because patients with breast cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In certain embodiments, the breast cancer is a solid tumor. In certain embodiments, the solid tumor is metastatic. In certain embodiments, the solid tumor is drug-resistant.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiment, a therapeutically or prophylactically effective amount is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day.

In certain embodiments, the therapeutically or prophylactically effective amount is about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of a compound provided herein for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day to patients with breast cancer. In a particular embodiment, the compound can be administered in an amount of about 10 mg/day to patients with breast cancer.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the amount of the compound administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, or enantiomers or mixtures of enantiomers thereof, or pharmaceutically acceptable salts, solvates, hydrates, co-crystals, clathrates, or polymorphs thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of one or more of the compounds provided herein. In certain embodiments, the patient to be treated with one of the methods provided herein has been treated with anticancer therapy prior to the administration of one or more of the compounds provided herein. In certain embodiments, the patient to be treated with one of the methods provided herein has developed drug resistance to the anticancer therapy.

The methods provided herein encompass treating a patient regardless of patient's age, although some diseases or disorders are more common in certain age groups. Further provided herein is a method for treating a patient who has undergone surgery in an attempt to treat the disease or condition at issue, as well in one who has not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

In some embodiments, the compounds provided herein, or enantiomers or mixtures of enantiomers thereof, or pharmaceutically acceptable salts, solvates, hydrates, co-crystals, clathrates, or polymorphs thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compounds provided herein, or enantiomers or mixtures of enantiomers thereof, or pharmaceutically acceptable salts, solvates, hydrates, co-crystals, clathrates, or polymorphs thereof, may be formulated, alone or together, in suitable dosage unit with pharmaceutically acceptable excipients, carriers, adjuvants and vehicles, appropriate for each route of administration.

In one embodiment, the compounds provided herein, or enantiomers or mixtures of enantiomers thereof, or pharmaceutically acceptable salts, solvates, hydrates, co-crystals, clathrates, or polymorphs thereof, is administered orally. In another embodiment, one or more of the compounds provided herein, or enantiomers or mixtures of enantiomers thereof, or pharmaceutically acceptable salts, solvates, hydrates, co-crystals, clathrates, or polymorphs thereof, is administered parenterally. In yet another embodiment, the compounds provided herein, or enantiomers or mixtures of enantiomers thereof, or pharmaceutically acceptable salts, solvates, hydrates, co-crystals, clathrates, or polymorphs thereof, is administered intravenously.

The compounds provided herein, or enantiomers or mixtures of enantiomers thereof, or pharmaceutically acceptable salts, solvates, hydrates, co-crystals, clathrates, or polymorphs thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compounds provided herein, or enantiomers or mixtures of enantiomers thereof, or pharmaceutically acceptable salts, solvates, hydrates, co-crystals, clathrates, or polymorphs thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as a compound provided herein, are administered once or more than once each day, for example, for a period of time. The term "continuous" is intended to mean that a therapeutic compound, such as a compound provided herein, are administered daily for an uninterrupted period of at least 10 days to 52 weeks. The term "intermittent" or "intermittently" as used herein is intended to mean stopping and starting at either regular or irregular intervals. For example, intermittent administration of a compound provided herein is administration for one to six days per week, administration in cycles (e.g., daily administration for two to eight consecutive weeks, then a rest period with no administration for up to one week), or administration on alternate days. The term "cycling" as used herein is intended to mean that a therapeutic compound is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, one or more of the compounds provided herein, or an enantiomer or a mixture of enantiomers thereof; or a pharmaceutically acceptable salt, solvate, hydrate, co-crystal, clathrate, or polymorph thereof, is administered once a day. In another embodiment, one or more of the compounds provided herein, or enantiomers or mixtures of enantiomers thereof, or pharmaceutically acceptable salts, solvates, hydrates, co-crystals, clathrates, or polymorphs thereof, are administered twice a day. In yet another embodiment, one or more of the compounds provided herein, or enantiomers or mixtures of enantiomers thereof, or pharmaceutically acceptable salts, solvates, hydrates, co-crystals, clathrates, or polymorphs thereof, is administered three times a day. In still another embodiment, one or more of the compounds provided herein, or enantiomers or mixtures of enantiomers thereof, or pharmaceutically acceptable salts, solvates, hydrates, co-crystals, clathrates, or polymorphs thereof, are administered four times a day.

In certain embodiments, one or more of the compounds provided herein, or enantiomers or mixtures of enantiomers thereof, or pharmaceutically acceptable salts, solvates, hydrates, co-crystals, clathrates, or polymorphs thereof, are administered once per day from one day to six months, from one week to three months, from one week to four weeks, from one week to three weeks, or from one week to two weeks. In certain embodiments, one or more of the compounds provided herein, or pharmaceutically acceptable salts or solvates thereof, are administered once per day for one week, two weeks, three weeks, or four weeks. In one embodiment, one or more of the compounds provided herein, or enantiomers or mixtures of enantiomers thereof, or pharmaceutically acceptable salts, solvates, hydrates, co-crystals, clathrates, or polymorphs thereof, are administered once per day for one week. In another embodiment, one or more of the compounds provided herein, or enantiomers or mixtures of enantiomers thereof, or pharmaceutically acceptable salts, solvates, hydrates, co-crystals, clathrates, or polymorphs thereof, are administered once per day for two weeks. In yet another embodiment, one or more of the compounds provided herein, or enantiomers or mixtures of enantiomers thereof, or pharmaceutically acceptable salts, solvates, hydrates, co-crystals, clathrates, or polymorphs thereof, are administered once per day for three weeks. In still another embodiment, the one or more of compounds provided herein, or enantiomers or mixtures of enantiomers thereof, or pharmaceutically acceptable salts, solvates, hydrates, co-crystals, clathrates, or polymorphs thereof, are administered once per day for four weeks.

5.6.1 Combination Therapy with a Second Active Agent

The compounds provided herein, or enantiomers or mixtures of enantiomers thereof, or pharmaceutically acceptable salts, solvates, hydrates, co-crystals, clathrates, or polymorphs thereof, can also be combined or used in combination with other therapeutic agents useful in the treatment and/or prevention of cancer described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, or an enantiomer or mixture of enantiomers thereof; or a pharmaceutically acceptable salt, solvate, hydrate, co-crystal, clathrate, or polymorph thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of one or more of the compounds provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of the compounds provided herein are independent of the route of administration of a second therapy. In one embodiment, the compounds provided herein are administered orally. In another embodiment, the compounds provided herein are administered intravenously. Thus, in accordance with these embodiments, the compounds provided herein are administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a compound provided herein and a second therapy are administered by the same mode of administration, orally or by IV. In another embodiment, a compound provided herein is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the first active agent, and any optional additional active agents concurrently administered to the patient. In certain embodiments, the second active agent is oblimersen (GENASENSE®), GM-CSF, G-CSF, SCF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Also encompassed herein is a method of increasing the dosage of an anti-cancer drug or agent that can be safely and effectively administered to a patient, which comprises administering to the patient (e.g., a human) a compound provided herein, or enantiomers or mixtures of enantiomers thereof, or pharmaceutically acceptable salts, solvates, hydrates, co-crystals, clathrates, or polymorphs thereof. Patients that can benefit by this method are those likely to suffer from an adverse effect associated with anti-cancer drugs for treating a specific cancer of the breast. The administration of a compound provided herein, or enantiomers or mixtures of enantiomers thereof, or pharmaceutically acceptable salts, solvates, hydrates, co-crystals, clathrates, or polymorphs thereof, alleviates or reduces adverse effects which are of such severity that it would otherwise limit the amount of anti-cancer drug.

In one embodiment, a compound provided herein, or enantiomers or mixtures of enantiomers thereof, or pharmaceutically acceptable salts, solvates, hydrates, co-crystals, clathrates, or polymorphs thereof, are administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, one or more of the compounds provided herein, or enantiomers or mixtures of enantiomers thereof, or pharmaceutically acceptable salts, solvates, hydrates, co-crystals, clathrates, or polymorphs thereof, are administered in combination with specific agents such as heparin, aspirin, coumadin, or G-CSF to avoid adverse effects that are associated with anti-cancer drugs such as but not limited to neutropenia or thrombocytopenia.

In one embodiment, the compounds provided herein, or enantiomers or mixtures of enantiomers thereof, or pharmaceutically acceptable salts, solvates, hydrates, co-crystals, clathrates, or polymorphs thereof, are administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering one or more of the compounds provided herein, or enantiomers or mixtures of enantiomers thereof, or pharmaceutically acceptable salts, solvates, hydrates, co-crystals, clathrates, or polymorphs thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that the compounds provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. Compounds provided herein, or enantiomers or mixtures of enantiomers thereof, or pharmaceutically acceptable salts, solvates, hydrates, co-crystals, clathrates, or polymorphs thereof, and other active ingredient can be administered to a patient prior to, during, or after the occurrence of the adverse effect associated with conventional therapy.

In one embodiment, the compounds provided herein can be administered in an amount ranging from about 0.1 to about 150 mg, from about 1 to about 25 mg, or from about 2 to about 10 mg orally and daily alone, or in combination with a second active agent disclosed herein (see, e.g., section 4.3), prior to, during, or after the use of conventional therapy.

5.6.2 Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, one or more of the compounds provided herein are administered daily in a single or divided doses in a four to six week cycle with a rest period of about a week or two weeks. The cycling method further allows the frequency, number, and length of dosing cycles to be increased. Thus, encompassed herein in certain embodiments is the administration of a compound provided herein, or enantiomers or mixtures of enantiomers thereof, or pharmaceutically acceptable salts, solvates, hydrates, co-crystals, clathrates, or polymorphs thereof, for more cycles than are typical when it is administered alone. In certain embodiments the compounds provided herein, or enantiomers or mixtures of enantiomers thereof, or pharmaceutically acceptable salts, solvates, hydrates, co-crystals, clathrates, or polymorphs thereof, are administered for a greater number of cycles that would typically cause dose-limiting toxicity in a patient to whom a second active ingredient is not also being administered.

In one embodiment, the compounds provided herein are administered daily and continuously for three or four weeks at a dose of from about 0.1 to about 150 mg/d followed by a break of one or two weeks.

In another embodiment, a compound provided herein and a second active ingredient are administered orally, with administration of the compound provided herein occurring 30 to 60 minutes prior to a second active ingredient, during a cycle of four to six weeks. In certain embodiments, the combination of the compound provided herein and a second active ingredient is administered by intravenous infusion over about 90 minutes every cycle. In certain embodiments, one cycle comprises the administration from about 0.1 to about 150 mg/day of the compound provided herein and from about 50 to about 200 mg/m$^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

5.7 Pharmaceutical Compositions and Dosage Forms

In one embodiment, provided herein are pharmaceutical compositions and dosage forms, which comprise one or more of the compounds provided herein, or enantiomers or mixtures of enantiomers thereof, or pharmaceutically acceptable salts, solvates, hydrates, co-crystals, clathrates, or polymorphs thereof. In another embodiment, pharmaceutical compositions and dosage forms further comprise one or more excipients.

In certain embodiments, pharmaceutical compositions and dosage forms provided herein also comprise one or more additional active ingredients. Consequently, pharmaceutical compositions and dosage forms provided herein comprise one or more of the compounds provided herein, or enantiomers or mixtures of enantiomers thereof, or pharmaceutically acceptable salts, solvates, hydrates, co-crystals, clathrates, or polymorphs thereof, and a second active agent. Examples of optional second, or additional, active ingredients are disclosed herein. See section 5.6.1.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal, or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein may vary depending on their use. For example, a dosage form used in the acute treatment of a disease may contain larger amounts of one or more of the active ingredients than a dosage form used in the chronic treatment of the same disease. Similarly, a parenteral dosage form may contain smaller amounts of one or more of the active ingredients than an oral dosage form used to treat the same disease. See, e.g., *Remington's Pharmaceutical Sciences*, 18th ed., Mack Publishing, Easton Pa. (1990).

Whether a particular excipient is suitable for incorporation into a pharmaceutical composition or dosage form provided herein depends on a variety of factors, including, but not limited to, the route of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, encompassed herein are pharmaceutical compositions and dosage forms that contain little, if any, lactose. As used herein, the term "lactose-free" means that the amount of lactose present, if any, is insufficient to substantially increase the degradation rate of an active ingredient.

Lactose-free compositions provided herein can comprise excipients that are listed, for example, in the *U.S. Pharmacopeia* (USP) 25-NF20 (2002). In certain embodiments, lactose-free compositions comprise active ingredients, a binder/filler, and a lubricant in pharmaceutically compatible and pharmaceutically acceptable amounts. In certain embodiments, lactose-free dosage forms comprise active ingredients, microcrystalline cellulose, pre-gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, in certain embodiments, provided herein are anhydrous compositions packaged using materials to prevent exposure to water such that they can be included in suitable formulary kits. Examples of suitable packaging include, but are not limited to, hermetically sealed foils, plastics, unit dose containers (e.g., vials), blister packs, and strip packs.

Encompassed herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In certain embodiments, the dosage forms provided herein comprise one or more of the compounds provided herein, or enantiomers or mixtures of enantiomers thereof, or pharmaceutically acceptable salts, solvates, hydrates, co-crystals, clathrates, or polymorphs thereof, in an amount ranging from about 0.10 to about 1000 mg, from about 0.10 to about 500 mg, from about 0.10 to about 200 mg, from about 0.10 to about 150 mg, from about 0.10 to about 100 mg, or from about 0.10 to about 50 mg. In certain embodiments, the dosage forms provided herein comprise one or more of the compounds provided herein, or enantiomers or mixtures of enantiomers thereof, or pharmaceutically acceptable salts, solvates, hydrates, co-crystals, clathrates, or polymorphs thereof, in an amount of about 0.1, about 1, about 2, about 5, about 7.5, about 10, about 12.5, about 15, about 17.5, about 20, about 25, about 50, about 100, about 150, or about 200 mg.

5.7.1 Oral Dosage Forms

In certain embodiments, pharmaceutical compositions provided herein that are suitable for oral administration are formulated as discrete dosage forms, examples of which include, but are not limited to, tablets (e.g., chewable tablets), caplets, capsules, and liquids (e.g., flavored syrups). Such dosage forms contain predetermined amounts of active ingredients and may be prepared by some known methods of pharmacy. See generally, *Remington's Pharmaceutical Sciences*, 18th ed., Mack Publishing, Easton Pa. (1990).

In certain embodiments, the oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms may be prepared by some known methods of pharmacy. In certain embodiments, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet is prepared by compression or molding. In certain embodiments, compressed tablets are be prepared by compressing in a suitable machine the active ingredients in a free-flowing form, e.g., powder or granules, optionally mixed with an excipient. In certain embodiments, molded tablets are made by molding in a suitable machine a mixture of a powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms provided herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, AVICEL-PH-101, AVICEL-PH-103 AVICEL RC-581, AVICEL-PH-105 (FMC Corporation, American Viscose Division, Avicel Sales, Marcus Hook, Pa.), and mixtures thereof. An specific binder is a mixture of microcrystalline cellulose and sodium carboxymethyl cellulose (e.g., AVICEL RC-581). Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein is present in from about 50 to about 99 weight percent of the pharmaceutical composition or dosage form.

Disintegrants are used in the compositions provided herein to provide tablets the ability to disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation. In certain embodiments, the pharmaceutical compositions provided herein comprise from about 0.5 to about 15 weight percent or from about 1 to about 5 weight percent of disintegrant.

Disintegrants that are suitable for use in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that are suitable for use in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, but are not limited to, a syloid silica gel (AEROSIL200, W.R. Grace Co., Baltimore, Md.), a coagulated aerosol of synthetic silica (Degussa Co. of Plano, Tex.), CAB-O-SIL (a pyrogenic silicon dioxide, Cabot Co. of Boston, Mass.), and mixtures thereof. In certain embodiments, if used at all, lubricants are used in an amount of less than about 1 weight percent of the pharmaceutical compositions or dosage forms into which they are incorporated.

In certain embodiments, provided herein is a solid oral dosage form, comprising one or more of the compounds provided herein, or enantiomers or mixtures of enantiomers thereof, or pharmaceutically acceptable salts, solvates, hydrates, co-crystals, clathrates, or polymorphs thereof; and one or more excipients selected from anhydrous lactose, microcrystalline cellulose, polyvinylpyrrolidone, stearic acid, colloidal anhydrous silica, and gelatin.

In certain embodiments, provided herein is a solid oral dosage form, comprising one or more of the compounds provided herein, or enantiomers or mixtures of enantiomers thereof, or pharmaceutically acceptable salts, solvates, hydrates, co-crystals, clathrates, or polymorphs thereof; and anhydrous lactose, microcrystalline cellulose, polyvinylpyrrolidone, stearic acid, colloidal anhydrous silica, and gelatin.

In certain embodiments, provided herein is a solid oral dosage form, comprising a hydrochloride sale of one or more of the compounds provided herein, or enantiomers or mixtures of enantiomers thereof, or pharmaceutically acceptable salts, solvates, hydrates, co-crystals, clathrates, or polymorphs thereof; and one or more excipients selected from anhydrous lactose, microcrystalline cellulose, polyvinylpyrrolidone, stearic acid, colloidal anhydrous silica, and gelatin.

In certain embodiments, provided herein is a solid oral dosage form, comprising a hydrochloride sale of one or more of the compounds provided herein, or enantiomers or mixtures of enantiomers thereof, or pharmaceutically acceptable salts, solvates, hydrates, co-crystals, clathrates, or polymorphs thereof; and anhydrous lactose, microcrystalline cellulose, polyvinylpyrrolidone, stearic acid, colloidal anhydrous silica, and gelatin.

5.7.2 Delayed Release Dosage Forms

In certain embodiments, the active ingredients provided herein are administered by controlled release means or by delivery devices. Examples include, but are not limited to, those described in U.S. Pat. Nos. 3,845,770; 3,916,899; 3,536,809; 3,598,123; 4,008,719, 5,674,533, 5,059,595, 5,591,767, 5,120,548, 5,073,543, 5,639,476, 5,354,556, and 5,733,566, each of which is incorporated herein by reference in its entirety. In certain embodiments, such dosage forms are be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Encompassed herein are single unit dosage forms suitable for oral administration, including, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.7.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Some suitable vehicles that can be used to provide parenteral dosage forms provided herein include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein. For example, cyclodextrin and its derivatives can be used to increase the solubility of a compound provided herein, e.g., a compound provided herein, or enantiomers or mixtures of enantiomers thereof, or pharmaceutically acceptable salts, solvates, hydrates, co-crystals, clathrates, or polymorphs thereof. See, e.g., U.S. Pat. No. 5,134,127, the disclosure of which is incorporated herein by reference in its entirety.

5.7.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences*, $16^{th}$ and $18^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein depend on the particular tissue to which a given pharmaceutical composition or dosage form will be applied. With that fact in mind, in certain embodiments, the excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Additional examples of such ingredients can be found, e.g., in *Remington's Pharmaceutical Sciences*, $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.7.5 Kits

In certain embodiments, active ingredients provided herein are not administered to a patient at the same time or by the same route of administration. Therefore, encompassed herein are kits which, when used by the medical practitioner, can simplify the administration of appropriate amounts of active ingredients to a patient.

In certain embodiments, a kit provided herein comprises a dosage form of a compound provided herein, or enantiomers or mixtures of enantiomers thereof, or pharmaceutically acceptable salts, solvates, hydrates, co-crystals, clathrates, or polymorphs thereof. In certain embodiments, the kit provided herein further comprises additional active agents, or a pharmacologically active mutant or derivative thereof, or a combination thereof. Examples of the additional active ingredients include, but are not limited to, those disclosed herein (see, e.g., section 4.3).

In certain embodiments, the kit provided herein further comprises a device that is used to administer the active ingredients. Examples of such devices include, but are not limited to, syringes, drip bags, patches, and inhalers.

In certain embodiments, the kit provided herein further comprises cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In an additional embodiment, provided herein is a kit useful for predicting the likelihood of an effective treatment or for monitoring the effectiveness of a treatment with one or more of the compounds provided herein. The kit comprises a solid support, nucleic acids contacting the support, where the nucleic acids are complementary to at least 20, 50, 100, 200, 350, or more bases of mRNA, and a means for detecting the expression of the mRNA in a biological sample.

In another embodiment, provided herein is a kit useful for predicting the likelihood of an effective treatment or for monitoring the effectiveness of a treatment with one or more of the compounds provided herein. The kit comprises a solid support, at least one nucleic acid contacting the support, where the nucleic acid is complementary to at least 20, 50, 100, 200, 350, 500, or more bases of mRNA, and a means for detecting the expression of the mRNA in a biological sample.

In certain embodiments, the kits provided herein employ means for detecting the expression of a biomarker by quantitative real-time PCR (QRT-PCR), microarray, flow cytometry or immunofluorescence. In other embodiments, the expression of the biomarker is measured by ELISA-based methodologies or other similar methods known in the art.

In another embodiment, the kit comprises a solid support, nucleic acids contacting the support, where the nucleic acids are complementary to at least 20, 50, 100, 200, 350, or more bases of mRNA, and a means for detecting the expression of the mRNA in a biological sample.

In certain embodiments, the kits provided herein employ means for detecting the expression of a biomarker by quantitative real-time PCR (QRT-PCR), microarray, flow cytometry or immunofluorescence. In other embodiments, the expression of the biomarker is measured by ELISA-based methodologies or other similar methods known in the art.

6. EXAMPLES

Certain embodiments provided herein are illustrated by the following non-limiting examples.

6.1 Preparation of 3-(4-amino-1-oxo-1,3-dihydro-isoindol-2-yl)-piperidine-2,6-dione (lenalidomide)

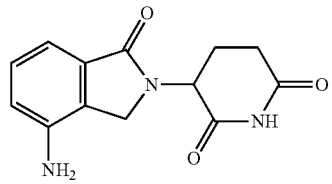 [SMILES: Nc1cccc2c1CN(C1CCC(=O)NC1=O)C2=O]

Methyl 2-bromomethyl-3-nitrobenzoate

A stirred mixture of methyl 2-methyl-3-nitrobenzoate (14.0 g, 71.7 mmol) and N-bromosuccinimide (15.3 g, 86.1 mmol) in carbon tetrachloride (200 mL) was heated under gentle reflux for 15 hours while a 100 W bulb situated 2 cm away was shining on the flask. The mixture was filtered and the solid was washed with methylene chloride (50 mL). The filtrate was washed with water (2×100 mL), brine (100 mL) and dried. The solvent was removed in vacuo and the residue was purified by flash chromatography (hexane/ethyl acetate, 8/2) to afford 19 g (96%) of the product as a yellow solid: mp 70.0-71.5° C.; 1H NMR (CDCl$_3$) δ 8.12-8.09 (dd, J=1.3 and 7.8 Hz, 1H), 7.97-7.94 (dd, J=1.3 and 8.2 Hz, 1H), 7.54 (t, J=8.0 Hz, 1H). 5.15 (s, 2H), 4.00 (s, 3H); $^{13}$C NMR (CDCl$_3$) δ 165.85, 150.58, 134.68, 132.38, 129.08, 127.80, 53.06, 22.69; HPLC, Water Nove-Pak/C18, 3.9×150 mm, 4 micron, 1 mL/min, 240 nm, 40/60 CH$_3$CN/0.1% H$_3$PO$_4$(aq) 7.27 min(98.92%); Anal. Calcd for C$_9$H$_8$NO$_4$Br: C, 39.44; H, 2.94; N, 5.1 1; Br, 29.15. Found: C, 39.46; H, 3.00; N, 5.00; Br, 29.1 1.

t-Butyl N-(1-oxo-4-nitroisoindolin-2-yl)-L-glutamine

Triethylamine (2.9 g, 28.6 mmol) was added dropwise to a stirred mixture of methyl 2-bromomethyl-3-nitrobenzoate (3.5 g, 13.0 mmol) and L-glutamine t-butyl ester hydrochloride (3.1 g, 13.0 mmol) in tetrahydrofuran (90 mL). The mixture was heated to reflux for 24 hours. To the cooled mixture was added methylene chloride (150 mL) and the mixture was washed with water (2×40 mL), brine (40 mL) and dried. The solvent was removed in vacuo and the residue was purified by flash chromatography (3% CH$_3$OH in methylene chloride) to afford 2.84 g (60%) of crude product which was used directly in the next reaction: 1H NMR (CDCl$_3$) δ 8.40 (d, J=8.1 Hz, 1H), 8.15 (d, J=7.5 Hz, 1H), 7.71 (t, J=7.8 Hz, 1H), 5.83 (s, 1H), 5.61 (s, 1H), 5.12 (d, J=19.4 Hz, 1H), 5.04-4.98 (m, 1H), 4.92 (d, J=19.4 Hz, 1H), 2.49-2.22 (m, 4H). 1.46 (s, 9H); HPLC, Waters Nova-Pak C18, 3.9×150 mm, 4 micron, 1 mL/min, 240 nm, 25/75 CH$_3$CN/0.1% H$_3$PO$_4$(aq) 6.75 min(99.94%).

N-(1-oxo-4-nitroisoindolin-2-yl)-L-glutamine

Hydrogen chloride gas was bubbled into a stirred 5° C. solution of t-butyl N-(1-oxo-4-nitro-isoindolin-2-yl)-L-glutamine (3.6 g, 9.9 mmol) in methylene chloride (60 mL) for 1 hour. The mixture was then stirred at room temperature for another hour. Ether (40 mL) was added and the resulting mixture was stirred for 30 minutes. The slurry was filtered, washed with ether and dried to afford 3.3 g of the product: 1H NMR (DMSO-d$_6$) δ 8.45 (d, J=8.1 Hz, 1H), 8.15 (d, J=7.5 Hz, 1H), 7.83 (t, J=7.9 Hz. 1H), 7.24 (s, 1H), 6.76 (s, 1H), 4.93 (s, 2H), 4.84-4.78 (dd, J=4.8 and 10.4 Hz, 1H), 2.34-2.10 (m, 4H); $^{13}$C NMR (DMSO-d$_6$) δ 173.03, 171.88, 165.96, 143.35, 137.49, 134.77, 130.10, 129.61, 126.95, 53.65, 48.13, 31.50, 24.69; Anal. Calcd for C$_{13}$H$_{13}$N$_3$O$_6$: C, 50.82; H, 4.26; N, 13.68. Found: C, 50.53; H. 4.37; N, 13.22.

(S)-3-(1-oxo-4-nitroisoindolin-2-yl)piperidine-2,6-dione

A stirred suspension mixture of N-(1-oxo-4-nitroisoindolin-2-yl)-L-glutamine (3.2 g, 10.5 mmol) in anhydrous methylene chloride (150 mL) was cooled to −40° C. with isopropanol/dry ice bath. Thionyl chloride (0.82 mL, 11.3 mmol) was added dropwise to the cooled mixture followed by pyridine (0.9 g. 1 1.3 mmol). After 30 min, triethylamine (1.2 g, 11.5 mmol) was added and the mixture was stirred at −30 to −40° C. for 3 hours. The mixture was poured into ice water (200 mL) and the aqueous layer was extracted with methylene chloride (40 mL). The methylene chloride solution was washed with water (2×60 mL), brine (60 mL) and dried. The solvent was removed in vacuo and the solid residue was slurried with ethyl acetate (20 mL) to give 2.2 g (75%) of the product as a white solid: mp 285° C.; 1H NMR (DMSO-d$_6$) δ: 1.04 (s, 1H), 8.49-8.45 (dd, J=0.8 and 8.2 Hz, 1H), 8.21-8.17 (dd, J=7.3 Hz, 1H), 7.84 (t, J=7.6 Hz, 1H), 5.23-5.15 (dd, J=4.9 and 13.0 Hz, 1H), 4.96 (dd, J=19.3 and 32.4 Hz, 2H), 3.00-2.85 (m, 1H), 2.64-2.49 (m, 2H), 2.08-1.98 (m, 1H); $^{13}$C NMR (DMSO-d$_6$) δ 172.79, 170.69, 165.93, 143.33, 137.40, 134.68, 130.15, 129.60, 127.02, 51.82, 48.43, 31.16. 22.23; HPLC, Waters Nove-Pak/C18, 3.9×150 mm, 4 micron, 1 mL/min, 240 nm, 20/80 CH$_3$CN/ 0.1% H$_3$PO$_4$(aq) 3.67 min(100%); Anal. Calcd for C$_{13}$H$_n$N$_3$O$_5$: C, 53.98; H, 3.83; N, 14.53. Found: C, 53.92; H, 3.70; N, 14.10.

3-(4-amino-1-oxo-1,3-dihydro-isoindol-2-yl)-piperidine-2,6-dione

A mixture of (S)-3-(1-oxo-4-nitroisoindolin-2-yl)piperidine-2,6-dione (1.0 g, 3.5 mmol) and 10% Pd/C (0.3 g) in methanol (600 mL) was hydrogenated in a Parr-Shaker apparatus at 50 psi of hydrogen for 5 hours. The mixture was filtered through Celite and the filtrate was concentrated in vacuo. The solid was slurried in hot ethyl acetate for 30 min, filtered and dried to afford 0.46 g (51%) of the product as a white solid: mp 235.5-239° C.; $^1$H NMR (DMSO-d$_6$) δ 11.01 (s, 1H). 7.19 (t, J=7.6 Hz, 1H). 6.90 (d. J=7.3 Hz, 1H), 6.78 (d, J=7.8 Hz, 1H), 5.42 (s, 2H). 5.12 (dd. J=5.1 and 13.1 Hz, 1H), 4.17 (dd, J=17.0 and 28.8 Hz, 2H), 2.92-2.85 (m, 1H). 2.64-2.49 (m, 1H). 2.34-2.27 (m, 1H), 2.06-1.99 (m, 1H); $^{13}$C NMR (DMSO-d$_6$) δ 172.85, 171.19, 168.84, 143.58, 132.22. 128.79, 125.56, 1 16.37, 1 10.39, 51.48, 45.49, 31.20, 22.74; HPLC. Waters Nova-Pak/C18, 3.9×150 mm, 4 micron, 240 nm, 10/90 CH$_3$CN/0.1% H$_3$PO$_4$(aq) 0.96 min(100%); Chiral analysis, Daicel Chiral Pak AD, 40/60 Hexane/IPA, 6.60 min(99.42%); Anal. Calcd for C$_{13}$H$_{13}$N$_3$O$_3$: C, 60.23; H, 5.05; N, 16.21. Found: C, 59.96; H. 4.98; N, 15.84.

3-(4-Amino-1-oxo-1,3-dihydro-isoindol-2-yl)-piperidine-2,6-dione may also be prepared by methods known in the art, for example, as provided in *Drugs of the Future,* 2003, 28(5): 425-431, the entirety of which is incorporated by reference.

6.2 Preparation of 4-amino-2-(2,6-dioxopiperidin-3-yl)-1H-isoindole-1,3-dione (pomalidomide)

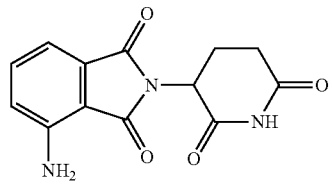 [SMILES: Nc1cccc2c1C(=O)N(C1CCC(=O)NC1=O)C2=O]

The preparation of 4-amino-2-(2,6-dioxopiperidin-3-yl)-1H-isoindole-1,3-dione is described, for example, in U.S. Pat. Nos. 7,812,169 and 7,709,502, the entirety of each of which is incorporated by reference.

Into a stirring solution of carboxybenzyloxy-L-glutamine (2.8 g, 10 mmols) in 40 mL anhydrous THF, 1,1-carbonyldiimidazole (1.92 g, 12 mmols) were added. The reaction mixture was heated under reflux for 18 hours. The THF was evaporated and the product was dissolved in chloroform. The chloroform layer was washed with water and brine and dried over anhydrous CaSO$_4$, filtered and evaporated to give white solid. The solid product was crystallized from ethyl ether to give 2.4 grams crystalline powder (90%). (Alternatively, carboxybenzyloxy-L-glutamine can be cyclized by treating with SOCl$_2$ in N,N-dimethylformamide at −70° C. to 0° C. for 1 hour to form the product). The reaction mixture was diluted with CHCl$_3$ and washed with 5% Na$_2$CO$_3$, dried over anhydrous Na$_2$SO$_4$, filtered, and evaporated to give 2.5 g (90% yield) S(−)-(3-benzyloxycarbonylamino)-glutarimide). $^1$H NMR (CDCl$_3$) δ 8.2 (1H, s broad), 7.4 (5H, s, aromatic), 5.8 (1H, d), 5.15 (2H, s), 4.4 (1H, dd, J=4.5, 3), 2.95-2.4 (3H, m), 1.86 (1H, d, t, J=11.5, 6.5). m.p. 122-124° C. (lit. 122-124° C.).

Into a solution of S(−)-(2-benzyloxycarbonylamino)glutarimide (1.2 g, 4.6 mmols) in 15 mL acetic acid glacial, 8 mL of 30% HBr/acetic acid solution was added at 20° C. The temperature of reaction mixture was raised to RT and stirred for 1 hour. White solid powder of S-(−)-2-amino-glutarimide HBr started appearing in reaction mixture. The solid was filtered and washed with 5 mL acetic acid glacial and then with ether to give 1.8 g (80%) product. Analysis on polarimeter of product showed (−) rotation, [a]$^{25}_D$ (c=1, water)=−37.5° and confirmed the product as S-(−)-2-amino-glutarimide. $^1$H NMR in DMSO-D$_6$ confirmed the product as 2-amino-L-glutarimide HBr.

Into a solution of (4.18 g, 20 mmols S-(−)-2-amino-glutarimide HBr in 50 mL of anhydrous DMF, 3.8 g (20 mmols) of 3-nitrophthalic anhydride was added. After adding 100 mL acetic acid (glacial), the reaction mixture was heated at about 70° C. to about 80° C. for about 24 hours. Thereafter, the solvents were evaporated under vacuum to yield an off-white solid. On adding 10 mL ethyl alcohol to the solid, an off-white powder product was formed. The product was separated and washed with 20 mL ethyl alcohol. $^1$H NMR (DMSO-D$_6$) δ 11.25 (1H, s broad), 8.35 (1H, d, J=7.2), 8.25 (1H, d, J=7.0), 8.15 (1H, t, J=8.0), 5.2 (1H, dd, J=5.5, 7.2), 3.00-2.85 (1H, m), 2.65-2.4 (2H, m), 2.15-2.05 (1H, m). m.p.: 228-229° C. (lit. 228.5-229.5° C.).

4-Nitro-thalidomide (1 g, 3.3 mmols) was dissolved in 50 mL dioxane/methanol 4:1 mixture and hydrogenated in a Parr hydrogenater at 40 psi of hydrogen in the presence of a Pd/C 5% catalyst for about 4 hours. After filtering the reaction mixture through a Celite filtering agent, the solvents were evaporated under vacuum to yield a yellow powder. The product was recrystallized from ethyl acetate/dioxane to yield 800 mg (85% purity) of S(−)-4-amino-thalidomide. $^1$H NMR in DMSO-D$_6$: 11.10 (1H, s broad), 7.45 (1H, t, J=7.5), 7.05 (1H, d, J=5.2), 6.95 (1H, d, J=5.2), 6.5 (2H, s broad), 5.05 (1H, dd, J=5.0, 13.42), 2.95-2.80 (1H, m), 2.65-2.5 (2H, m), 2.05-1.95 (1H, m). m.p. 318.2-319.5° C. Absolute configuration was determined by comparison of specific rotation $[\alpha]^{25}_D$ of (R)- and (S)-4-amino-2-(2,6-dioxopiperidin-3-yl)-1H-isoindole-1,3-dione to the analogous compounds R(+)- and S(−)-thalidomide. Analysis on polarimeter of product showed (−) rotation, $[\alpha]^{25}_D$ (C=0.5, dioxane)=−27.70° and confirmed the product as S(−)-4-amino-2-(2,6-dioxopiperidin-3-yl)-1H-isoindole-1,3-dione.

The two enantiomers were resolved by chiral HPLC column Welk-01 (10 mm×750 mm) and eluted with CH3CN/MeOH/H20 1:1:5 mixture. The retention time for the S(−) enantiomer was 33.74 minutes and for the R(+) enantiomer 35.62 minutes at a flow rate of 2 mL/min at 240 nm, respectively.

6.3 Preparation of 3-(5-amino-2-methyl-4-oxo-4H-quinazolin-3-yl)-piperidine-2,6-dione

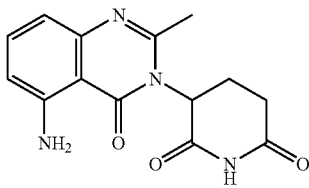 [SMILES: Cc1nc2cccc(N)c2c(=O)n1C1CCC(=O)NC1=O]

To a solution of potassium hydroxide (16.1 g, 286 mmol) in water (500 mL), was added 3-nitrophthalimide (25.0 g, 130 mmol) in portion at 0° C. The suspension was stirred at 0° C. for 3 hrs, and then heated to 30° C. for 3 hrs. To the solution, was added HCl (100 mL, 6N). The resulting suspension was cooled to 0° C. for 1 hr. The suspension was filtered and washed with cold water (2×10 mL) to give 3-nitro-phthalamic acid as a white solid (24.6 g, 90% yield): $^1$H NMR (DMSO-d$_6$) δ 7.69 (brs, 1H, NHH), 7.74 (t, J=8 Hz, 1H, Ar), 7.92 (dd, J=1, 8 Hz, 1H, Ar), 8.13 (dd, J=1, 8 Hz, 1H, Ar), 8.15 (brs, 1H, NHH), 13.59 (s, 1H, OH); $^{13}$C NMR (DMSO-d$_6$) δ 125.33, 129.15, 130.25, 132.54, 136.72, 147.03, 165.90, 167.31.

To a mixture of 3-nitro-phthalamic acid (24.6 g, 117 mmol) and potassium hydroxide (6.56 g, 117 mmol) in water (118 mL), was added a mixture of bromine (6 mL), potassium hydroxide (13.2 g, 234 mmol) in water (240 mL) at 0° C., followed by addition of a solution of potassium hydroxide (19.8 g, 351 mmol) in water (350 mL). After 5 minutes at 0° C., the mixture was heated in a 100° C. oil bath for 1 hr. The reaction solution was cooled to room temperature, and then, in an ice-water bath for 30 minutes. To the mixture, a solution of HCl (240 mL, 2N) was added dropwise at 0° C., and the resulting mixture was kept for 1 hr. The suspension was filtered and washed with water (5 mL) to give 2-amino-6-nitro-benzoic acid as yellow solid (15.6 g, 73% yield): HPLC: Waters Symmetry C$_{18}$, 5 µm, 3.9×150 mm, 1 mL/min, 240 nm, CH$_3$CN/0.1% H$_3$PO$_4$, 5% grad to 95% over 5 min, 5.83 min (85%); $^1$H NMR (DMSO-d$_6$) δ 6.90 (dd, J=1, 8 Hz, 1H, Ar), 7.01 (dd, J=1, 9 Hz, 1H, Ar), 7.31 (t, J=8 Hz, 1H, Ar), 8.5-9.5 (brs, 3H, OH, NH$_2$); $^{13}$C NMR (DMSO-d$_6$) δ 105.58, 110.14, 120.07, 131.74, 149.80, 151.36, 166.30; LCMS: MH=183.

A mixture of 2-amino-6-nitro-benzoic acid (1.5 g, 8.2 mmol) in acetic anhydride (15 mL) was heated at 200° C. for 30 minutes in a microwave oven. The mixture was filtered and washed with ethyl acetate (20 mL). The filtrate was concentrated in vacuo. The solid was stirred in ether (20 mL) for 2 hrs. The suspension was filtered and washed with ether (20 mL) to give 2-methyl-5-nitro-benzo[d][1,3]oxazin-4-one as a light brown solid (1.4 g, 85% yield): HPLC: Waters Symmetry C$_{18}$, 5 µm, 3.9×150 mm, 1 mL/min, 240 nm, CH$_3$CN/0.1% H$_3$PO$_4$, 5% grad 95% in 5 min, 5.36 min (92%); $^1$H NMR (DMSO-d$_6$) δ 2.42 (s, 3H, CH$_3$), 7.79 (dd, J=1, 8 Hz, 1H, Ar), 7.93 (dd, J=1, 8 Hz, 1H, Ar), 8.06 (t, J=8 Hz, 1H, Ar); $^{13}$C NMR (DMSO-d$_6$) δ 20.87, 107.79, 121.54, 128.87, 137.19, 147.12, 148.46, 155.18, 161.78; LCMS: MH=207.

Two vials each with a suspension of 5-nitro-2-methyl-benzo[d][1,3]oxazin-4-one (0.60 g, 2.91 mmol) and 3-amino-piperidine-2,6-dione hydrogen chloride (0.48 g, 2.91 mmol) in pyridine (15 mL) were heated at 170° C. for 10 minutes in a microwave oven. The suspension was filtered and washed with pyridine (5 mL). The filtrate was concentrated in vacuo. The resulting mixture was stirred in HCl (30 mL, 1N), ethyl acetate (15 mL) and ether (15 mL) for 2 hrs. The suspension was filtered and washed with water (30 mL) and ethyl acetate (30 mL) to give a dark brown solid, which was stirred with methanol (50 mL) at room temperature overnight. The suspension was filtered and washed with methanol to give 3-(2-methyl-5-nitro-4-oxo-4H-quinazolin-3-yl)-piperidine-2,6-dione as a black solid (490 mg, 27% yield). The solid was used in the next step without further purification.

A mixture of 3-(2-methyl-5-nitro-4-oxo-4H-quinazolin-3-yl)-piperidine-2,6-dione (250 mg) and Pd(OH)$_2$ on carbon (110 mg) in DMF (40 mL) was shaken under hydrogen (50 psi) for 12 hrs. The suspension was filtered through a pad of Celite and washed with DMF (10 mL). The filtrate was concentrated in vacuo and the resulting oil was purified by flash column chromatography (silica gel, methanol/methylene chloride) to give 3-(5-amino-2-methyl-4-oxo-4H-quinazolin-3-yl)-piperidine-2,6-dione as a white solid (156 mg, 69% yield): HPLC: Waters Symmetry C$_{18}$, 5 µm, 3.9×150 mm, 1 mL/min, 240 nm, 10/90 CH$_3$CN/0.1% H$_3$PO$_4$, 3.52 min (99.9%); mp: 293-295° C.; $^1$H NMR (DMSO-d$_6$) δ 2.10-2.17 (m, 1H, CHH), 2.53 (s, 3H, CH$_3$), 2.59-2.69 (m, 2H, CH$_2$), 2.76-2.89 (m, 1H, CHH), 5.14 (dd, J=6, 11 Hz, 1H, NCH), 6.56 (d, J=8 Hz, 1H, Ar), 6.59 (d, J=8 Hz, 1H, Ar), 7.02 (s, 2H, NH$_2$), 7.36 (t, J=8 Hz, 1H, Ar), 10.98 (s, 1H, NH); $^{13}$C NMR (DMSO-d$_6$) δ 20.98, 23.14, 30.52, 55.92, 104.15, 110.48, 111.37, 134.92, 148.17, 150.55, 153.62, 162.59, 169.65, 172.57; LCMS: MH=287; Anal. Calcd. for C$_{14}$H$_{14}$N$_4$O$_3$+0.3 H$_2$O: C, 57.65; H, 5.05; N, 19.21. Found: C, 57.50; H, 4.73; N, 19.00.

6.4 Preparation of 3-(4-((4-(morpholinomethyl)benzyl)-oxy)-1-oxoisoindolin-2-yl)piperidine-2,6-dione

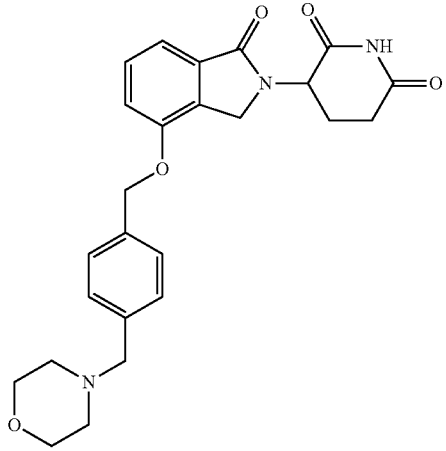 [SMILES: O=C1CCC(N2Cc3c(OCc4ccc(CN5CCOCC5)cc4)cccc3C2=O)C(=O)N1]

3-Hydroxy-2-methyl-benzoic acid methyl ester

3-Hydroxy-2-methylbenzoic acid (105 g, 690 mmol) was added to MeOH (800 mL) in a 2 L three neck round bottom flask equipped with condenser, thermometer and stirring bar followed by the addition of MeOH (250 mL). $H_2SO_4$ (10 mL, 180 mmol) was added to above solution. The reaction mixture was stirred at 62° C. for 17 hours. The solvent was removed in vacuo. The residue (200 mL) was added to water (600 mL) slowly at room temperature and a white solid was formed. The suspension was stirred in an ice bath for 30 minutes and filtered. The solid was washed with water (5×250 mL) and dried to give 3-hydroxy-2-methyl-benzoic acid methyl ester as a white solid (100 g, 87% yield). The compound was used in the next step without further purification: LCMS MH=167; $^1$H NMR (DMSO-$d_6$) δ 2.28 (s, 3H, $CH_3$), 3.80 (s, 3H, $CH_3$), 6.96-7.03 (m, 1H, Ar), 7.09 (t, J=7.8 Hz, 1H, Ar), 7.14-7.24 (m, 1H, Ar), 9.71 (s, 1H, OH).

3-(tert-Butyl-dimethyl-silanyloxy)-2-methyl-benzoic acid methyl ester

To a 1 L three neck RB flask equipped with stirring bar and thermometer, were added DMF (300 mL), methyl 3-hydroxy-2-methylbenzoate (90 g, 542 mmol) and imidazole (92 g, 1,354 mmol). TBDMS-Cl (90 g, 596 mmol) was added to the above solution in portions to control the internal temp between 15-19° C. over 20 minutes, and after addition, the internal temp dropped below 1° C. The ice bath was removed and the reaction mixture was stirred at room temperature for 16 hours. The reaction mixture was added to ice water (500 mL), and the resulting solution was divided into two portions (700 mL×2). Each portion was extracted with EtOAc (700 mL). Each organic layer was washed with cold water (350 mL) and brine (350 mL). Organic layers were combined and dried by $MgSO_4$. The combined organic layer was concentrated to give 3-(tert-butyl-dimethyl-silanyloxy)-2-methyl-benzoic acid methyl ester as a light brown oil (160 g, 100% crude yield). The compound was used in the next step without further purification: LCMS MH=281; $^1$H NMR (DMSO-$d_6$) δ −0.21 (s, 6H, $CH_3$, $CH_3$), 0.73-0.84 (m, 9H, $CH_3$, $CH_3$, $CH_3$), 2.10 (s, 3H, $CH_3$), 3.60 (s, 3H, $CH_3$), 6.82 (dd, 1H, Ar), 6.97 (t, J=7.9 Hz, 1H, Ar), 7.13 (dd, J=1.1, 7.7 Hz, 1H, Ar).

2-Bromomethyl-3-(tert-butyl-dimethyl-silanyloxy)-benzoic acid methyl ester

NBS (49.8 g, 280 mmol) was added to methyl 3-(tert-butyl dimethylsilyloxy)-2-methylbenzoate (78.4 g, 280 mmol) in methyl acetate (500 mL) at room temperature to give an orange colored suspension. The resulting reaction mixture was heated in an oil bath at 40° C. and shined by 300 wt sunlight bulb at reflux for 4 hours. The reaction mixture was cooled down and washed by $Na_2SO_3$ solution (2×600 mL, 50% saturated concentration), water (500 mL) and brine (600 mL). The organic layer was dried by $MgSO_4$ and decolorized by charcoal. The organic layer was concentrated to give 2-bromomethyl-3-(tert-butyl-dimethyl-silanyloxy)-benzoic acid methyl ester as a light brown oil (96 g, 91% crude yield). The compound was used in the next step without further purification: LCMS M-Br=279; $^1$H NMR (DMSO-$d_6$) δ 0.05-0.11 (m, 6H, $CH_3$, $CH_3$), 0.82 (s, 9H, $CH_3$, $CH_3$, $CH_3$), 3.65 (s, 3H, $CH_3$), 4.74 (s, 2H, $CH_2$), 6.94 (dd, J=1.3, 8.1 Hz, 1H, Ar), 7.10-7.20 (m, 1H, Ar), 7.21-7.29 (m, 1H, Ar).

4-Carbamoyl-butyric acid methyl ester

To a stirred solution of methyl 2-(bromomethyl)-3-(tert-butyldimethylsilyloxy)-benzoate (137.5 g, 325 mmol) in acetonitrile (1100 mL) in a 2 L round bottom flask, was added methyl 4,5-diamino-5-oxopentanoate hydrochloride (70.4 g, 358 mmol). To the suspension was added DIPEA (119 ml, 683 mmol) through an addition funnel over 10 minutes and the suspension was stirred at room temperature for 1 hour before the mixture was heated in an oil bath at 40° C. for 23 hours. The reaction mixture was concentrated under vacuo. The residue was stirred in ether (600 mL), and a white solid precipitated out. The mixture was filtered and the solid was washed with ether (400 mL). The filtrate was washed with HCl (1N, 200 mL), $NaHCO_3$ (sat. 200 mL) and brine (250 mL). The aqueous acid layer and basic layer were kept separately. Then the solid was further washed with ether (250 mL) and the liquid was washed with above acid solution and basic solution. The two organic layers were combined and concentrated under vacuo to give 4-[4-(tert-Butyl-dimethyl-silanyloxy)-1-oxo-1,3-dihydro-isoindol-2-yl]-4-carbamoyl-butyric acid methyl ester as a brown oil (152 g, 115% crude yield, 77% purity by H NMR). The compound was used in the next step without further purification: LCMS MH=407.

4-Carbamoyl-4-(4-hydroxy-1-oxo-1,3-dihydro-isoindol-2-yl)-butyric acid methyl ester To a stirred cold solution of methyl 5-amino-4-(4-(tert-butyldimethylsilyloxy)-1-oxoisoindolin-2-yl)-5-oxopentanoate (152 g, 288 mmol) in DMF (500 mL) and water (55 mL), was added by $K_2CO_3$ (19.89 g, 144 mmol) by portions over 5 minutes. The resulting reaction mixture was stirred at room temperature for 40 minutes. The reaction mixture was cooled in an ice bath. To the mixture, HCl (12M, 23.99 ml, 288 mmol) was added slowly. After the addition, acetonitrile (280 mL) was added to the mixture and a solid precipitated out. The mixture was stirred at room temperature for 10 minutes and filtered. The solid was washed with acetonitrile (50 mL×4). The filtrate was concentrated under high vacuo to give a yellow oil (168 g). The oil was dissolved in acetonitrile (600 mL) and stirred at room temperature for 10 minutes. The mixture was filtered and the solid was washed with acetonitrile (25 mL×2). The filtrate was concentrated under high vacuo to give a yellow oil (169 g), which was added to a mixture of water (1200 mL) and ether (1000 mL). The mixture was stirred for 3 minutes and the layers were separated. The aqueous solution was concentrated under high vacuo and the residue was stirred in acetonitrile (160 mL) and a white solid was formed after overnight stirring. The mixture was filtered to give 4-carbamoyl-4-(4-hydroxy-1-oxo-1,3-dihydro-isoindol-2-yl)-butyric acid methyl ester as a white solid (46 g, 54% yield). The filtrate was concentrated and the residue was further crystallized in acetonitrile (60 mL) to give more 4-carbamoyl-4-(4-hydroxy-1-oxo-1,3-dihydro-isoindol-2-yl)-butyric acid methyl ester as a white solid (11.7 g, 14% yield). The filtrate was concentrated and the residue was purified by ISCO chromatography to give more 4-carbamoyl-4-(4-hydroxy-1-oxo-1,3-dihydro-isoindol-2-yl)-butyric acid methyl ester as a white solid (13.2 g, 15% yield). The total product obtained was 70.9 g in 83% yield: LCMS MH=293; $^1$H NMR (DMSO-$d_6$) δ 1.95-2.34 (m, 4H, $CH_2$, $CH_2$), 3.51 (s, 3H, $CH_3$), 4.32 (d, J=17.6 Hz, 1H, CHH), 4.49 (d, J=17.4 Hz, 1H, CHH), 4.73 (dd, J=4.7, 10.2 Hz, 1H, CHH), 6.99 (dd, J=0.8, 7.9 Hz, 1H, Ar), 7.10-7.23 (m, 2H, Ar, NHH), 7.25-7.38 (m, 1H, Ar), 7.58 (s, 1H, NHH), 10.04 (s, 1H, OH).

3-(4-((4-(morpholinomethyl)benzyl)oxy)-1-oxoisoindolin-2-yl)piperidine-2,6-dione Step 1: To the solution of 3-(4-hydroxy-1-oxo-1,3-dihydro-isoindol-2-yl)-piperidine-2,6-dione (2.5 g, 8.56 mmol) in THF (60 mL) was added triphenyl phosphine (polymer supported 1.6 mmol/g, 12 g, 18.8 mmol). The mixture was stirred at room temperature for 15 minutes. Diisopropyl azodicarboxylate (3.96 mL, 18.8 mmol) was added at 0° C., and the mixture was stirred at 0° C. for 30 minutes. (4-Morpholin-4-ylmethyl-phenyl)-methanol (2.62 g, 12.4 mmol) was added at 0° C., and the mixture was allowed to warm to room temperature and stirred at room temperature overnight. The reaction mixture was filtered, and the filtrate was concentrated. The resulting oil was purified on silica gel column eluted with methylene chloride and methanol (gradient, product came out at 6% methanol) to give 4-carbamoyl-4-[4-(4-morpholin-4-ylmethyl-benzyloxy)-1-oxo-1,3-dihydro-isoindol-2-yl]-butyric acid methyl ester (2.2 g, 54% yield). The product was used in the next step without further purification.

Step 2: To the THF solution (50 mL) of 4-carbamoyl-4-[4-(4-morpholin-4-ylmethyl-benzyloxy)-1-oxo-1,3-dihydro-isoindol-2-yl]-butyric acid methyl ester (2.2 g, 4.57 mmol) was added potassium tert-butoxide (0.51 g, 4.57 mmol) at 0° C. The mixture was stirred at 0° C. for 10 minutes and was quenched with 1N HCl (5 mL, 5 mmol) followed by saturated $NaHCO_3$ (25 mL). The mixture was extracted with EtOAc (2×50 mL). The organic layer was washed with water (30 mL), brine (30 mL), dried over $MgSO_4$ and concentrated. To the resulting solid was added EtOAc (10 mL) followed by hexane (10 mL) under stirring. The suspension was filtered to give 3-(4-((4-(morpholinomethyl)benzyl)oxy)-1-oxoisoindolin-2-yl)piperidine-2,6-dione as white solid (1.5 g, 73% yield). HPLC: Waters Symmetry $C_{18}$, 5 μm, 3.9×150 mm, 1 mL/min, 240 nm, gradient to 95/5 acetonitrile/0.1% $H_3PO_4$ in 5 min: $t_R$=4.78 min (97.5%); mp: 210-212° C.; $^1$H NMR (DMSO-$d_6$) δ 1.86-2.09 (m, 1H, CHH), 2.29-2.38 (m, 4H, $CH_2$,$CH_2$), 2.44 (dd, J=4.3, 13.0 Hz, 1H, CHH), 2.53-2.64 (m, 1H, CHH), 2.82-2.99 (m, 1H, CHH), 3.46 (s, 2H, $CH_2$), 3.52-3.61 (m, 4H, $CH_2$,$CH_2$), 4.18-4.51 (m, 2H, $CH_2$), 5.11 (dd, J=5.0, 13.3 Hz, 1H, NCH), 5.22 (s, 2H, $CH_2$), 7.27-7.38 (m, 5H, Ar), 7.40-7.53 (m, 3H, Ar), 10.98 (s, 1H, NH) $^{13}$C NMR (DMSO-$d_6$) δ 22.36, 31.21, 45.09, 51.58, 53.14, 62.10, 66.17, 69.41, 114.97, 115.23, 127.64, 128.99, 129.81, 129.95, 133.31, 135.29, 137.68, 153.50, 168.01, 170.98, 172.83; LCMS: 465; Anal Calcd for $C_{25}H_{27}N_3O_5$+0.86 $H_2O$: C, 64.58; H, 6.23; N, 9.04. Found: C, 64.77; H, 6.24; N, 8.88.

The compounds (S)-3-(4-((4-(morpholinomethyl)benzyl)oxy)-1-oxoisoindolin-2-yl)piperidine-2,6-dione and (R)-3-(4-((4-(morpholinomethyl)benzyl)oxy)-1-oxoisoindolin-2-yl)piperidine-2,6-dione were prepared from 3-(4-((4-(morpholinomethyl)benzyl)oxy)-1-oxoisoindolin-2-yl)piperidine-2,6-dione through chiral separation.

6.5 3-(1-oxo-4-(4-(2-(pyrrolidin-1-yl)ethoxy) benzyloxy)isoindolin-2-yl)-piperidine-2,6-dione

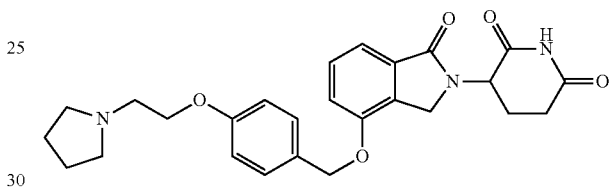

Step 1: A mixture of 4-hydroxybenzaldehyde (4.0 g, 32.8 mmol) and $Cs_2CO_3$ (26.7 g, 81.9 mmol) in DMF (80 mL) was stirred for 10 minutes at room temperature. To this mixture, was added 1-(2-chloroethyl)pyrrolidine hydrochloride (6.7 g, 39.3 mmol). The mixture was warmed at 60° C. for 2 hours then at 80° C. overnight. The reaction mixture was cooled and filtered, and the solid was washed with EtOAc (100 mL). The filtrate was stirred with cold water (200 mL) and the aqueous layer was extracted with EtOAC (3×50 mL). The combined EtOAc solutions was washed with 2N NaOH (40 mL), water (3×40 mL) and brine (40 mL) and dried ($K_2CO_3$). The solvent was removed to give 4-(2-pyrrolidin-1-yl-ethoxy)benzaldehyde (5.9 g, 81% yield): $^1$H NMR ($CDCl_3$) δ 1.76-1.84 (m, 4H), 2.60-2.65 (m, 4H), 2.91-2.95 (m, 2H), 4.19 (t, J=6.0 Hz, 2H), 7.00-7.04 (m, 2H), 7.80-7.95 (m, 2H), 9.88 (s, 1H).

Step 2: A solution of 4-(2-pyrrolidin-1-yl-ethoxy)benzaldehyde (5.8 g, 26.5 mmol) in reagent alcohol (60 mL) was cooled to −60° C. in dry ice/acetone bath. LiBH4/THF (2M, 15.9 mL, 31.9 mmol) was added slowly at −60° C. The mixture was stirred at −60° C. for 1 hour. The reaction mixture was quenched with water (20 mL) slowly and then warmed to room temperature. The mixture was concentrated and the residue was stirred with EtOAc (80 mL) and 2N NaOH (20 mL). The aqueous layer was extracted with EtOAc (2×30 mL), and the combined EtOAc solutions was washed with water (30 mL) and brine (30 mL) and dried. The solvent was removed and the residue was purified by chromatography ($SiO_2$, $NH_4OH$:$CH_3OH$:$CH_2Cl_2$ 0.5:3:97) to give 4-[(2-pyrrolidin-1-yl-ethoxy)-phenyl]-methanol (2.5 g, 42% yield): $^1$H NMR ($CDCl_3$) δ 1.74-1.83 (m, 4H), 2.56-2.63 (m, 4H), 2.86 (t, J=6.1 Hz, 2H), 4.03 (t, J=6.0 Hz, 2H), 4.57 (s, 2H), 6.82-6.87 (m, 2H), 7.23-7.27 (m, 2H).

Step 3: Diisopropyl azodicarboxylate (1.1 g, 5.5 mmol) was added slowly to a stirred suspension of methyl 5-amino-4-(4-hydroxy-1-oxoisoindolin-2-yl)-5-oxopentanoate (0.8 g, 2.7 mmol), 4-[(2-pyrrolidin-1-yl-ethoxy)-phenyl]-methanol (0.9 g, 4.1 mmol) and triphenylphosphine-polymer bound (1.8 g, 5.5 mmol) in THF (60 mL) at 5-8° C. After addition, the mixture was stirred at room temperature overnight. The reaction mixture was filtered and the solid was washed with $CH_2Cl_2$ (30 mL). The filtrate was concentrated and the residue was purified by chromatography ($SiO_2$, $CH_3OH$: $CH_2Cl_2$=3:97) to give methyl 5-amino-5-oxo-4-(1-oxo-4-(4-(2-pyrrolidin-1-yl)ethoxy)benzyloxy)isoindolin-2-yl) pentanoate (1.0 g, 77%).

Step 4: A solution of KO-t-Bu/THF (1M, 2.5 mL, 2.5 mmol) was added slowly to a stirred solution of methyl 5-amino-5-oxo-4-(1-oxo-4-(4-(2-pyrrolidin-1-yl)ethoxy) benzyloxy)isoindolin-2-yl)pentanoate (1.0 g, 2.1 mmol) in THF (30 mL) at 5° C. The mixture was stirred at 5° C. for 10 minutes then warmed to room temperature for 2 hours. The reaction mixture was cooled in an ice bath and quenched with 4N HCl (4 mL). The mixture was stirred with EtOAc (40 mL) and sat $Na_2CO_3$ (25 mL). The aqueous layer was extracted with EtOAc (3×40 mL) and combined EtOAc solution was washed with water (40 mL) and brine (40 mL) and dried ($K_2CO_3$). The solvent was removed and the residue was purified by chromatography ($SiO_2$, $CH_3OH$: $CH_2Cl_2$=5:95) to give 3-(1-oxo-4-(4-(2-pyrrolidin-1-yl) ethoxy)-benzyloxy)isoindolin-2-yl)piperidine-2,6-dione (0.2 g, 20% yield): mp 153-155° C.; 1H NMR (DMSO-d6) δ 1.66-1.69 (m, 4H), 1.94-1.99 (m, 1H), 2.40-2.59 (m, 2H), 2.77 (t, J=5.7 Hz, 2H), 2.84-2.90 (m, 1H), 4.06 (t, J=6.0 Hz, 2H), 4.24 (d, J=17.4 Hz, 1H), 4.35 (d, J=17.7 Hz, 1H), 5.07-5.13 (dd, J=5.1 and 13.2 Hz, 1H), 5.15 (s, 2H), 6.92-6.97 (m, 2H), 7.30-7.50 (m, 5H), 10.96 (s, 1H); 13C NMR (DMSO-d6) δ 22.33, 23.09, 31.17, 45.06, 51.54, 53.93, 54.24, 66.69, 69.34, 114.35, 115.04, 115.12, 128.42, 129.50, 129.75, 129.95, 133.25, 153.50, 158.33, 168.00, 170.96, 172.81; Calcd for $C_{26}H_{29}N_3O_5$+0.5 Et2O: C, 66.65; H, 6.63; N, 8.64. Found: C, 66.95; H, 6.62; N, 8.71.

6.6 3-(4-(4-(2-morpholin-4-yl-ethoxy)-benzyloxy)-1-oxoisoindolin-2-yl)-piperidine-2,6-dione

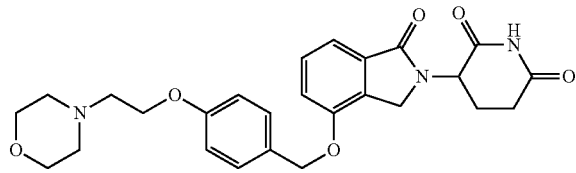 [SMILES: O=C1CCC(N2Cc3c(OCc4ccc(OCCN5CCOCC5)cc4)cccc3C2=O)C(=O)N1]

Step 1: A mixture of 4-hydroxybenzaldehyde (4.0 g, 32.8 mmol) and $Cs_2CO_3$ (26.7 g, 81.9 mmol) in DMF (80 mL) was stirred at room temperature for 10 minutes. To this mixture was added 4-(2-chloroethyl)morpholine hydrochloride (7.3 g, 39.3 mmol). The resulting mixture was heated at 80° C. in an oil bath overnight. The reaction mixture was cooled to room temperature and filtered, and the solid was washed with EtOAc (100 mL). Filtrate was diluted with cold water (200 mL) and aqueous layer was extracted with EtOAc (3×50 mL). Combined EtOAc solution was washed with 2N NaOH (25 mL), water (3×40 mL) and brine (40 mL), and dried ($K_2CO_3$). The solvent was removed to give 4-(2-morpholin-4-yl-ethoxy)-benzaldehyde (6.2 g, 81% yield): $^1$H NMR ($CDCl_3$) δ 2.57-2.60 (m, 4H), 2.83 (t, J=5.7 Hz, 2H), 3.70-3.75 (m, 4H), 4.19 (t, J=5.7 Hz, 2H), 6.98-7.03 (m, 2H), 7.81-7.85 (m, 2H), 9.88 (s, 1H); $^{13}$C NMR ($CDCl_3$) δ 53.52, 56.73, 65.77, 66.11, 114.93, 129.58, 131.73, 163.40, 191.21.

Step 2: $LiBH_4$/THF (2M, 15.9 mL, 31.7 mmol) was added slowly to a stirred solution of 4-(2-morpholin-4-yl-ethoxy)-benzaldehyde (6.2 g, 26.4 mmol) in reagent alcohol (60 mL) at −60° C. The resulting mixture was stirred at −60° C. for 1 hour then quenched with water (20 mL). The mixture was concentrated and the residue was stirred with EtOAc (80 mL) and 1N NaOH (30 mL). The aqueous layer was extracted with EtOAc (2×30 mL) and combined EtOAc solution was washed with water (40 mL) and brine (40 mL) and dried. The solvent was removed and the residue was purified by chromatography ($SiO_2$, $NH_4OH$:$CH_3OH$: $CH_2Cl_2$ 0.5:3:100) to give [4-(2-morpholin-4-yl-ethoxy)-phenyl]-methanol (4.2 g, 67% yield): $^1$H NMR ($CDCl_3$) δ 2.25 (s, 1H), 2.54-2.57 (m, 4H), 2.78 (t, J=5.7 Hz, 2H), 3.70-3.73 (m, 4H), 4.08 (t, J=5.7 Hz, 2H), 4.59 (s, 2H), 6.85-6.89 (m, 2H), 7.25-7.29 (m, 2H); $^{13}$C NMR ($CDCl_3$) δ 54.06, 57.61, 65.79, 66.85, 114.62, 128.57, 133.52, 158.24.

Step 3: Triphenylphosphine-polymer bound (1.8 g, 5.5 mmol) was stirred with dry $CH_2Cl_2$ (20 mL) for 10 minutes. To this mixture was added a solution of methyl 5-amino-4-(4-hydroxy-1-oxoisoindolin-2-yl)-5-oxopentanoate (0.8 g, 2.7 mmol) and [4-(2-morpholin-4-yl-ethoxy)-phenyl]-methanol (1.0 g, 4.1 mmol) in THF (60 mL). The resulting mixture was cooled to 5° C. and diisopropyl azodicarboxylate (1.1 g, 5.5 mmol) was added slowly at 5-8° C. After addition, the mixture was stirred at room temperature overnight. The reaction mixture was filtered and solid was washed with $CH_2Cl_2$ (30 mL). Filtrate was concentrated and the residue was purified by chromatography ($SiO_2$, $CH_3OH$: $CH_2Cl_2$ 3:97) to give methyl 5-amino-4-(4-(4-(2-morpholinoethoxyl)benzyloxy)-1-oxoisoindolin-2-yl)-5-oxo-pentanoate (1.0 g, 71%).

Step 4: A solution of potassium t-butoxide/THF (1M, 2.6 mL, 2.6 mmol) was added slowly at 5° C. to a stirred solution of methyl 5-amino-4-(4-(4-(2-morpholinoethoxyl) benzyloxy)-1-oxoisoindolin-2-yl)-5-oxopentanoate (1.1 g, 2.1 mmol) in THF (30 mL). The reaction mixture was stirred at 5° C. for 10 minutes then warmed to room temperature for 2 hours. The reaction mixture was cooled in an ice bath and quenched with 4N HCl (4 mL). The mixture was stirred with EtOAc (40 mL) and sat. $Na_2CO_3$ (25 mL). The aqueous layer was extracted with EtOAc (3×40 mL) and combined EtOAc solution was washed with water (40 mL) and brine (40 mL), and dried ($K_2CO_3$). The solvent was removed and the residue was purified by chromatography ($Al_2O_3$, $CH_3OH$: $CH_2Cl_2$ 3:97) to 3-(4-(4-(2-morpholinoethoxy)-benzyloxy)-1-oxoisoindolin-2-yl)-piperidine-2,6-dione (0.2 g, 16% yield): mp: 203-205° C.; $^1$H NMR (DMSO-$d_6$) δ 1.90-2.05 (m, 1H), 2.40-2.70 (m, 8H), 2.84-2.96 (m, 1H), 3.55-3.58 (m, 4H), 4.06-4.10 (m, 2H), 4.24 (d, J=17.4 Hz, 1H), 4.35 (d, J=17.4 Hz, 1H), 5.07-5.15 (m, 3H), 6.97 (d, J=8.4 Hz, 2H), 7.30-7.50 (m, 5H), 10.96 (s, 1H); $^{13}$C NMR (DMSO-$d_6$) δ 22.32, 31.17, 45.06, 51.55, 53.56, 56.92, 65.29, 66.11, 63.31, 114.41, 115.04, 115.11, 128.50, 129.47, 129.74, 129.94, 133.25, 153.49, 158.27, 167.99, 170.94, 172.80; Calcd for $C_{26}H_{29}N_3O_6$+0.2 $H_2O$: C, 64.64; H, 6.10; N, 8.70. Found: C, 64.54; H, 6.06; N, 8.63.

6.7 3-{4-[4-(2-morpholin-4-yl-ethyl)-benzyloxy]-1-oxo-1,3-dihydro-isoindol-2-yl}-piperidine-2,6-dione

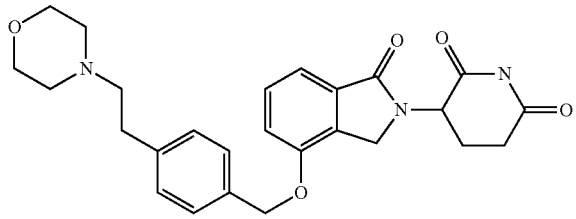 [SMILES: O=C1CCC(N2Cc3c(OCc4ccc(CCN5CCOCC5)cc4)cccc3C2=O)C(=O)N1]

Step 1: To the THF solution of 4-(2-bromoethyl)benzoic acid (25 g, 109 mmol) and trifluoroborane etherate (13.71 ml, 109 mmol), was added borane (196 ml, 196 mmol) dropwise through a dripping funnel at 0° C. during 2 hours. The mixture was stirred at room temperature overnight, and MeOH was added dropwise at room temperature until the cloudy suspension become clear and no more bubbles formed. The clear solution was concentrated on rota-yap and the resulting solid was stirred in water (100 mL) for 30 minutes at room temperature. The suspension was filtered to give 4-(2-chloro-ethyl)-benzoic acid as white solid (25 g, 107%).

Step 2: To the acetonitrile solution of (4-(2-bromoethyl)phenyl)methanol (25 g, 116 mmol), was added morpholine (25.3 ml, 291 mmol). NaI was added all at once. The mixture was stirred at room temperature over-weekend. The reaction suspension was filtered. The filtrate was concentrated and stirred in ether (100 mL) at room temperature for 30 minutes. The suspension was filtered. The resulting solid was dissolved in 1N HCl and was extracted with EtOAc (50 mL×2). The aqueous layer was neutralized with 1N NaOH to pH=7-8. The resulting suspension was filtered to give [4-(2-morpholin-4-yl-ethyl)-phenyl]-methanol as white solid (13 g, 60%).

Step 3: To the THF solution of 4-carbamoyl-4-(4-hydroxy-1-oxo-1,3-dihydro-isoindol-2-yl)-butyric acid methyl ester (0.5 g, 1.7 mmol), was added triphenyl phosphine resin (2.3 g, 1.6 mmol/g loading, 3.74 mmol) and DIAD (0.73 mL, 3.74 mmol) at 0° C. After being stirred at 0° C. for 10 minutes, the mixture was added [4-(2-morpholin-4-yl-ethyl)-phenyl]-methanol (0.65 g, 2.94 mmol) and was stirred at room temperature overnight. The mixture was filtered and the filtrate was concentrated and extracted with EtOAc (30 mL) and Na2CO3 (20 mL). The organic layer was washed with water (20 mL) and brine (20 mL), and concentrated. The resulting oil was purified on silica gel column to give 4-carbamoyl-4-{4-[4-(2-morpholin-4-yl-ethyl)-benzyloxy]-1-oxo-1,3-dihydro-isoindol-2-yl}-butyric acid methyl ester as white solid (0.74 g, 88%).

Step 4: To the THF solution (20 mL) of 4-carbamoyl-4-{4-[4-(2-morpholin-4-yl-ethyl)-benzyloxy]-1-oxo-1,3-dihydro-isoindol-2-yl}-butyric acid methyl ester (0.74 g, 1.5 mmol) was added potassium t-butoxide (0.16 g, 1.5 mmol) at 0° C. The mixture was stirred for 15 minutes at 0° C. and quenched with 5 mL of 1N HCl solution followed by 15 mL of saturated NaHCO3 solution. The mixture was extracted with EtOAc (20 mL). The organic layer was concentrated in vacuo. The resulting oil was purified on silica gel column eluted with $CH_2Cl_2$ and methanol to give 3-{4-[4-(2-morpholin-4-yl-ethyl)-benzyloxy]-1-oxo-1,3-dihydro-isoindol-2-yl}-piperidine-2,6-dione as a white solid (620 mg, 87% yield): mp: 230-232° C. HPLC: Waters Symmetry C-18, 3.9×150 mm, 5 micro, 1 mL/min, 240 nm, gradient acetonitrile/0.1% $H_3PO_4$ in $H_2O$ from 5/95 to 100/0 in 5 min and stayed at 100/0 for 5 min: $t_R$=4.86 min (97%); $^1$H NMR (DMSO-$d_6$) δ 1.80-2.12 (m, 1H, CHH), 2.40-2.44 (m, 4H, $CH_2,CH_2$), 2.45-2.48 (m, 1H, CHH), 2.55-2.64 (m, 1H, CHH), 2.69-2.80 (m, 2H, $CH_2$), 2.81-3.00 (m, 1H, CHH), 3.52-3.61 (m, 4H, $CH_2$, $CH_2$), 4.18-4.48 (m, 2H, $CH_2$), 5.11 (dd, J=5.1, 13.2 Hz, 1H, NCH), 5.20 (s, 2H, $CH_2$), 7.19-7.54 (m, 7H, Ar), 10.97 (s, 1H, NH); $^{13}$C NMR (DMSO-$d_6$) δ 22.36, 31.21, 32.04, 45.10, 51.58, 53.21, 59.93, 66.13, 69.47, 114.98, 115.19, 127.80, 128.70, 128.74, 129.79, 129.95, 133.29, 134.08, 140.25, 153.50, 168.01, 170.96, 172.82; LCMS MH=464; Anal Calcd for $C_{26}H_{29}N_3O_5$+0.5 $H_2O$: C, 66.09; H, 6.40; N, 8.89. Found: C, 65.96; H, 6.33; N, 9.07.

6.8 Assays

6.8.1 Cytokine Production by T Cells

T cells were isolated from buffy coat by negative selection using the RosetteSep® T Cell Enrichment Cocktail. The manufacturer's procedures were followed accordingly. All 96-well plates were pre-coated with 3 μg/ml anti-human CD3 antibody in 100 μl 1×PBS for 4 hours at 37° C. The plates were washed three times with RPMI-1640 Complete Media prior to the T cell assay. T cells were then plated in CD3 pre-coated plates at a density of 2.5×10$^5$ cells/well in 180 μl RPMI-1640 Complete Media. The cells were treated with 20 μl 10× titrated compounds at 10, 1, 0.1, 0.01, 0.001, 0.0001 and 0.00001 μM. Final DMSO concentrations were 0.25%. The plates were incubated for 48 hours at 37° C., 5% $CO_2$. After 48 hours, the supernatants were harvested and tested by a multi-plex cytmteric bead array (CBA) assay for the following cytokines/chemokines: IL-2, IL-3, IL-5, IL-10, IL-13, IL-15, IL-17a, GM-CSF, G-SCF, IFN-γ, TNF-α and RANTES. The CBA plates were analyzed on the Luminex IS 100 instrument. Data from donors were graphed using GraphPad Prism 5.0 software and expressed as mean pg/mL±SEM and % of DMSO control±SEM.

Cytokine levels were normalized to the amount produced in the presence of the amount of a compound tested, and $EC_{50}$ values were calculated using non-linear regression, sigmoidal dose-response, constraining the top to 100% and bottom to 0%, allowing variable slope (GraphPad Prism v3.02).

Anti-CD3-Stimulated Human T Cell Assay

All 96-well plates were pre-coated with 3 μg/mL anti-human CD3 antibody in 100 μL 1×PBS for 4 hours at 37° C. The plates were washed 3 times with RPMI-1640 Complete Media prior to the T cell assay. The T cells were then plated in anti-CD3-pre-coated plates at a density of 2.5×105 cells/well in 180 μL RPMI-1640 Complete Media. The cells were treated with 20 μL 10× titrated Celgene compounds at 10, 1, 0.1, 0.01, 0.001, 0.0001, and 0.00001 μM in duplicate. The final DMSO concentrations were 0.25%. The plates were incubated for 48 hours at 37° C., 5% CO2. After 48 hours, the supernatants were harvested and tested by a multiplex cytometric bead array (CBA) assay for the following cytokines/chemokines: IL-2, IL-3, IL-5, IL-10, IL-13, IL-15, IL-17A, GM-CSF, G-CSF, IFN-γ, TNF-α, and RANTES. The CBA plates were analyzed on the Luminex IS 100 instrument.

6.8.2 Western Blot Analysis

Cell lines were maintained using standard cell culture techniques. For endogenous Aiolos expression, cells were seeded in a 6 well plate at 0.5e6 cells per well in a 3 mL volume of media. Cells were allowed to adhere to the plate overnight. Cells were exposed to 0, 1, and 10 uM CC-122 for 0-24 hours or 5 days.

In some experiments, cell lines were transfected with an Aiolos overexpression vector using Lipofectamine reagent in a batch method. Cells were seeded in a 12 well plate at 1e5 cells in a 3 mL volume per well. As specified, cells were pretreated with MG132 at 10 uM for 1 h or DMSO was added as a control. Following the pretreatment, CC-122 was added directly to the cell culture media at the specified concentration.

Cells were harvested and lysed in Pierce #89900 Ripa buffer containing 2× protease inhibitor cocktail from Pierce #78442. The lysate was applied to a QiaShredder to remove DNA. Total protein yield was measured using Bio Rad DC protein determination kit (Cat#500-0112).

Samples were applied to BioRad Criterion PreCast gels, 10% (Bio-Rad#345-0010) and transferred to Bio-Rad Nitrocellulose/Filter Paper Sandwiches #162-0233. 0233 and Aiolos protein expression was measured with an Aiolos antibody and read on a LiCor instrument.

6.8.3 Conjugation and Testing of Aiolos Antibody

This example demonstrates the conjugation of the Aiolos antibodies with Alexa Fluor 647 used in certain embodiments of the methods provided herein and the testing of the conjugated antibodies. Briefly, Aiolos 0-21 rabbit polyclonal antibodies (SantaCruz Cat# sc-101982) or other suitable poly or monoclonal antibodies are directly conjugated to Alexa Fluor 647 and then tested for specificity on a positive (peripheral blood) and negative control cell line. The cells are fixed by BD Lyse/Fix followed by BD Perm Buffer I. The specificity of the antibodies is performed with and without testing compounds.

First, 100 µg of purified antibodies are conjugated with 5 molar excess (ME) and 10 ME of Alexa Fluor 647 to determine the optimal conjugation conditions. Post-conjugation specificity is determined by incubating 0.5 µg of each test conjugate and purified antibody with a specific peptide blocker separately. Normal whole blood cells (positive control) and HEK-293 cells (negative control) are processed and stained with the conjugated and purified antibodies (with and without blockers) separately. Purified reagents are developed with appropriate anti-species Alexa Fluor 647 secondary. Signal to noise ratio and the specific fluorescence percentage are determined. If the signal to noise ratio and the specific fluorescence percentage for the conjugated antibodies and purified antibodies are comparable, then the optimal molar ratio of fluorescent dye and antibody is determined. The reminder of the purified antibodies are conjugated at the optimal molar ratio. Complete titration of conjugated antibodies for saturation determination is performed on normal whole blood cells treated or untreated with testing compounds.

6.8.4 Fixation Determination for Cells

Purpose:

To determine an optimum method for detection of all markers of interest while maintaining surface marker expression in PBMCs. PBMCs or fresh normal donor whole blood are treated with either a carrier control or a compound provided herein at 1 micromolar for 2 hours and then processed below. Untreated MM-BMMCs are also used.

Frozen PBMCs (control and treated), fresh normal donor whole blood (control and treated), and frozen MM-BMMCs (untreated only) are thawed and then fixed by one of following fixation/permeabilization methods: (1) BD Lyse/Fix+Perm Buffer I; (2) BD Lyse/Fix+Perm Buffer II; or (3) Esoterix Proprietary fixative.

6.8.5 Assay Stability

The stability of fresh normal donor whole blood samples is examined. Five (5) normal donor whole blood samples (basal expression only) are drawn and fixed by the method determined by the previous example. The fixed samples are split into two aliquots.

One aliquot is placed at 4° C. at 1 hour and another placed at −20° C. for 1 hour. These samples are tested immediately (Day 0). Remaining aliquots are stored at 4° C. or −20° C. and tested on 1 day ex-vivo, 2 days ex-vivo and 3 days ex-vivo.

The samples are tested for biological variability by analysis of the basal difference of Aiolos in normal whole blood from 5 different donors.

6.8.6 Intra-Assay Reproducibility and Inter-Operator Precision

To determine the repeatability of the assays, the same 5-NWB samples tested for stability from above are tested in triplicate at one time point. These samples were tested in triplicate in the Day 0, 4° C. prepped samples. To test the Inter-operator precision, the same samples are processed by a second operator on the same day. The analysis includes Aiolos quantitative expression levels in CD19+a,CD3+ and total CD45+Lymphocyte population and in (reported in MEFL). The Mean, Standard Deviation and % CV are calculated between replicates and between operators.

6.8.7 Aiolos Determination by FACS Analysis in Cell Lines

This Example demonstrates the determination of Aiolos in cell lines and PBMCs using FACS analysis.

Materials:

BD Fix buffer I (cat#55870); BD Perm Buffer III (cat#558050); BD Stain Buffer (cat#554657); Anti-IKZF3 antibody (Santa Cruz lot # B1612) and secondary antibody (BD FITC Goat Anti-Rabbit Ig cat#554020).

Assay Procedure

The Fix buffer I was warmed up to 37° C. in an incubator or water bath prior to use. The Perm Buffer III was chilled in a −20° C. freezer prior to use. The cells were collected at the end of treatment with testing compounds. One volume of the pre-warmed Fix Buffer I was mixed with one volume of cell suspension. If the volume of the cell suspension is greater than 100 µL, the cells were spun and resuspended in 100 µL medium or PBS. The buffer and the cell suspension were mixed well and incubated in a 37° C. water bath for 10 min. The cells were spun down at 250×g for 10 min and the supernatant was aspirated. The cells were washed once with BD Stain Buffer. The pellet was spun and the supernatant was removed. The cells were vortexed to be loosened, and permeabilized by slowly adding cold Perm Buffer III while vortexing or mixing. Subsequently, the cells were incubated on ice for 30 min. The cells were then spun down and washed twice with Stain Buffer. The supernatant was spun and aspirated. The cells were resuspended in a small volume of Stain buffer (50 or 100 µL containing from 200,000 to 1 million cells). Anti-IKFZ3 antibody was added to the cell suspension at 1:1000 dilution and incubated for 45 min at 4° C. The cells were then spun down and washed once with stain buffer. Secondary antibody was added to the cells at 1:5000 dilution and incubated at room temperature for 20 min in the dark. The cells were washed once with stain buffer prior to analysis by FACS.

6.9 Results

The inhibitory effects of the test compounds (lenalidomide, pomalidomide, thalidomide, Compound A, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl)-piperidine-2,6-dione) on lipopolysaccharide (LPS)-stimulated human peripheral blood mononuclear cells (hPBMC) cytokine/chemokine production demonstrated that the test compounds inhibit IL-6, IL-8, IL-1β, GM-CSF, MDC, MIP-1α, MIP-1β, and TNF-α production with varied potencies (Table 1). The data also demonstrates that the test compounds are effective at enhancing IL-10, MCP-1, and RANTES production (Table 2). Data provided are $IC_{50}$ (μM) values for the indicated cytokines

TABLE 2

| Cytokine Profile Summary of Test Compounds | | | |
|---|---|---|---|
| Test Compounds | IL-10 (% of control) | MCP-1 (% of control) | RANTES (% of control) |
| 3-(4-((4-(morpholinomethyl)benzyl)oxy)-1-oxoisoindolin-2-yl)piperidine-2,6-dione | 372 | 208 | 153 |
| (R)-3-(4-((4-(morpholinomethyl)benzyl)oxy)-1-oxoisoindolin-2-yl)piperidine-2,6-dione | 442 | 223 | 151 |
| (S)-3-(4-((4-(morpholinomethyl)benzyl)oxy)-1-oxoisoindolin-2-yl)piperidine-2,6-dione | 379 | 233 | 153 |
| Compound A | 480 | 236 | 131 |
| thalidomide | 170 | 138 | 89 |
| pomalidomide | 684 | 301 | 148 |
| lenalidomide | 540 | 312 | 121 |

6.9.1 Effects on Aiolos Expression

Figure 2:
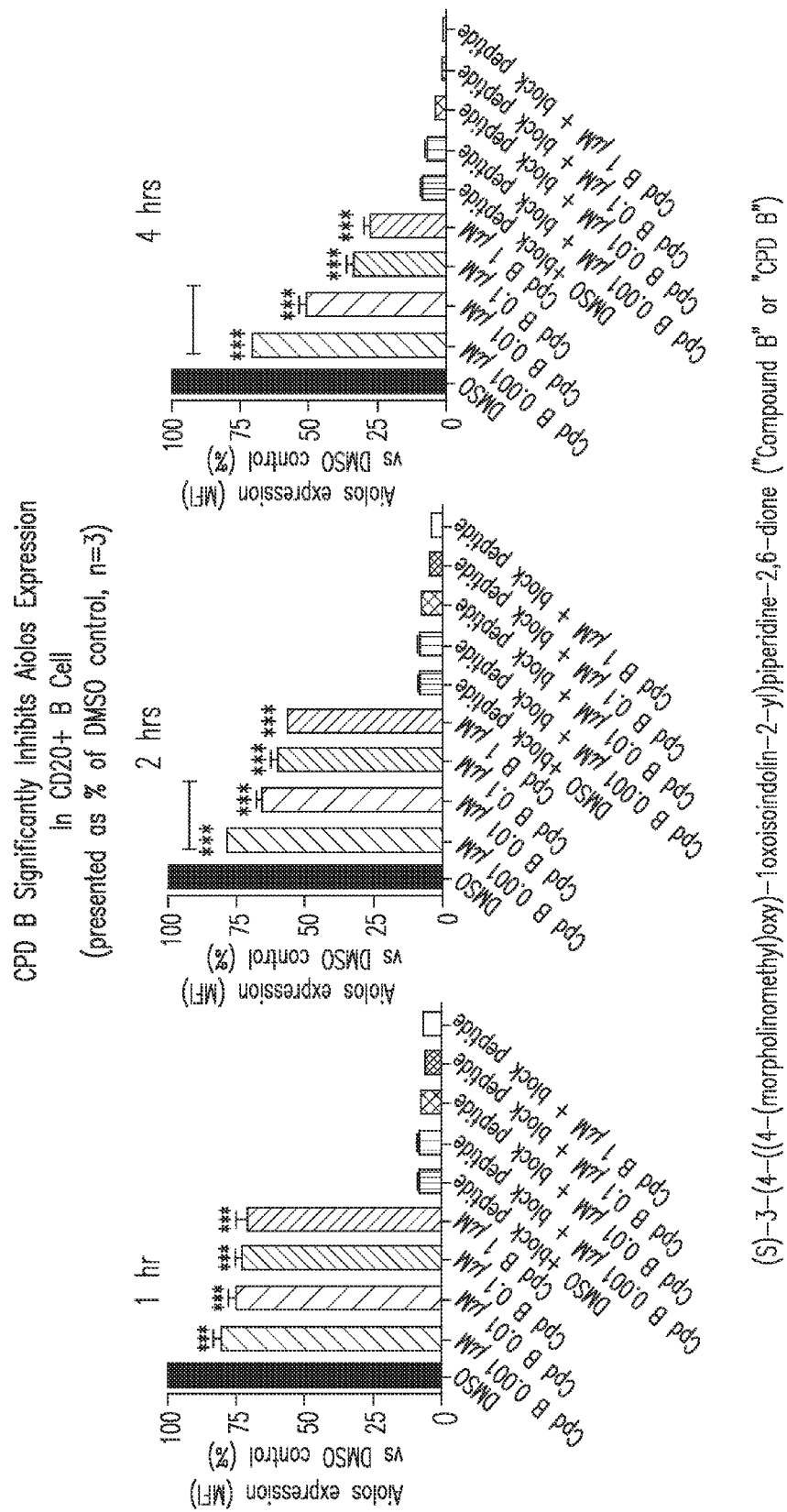
FIG. 2 illustrates the effect of Compound B on inhibition of Aiolos expression in CD20+ B Cells.
Figure 2:
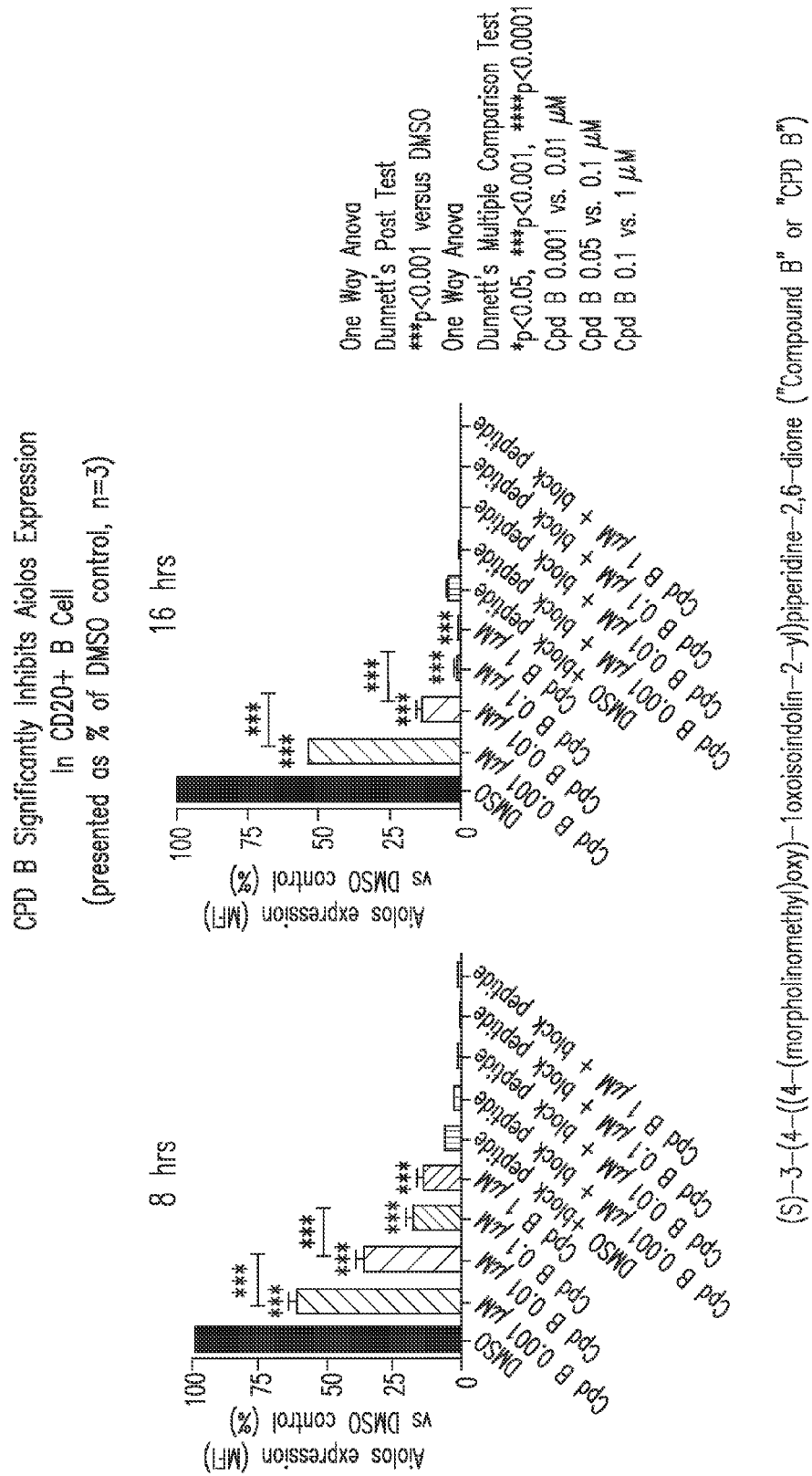
Figure 3:
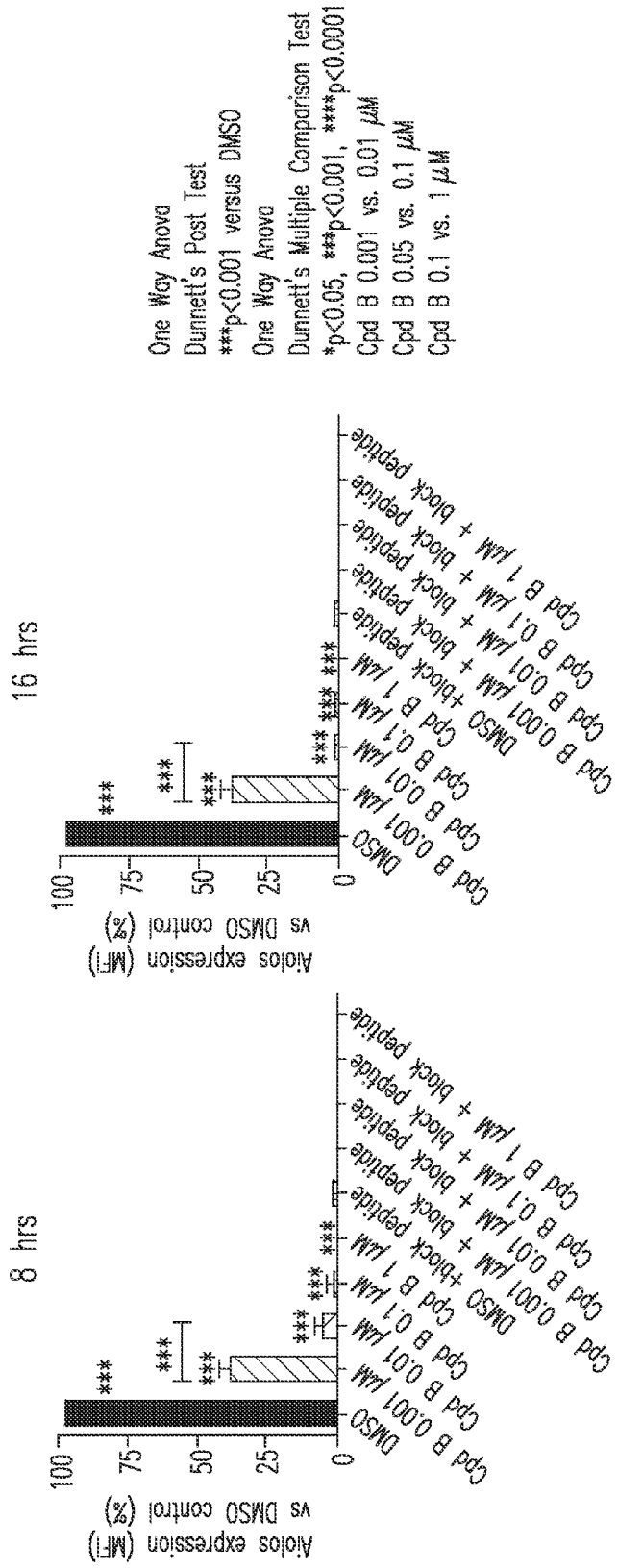
FIG. 3 illustrates the effect of Compound B on inhibition of Aiolos expression in CD3+ T Cells.

The effect of (S)-3-(4-((4-(morpholinomethyl)benzyl)oxy)-1-oxoisoindolin-2-yl)piperidine-2,6-dione in the inhibition of Aiolos expression in lymphocyte (left panel) granulocyte (top panel) and monocyte (right panel) is shown in FIG. 1. As shown in FIGS. 2 and 3, respectively, (S)-3-(4-

TABLE 1

| Summary of Cytokine Inhibitory Profile of Test Compounds | | | | | | | | |
|---|---|---|---|---|---|---|---|---|
| Compound | IL-6 | IL-8 | IL-1β | GM-CSF | MDC | MIP-1α | MIP-1β | TNF-α |
| 3-(4-((4-(morpholinomethyl)benzyl)oxy)-1-oxoisoindolin-2-yl)piperidine-2,6-dione | 0.01 | >10 | 0.00085 | 0.0092 | 0.0026 | 0.19 | >10 | 0.0018 |
| (R)-3-(4-((4-(morpholinomethyl)benzyl)oxy)-1-oxoisoindolin-2-yl)piperidine-2,6-dione | 0.083 | >10 | 0.0062 | 0.039 | 0.012 | 0.45 | >10 | 0.0095 |
| (S)-3-(4-((4-(morpholinomethyl)benzyl)oxy)-1-oxoisoindolin-2-yl)piperidine-2,6-dione | 0.0038 | >10 | 0.00046 | 0.0022 | 0.0021 | 0.028 | >10 | 0.00059 |
| Compound A | 0.060 | >10 | 0.054 | 0.95 | 0.062 | 0.3 | >10 | 0.034 |
| thalidomide | >10 | >10 | >10 | >10 | >10 | >10 | >10 | >10 |
| pomalidomide | 0.059 | 2.9 | 0.047 | 1.5 | 0.031 | 0.23 | >10 | 0.033 |
| lenalidomide | 1.2 | >10 | 0.39 | >10 | 0.19 | >10 | >10 | 0.22 |
| 3-(1-oxo-4-(4-(2-(pyrrolidin-1-yl)ethoxy)benzyloxy)isoindolin-2-yl)-piperidine-2,6-dion | | | | | | | | 0.00052 |
| 3-(4-(4-(2-morpholin-4-yl-ethoxy)-benzyloxy)-1-oxoisoindolin-2-yl)-piperidine-2,6-dione | | | | | | | | 0.00096 |
| 3-{4-[4-(2-morpholin-4-yl-ethyl)-benzyloxy]-1-oxo-1,3-dihydro-isoindol-2-yl}-piperidine-2,6-dione | | | | | | | | 0.00079 |

((4-(morpholinomethyl)benzyl)oxy)-1-oxoisoindolin-2-yl)
piperidine-2,6-dione significantly inhibited Aiolos expression in CD20+ B cells and CD3+ T cells.

Figure 4:
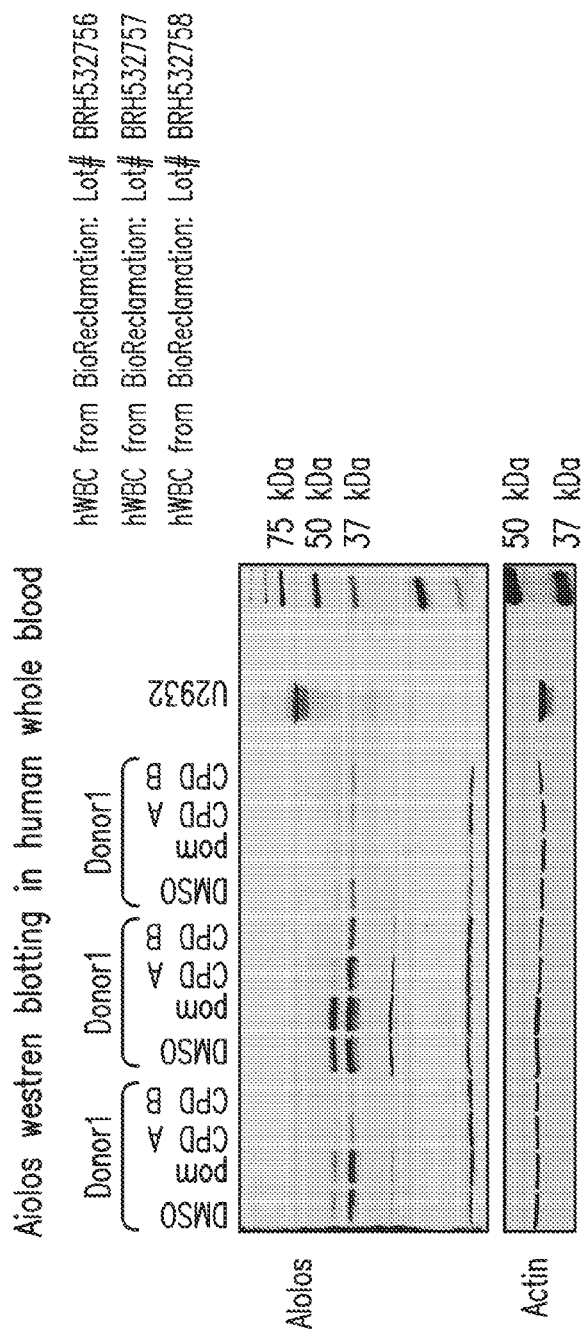
FIG. 4 illustrates Aiolos western blotting in human whole blood samples treated with Compound A or Compound B.
Figure 5:
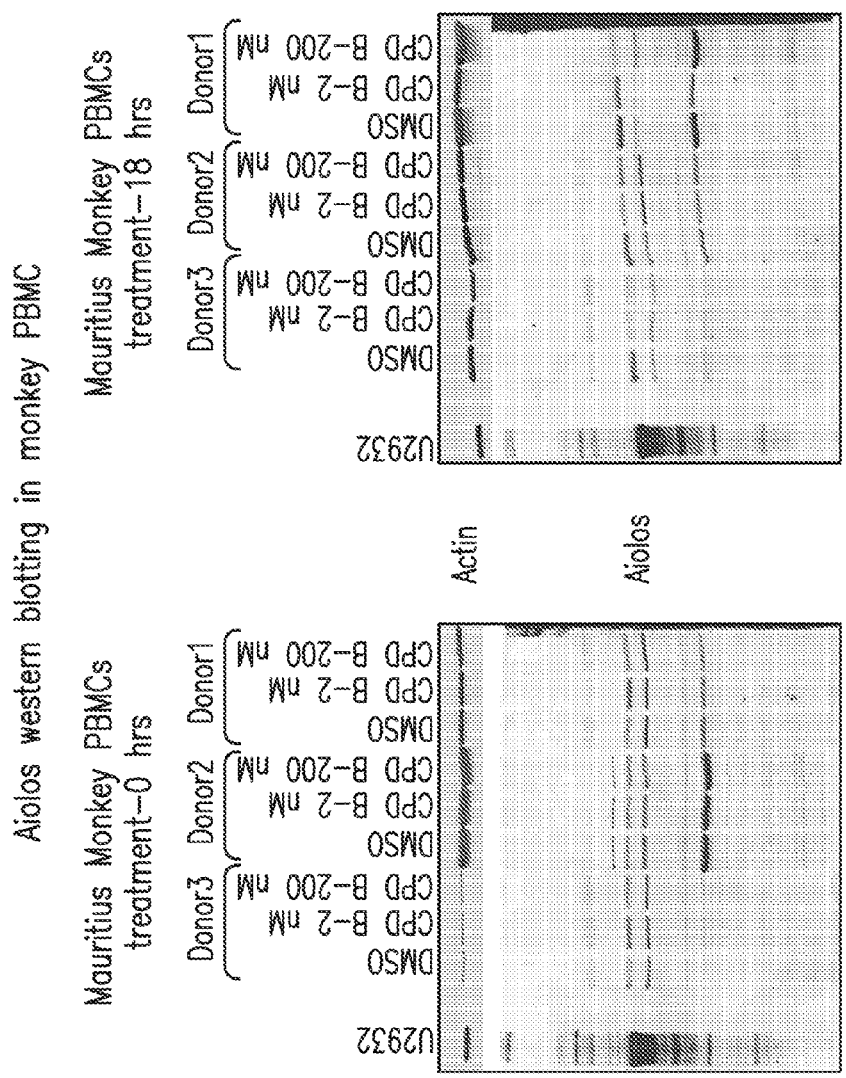
FIG. 5 illustrates Aiolos western blotting in human monkey PMBC treated with Compound B.
Figure 6:
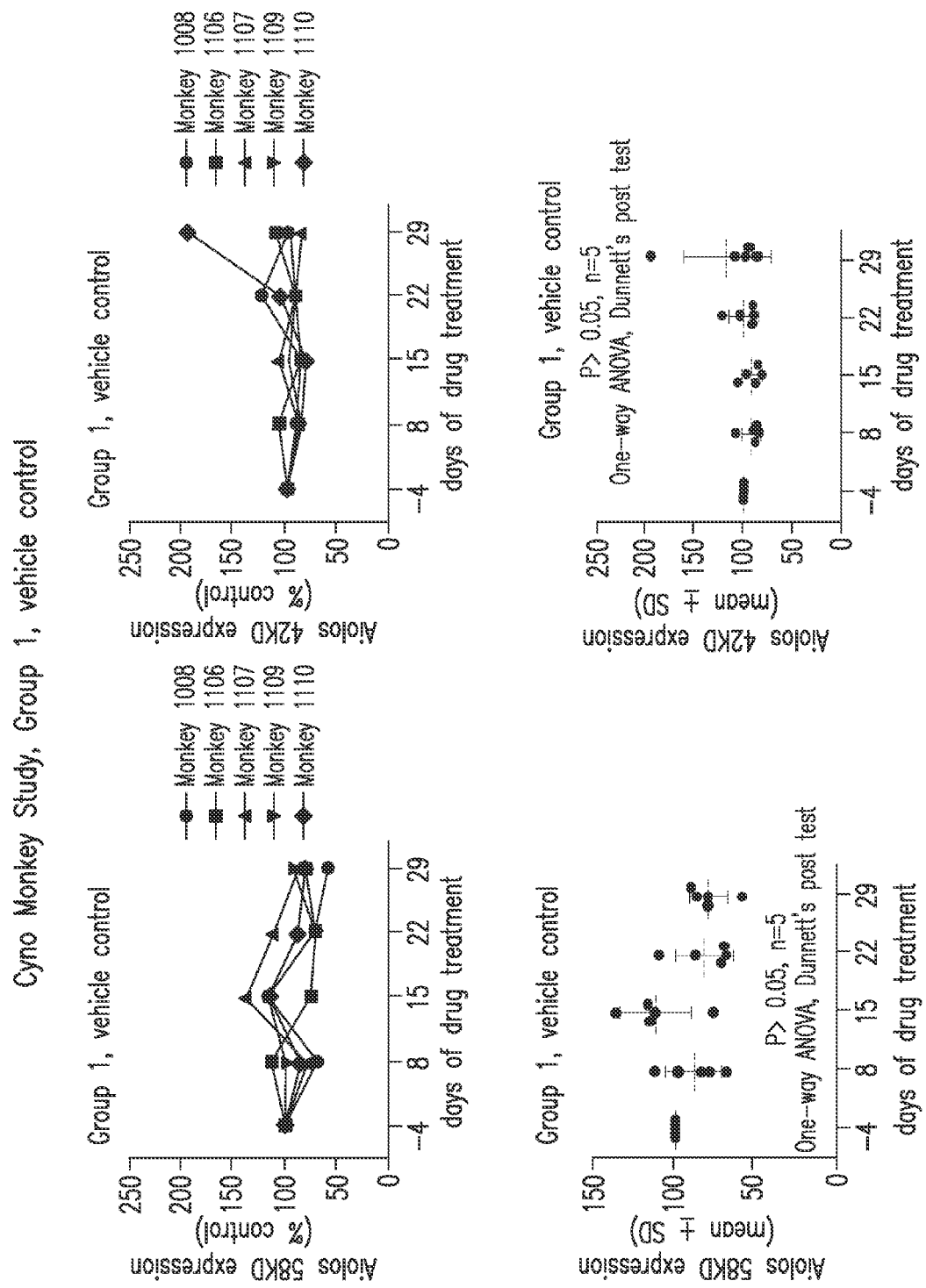
FIGS. 6-9 illustrate results of Aiolos expression studies in Cyno monkeys using (S)-3-(4-((4-(morpholinomethyl)benzyl)oxy)-1-oxoisoindolin-2-yl)piperidine-2,6-dione.
Figure 7:
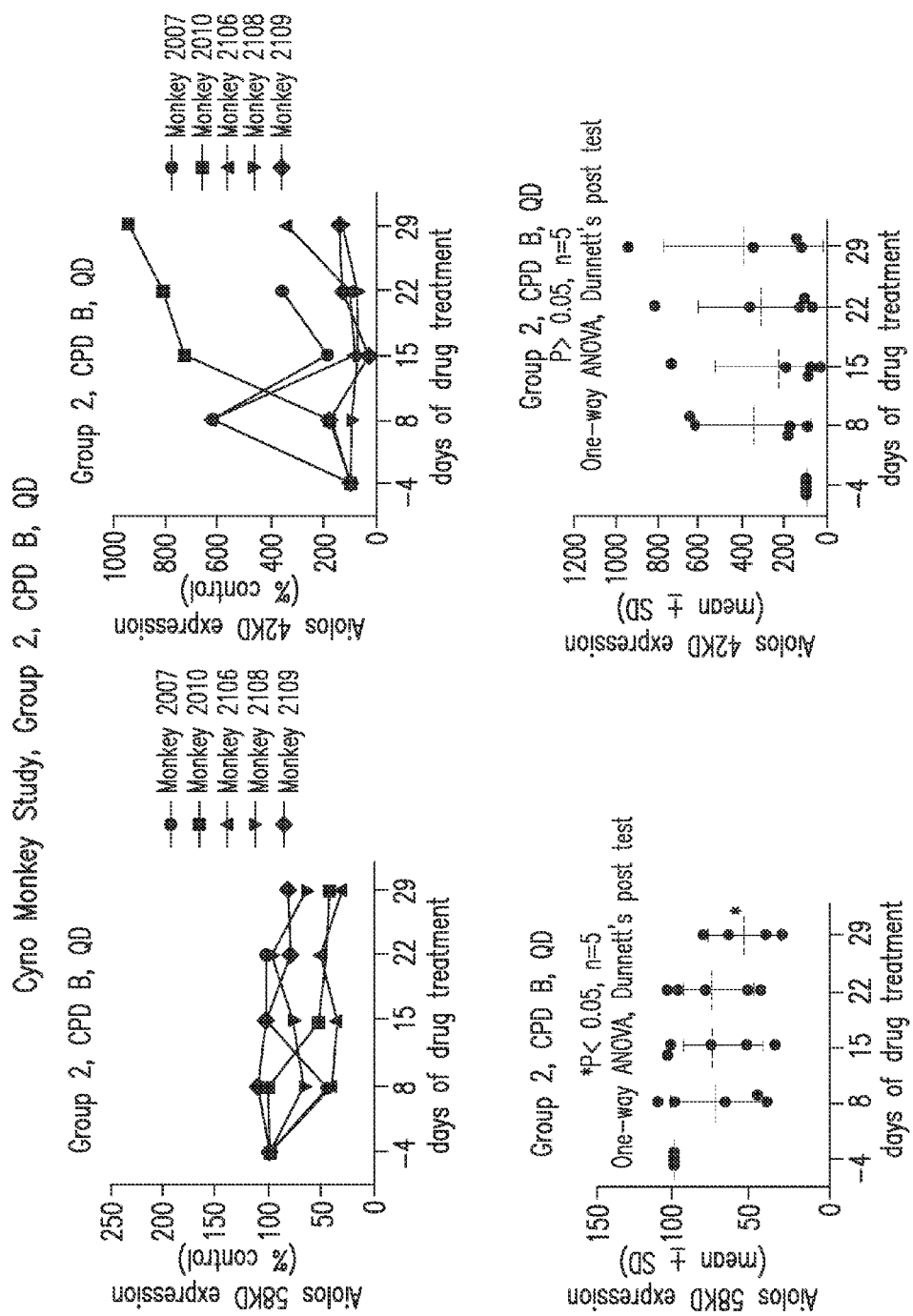
Figure 8:
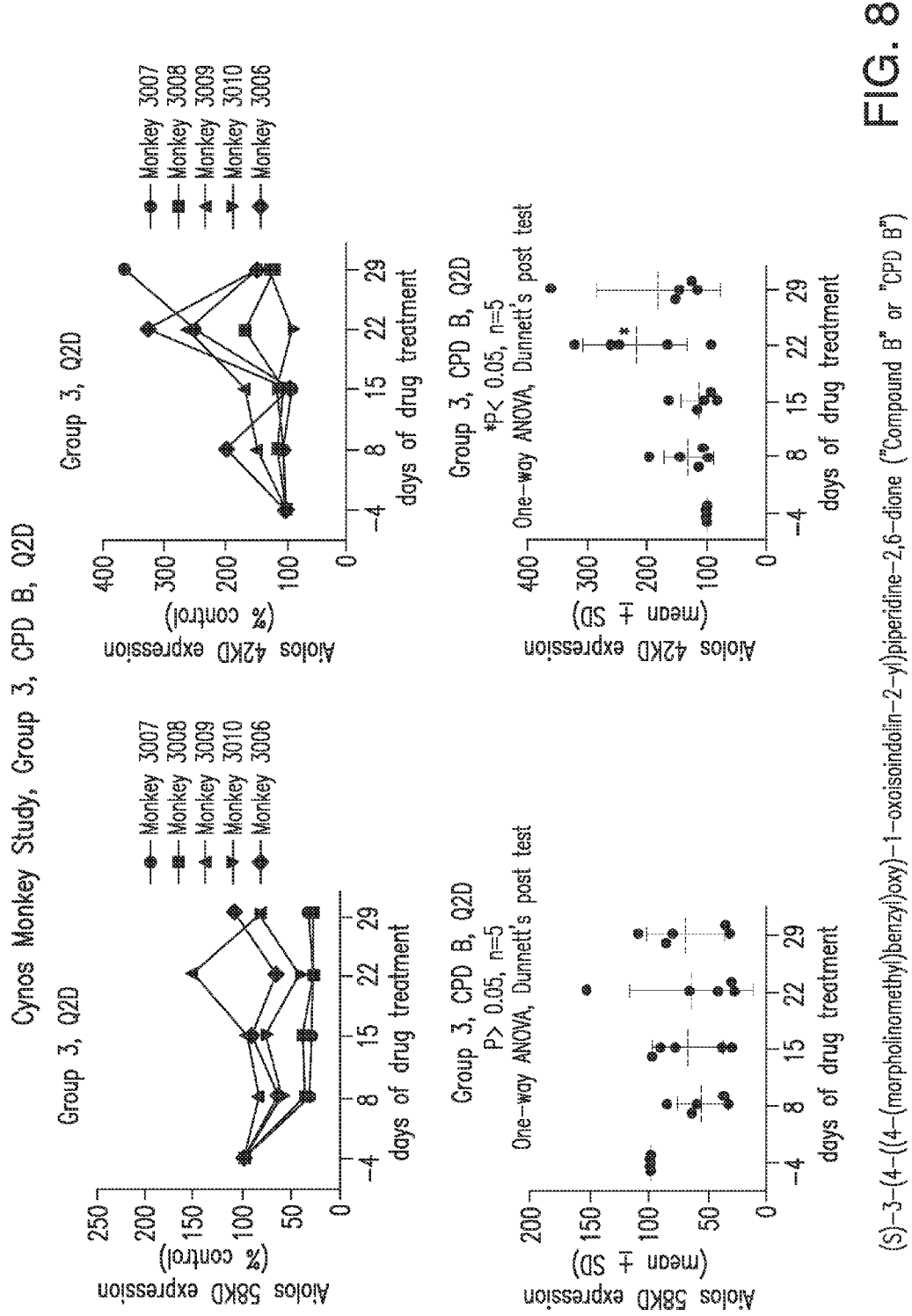
Figure 9:
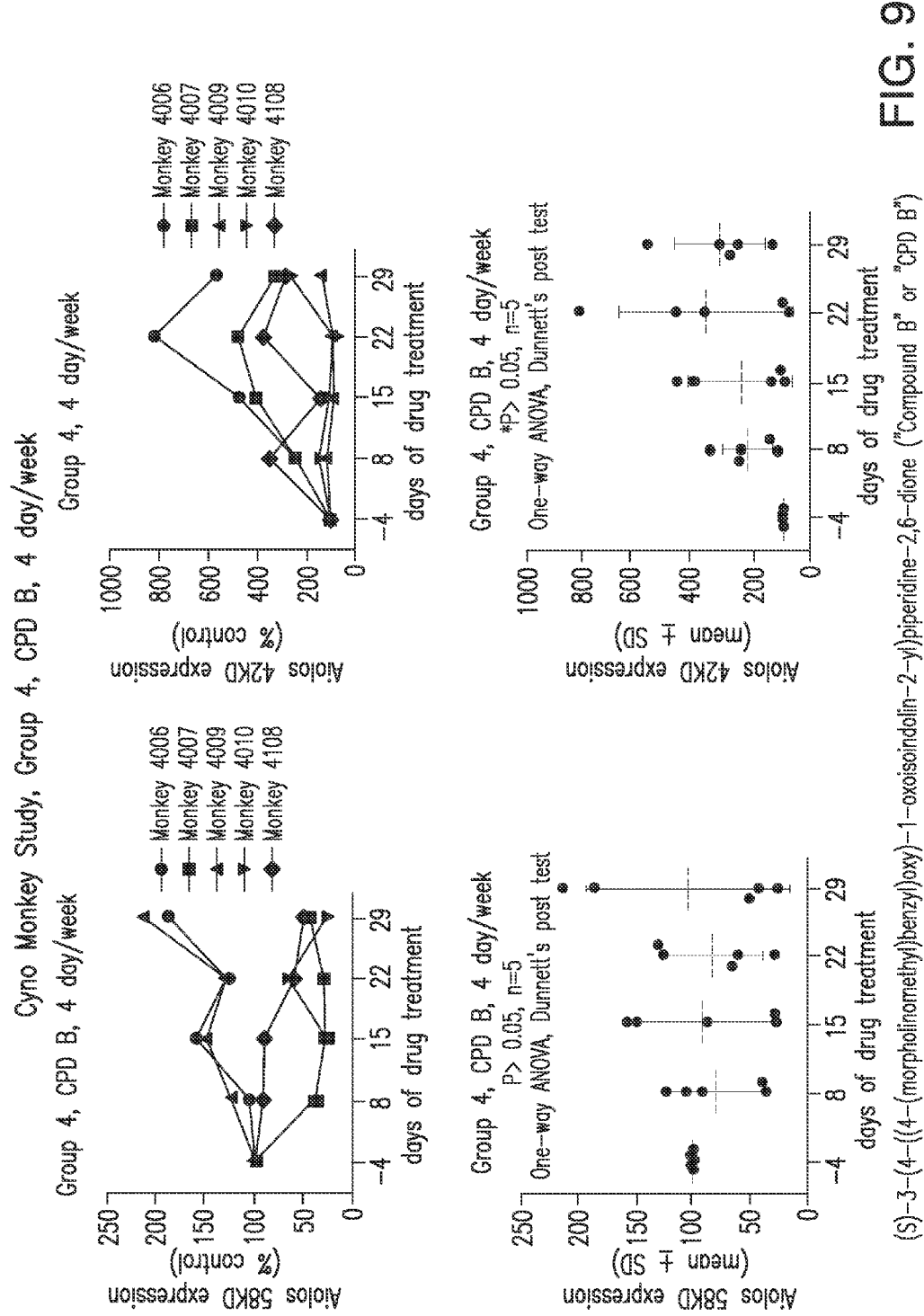

Western blot analysis of human whole blood, treated with the compounds as specified at 250 nM for 18 hours, is shown in FIG. 4, and the same for Mauritius Monkey PMBCs is shown in FIG. 5. (S)-3-(4-((4-(morpholinomethyl)benzyl)oxy)-1-oxoisoindolin-2-yl)piperidine-2,6-dione, at 18 hours after the treatment, inhibited the expression of Aiolos.

Studies on Cyno Monkeys using (S)-3-(4-((4-(morpholinomethyl)benzyl)oxy)-1-oxoisoindolin-2-yl)piperidine-2,6-dione were conducted according to the following treatment regimen.

| Group No. | No. of Males | Test Material | Dose schedule | Dose Level (mg/kg) | Dose Conc. (mg/mL) |
|---|---|---|---|---|---|
| 1 | 5 | vehicle | QD | 0 | 0 |
| 2 | 5 | compound | QD | 0.81 | 0.162 |
| 3 | 5 | compound | every other day | 0.81 | 0.162 |
| 4 | 5 | compound | Days 1-4, 8-11, 15-18 and 22-25 | 0.81 | 0.162 |

Briefly, four treatment groups were assigned, each of which received the treatment by (S)-3-(4-((4-(morpholinomethyl)benzyl)oxy)-1-oxoisoindolin-2-yl)piperidine-2,6-dione according to the dosing schedule and doses specified above. Results are shown in FIGS. 6-9, which show that effects of (S)-3-(4-((4-(morpholinomethyl)benzyl)oxy)-1-oxoisoindolin-2-yl)piperidine-2,6-dione on Aiolos expression may vary according to the dosing regimen, but (S)-3-(4-((4-(morpholinomethyl)benzyl)oxy)-1-oxoisoindolin-2-yl)piperidine-2,6-dione generally inhibits the expression of Aiolos.

Figure 10:
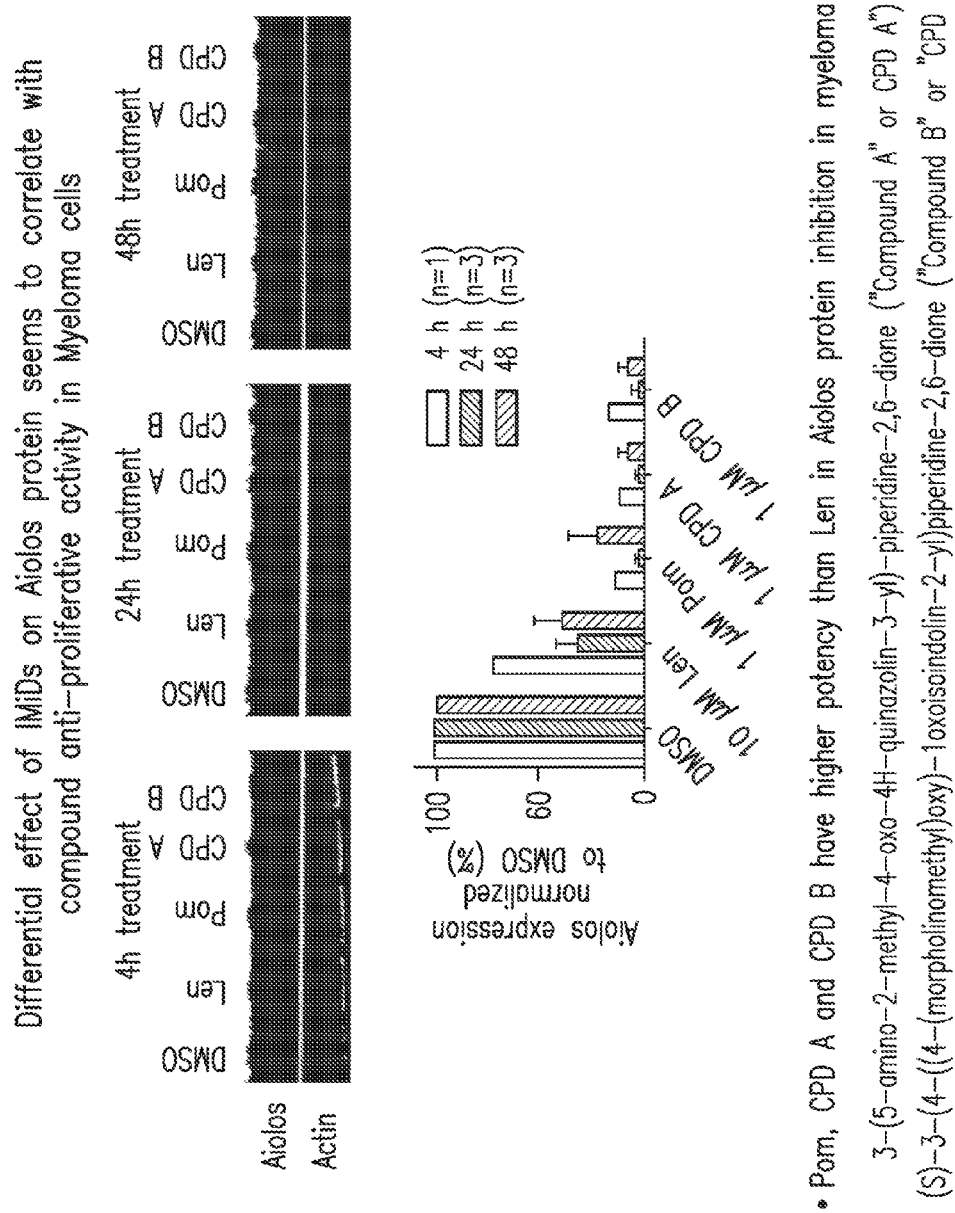
FIG. 10 illustrates the differential effects of Compounds A and B on Aiolos protein in myeloma cells.

The effects of Compound A and (S)-3-(4-((4-(morpholinomethyl)benzyl)oxy)-1-oxoisoindolin-2-yl)piperidine-2,6-dione, lenalidomide ("len") and pomalidomide ("pom") on Aiolos expression were also assessed. Compound A was shown to inhibit the expression of Aiolos in the absence of a proteasome inhibitor at concentrations of 60, 120, 240, 500 and 100 nM, but little inhibition was observed when a proteasome inhibitor was present. As shown in FIG. 10, all of len, pom, Compound A and (S)-3-(4-((4-(morpholinomethyl)benzyl)oxy)-1-oxoisoindolin-2-yl)piperidine-2,6-dione showed inhibitory effect on Aiolos expression. It appeared that the inhibitory effect correlates with compound's anti-proleferative activity in myeloma cells.

Figure 11:
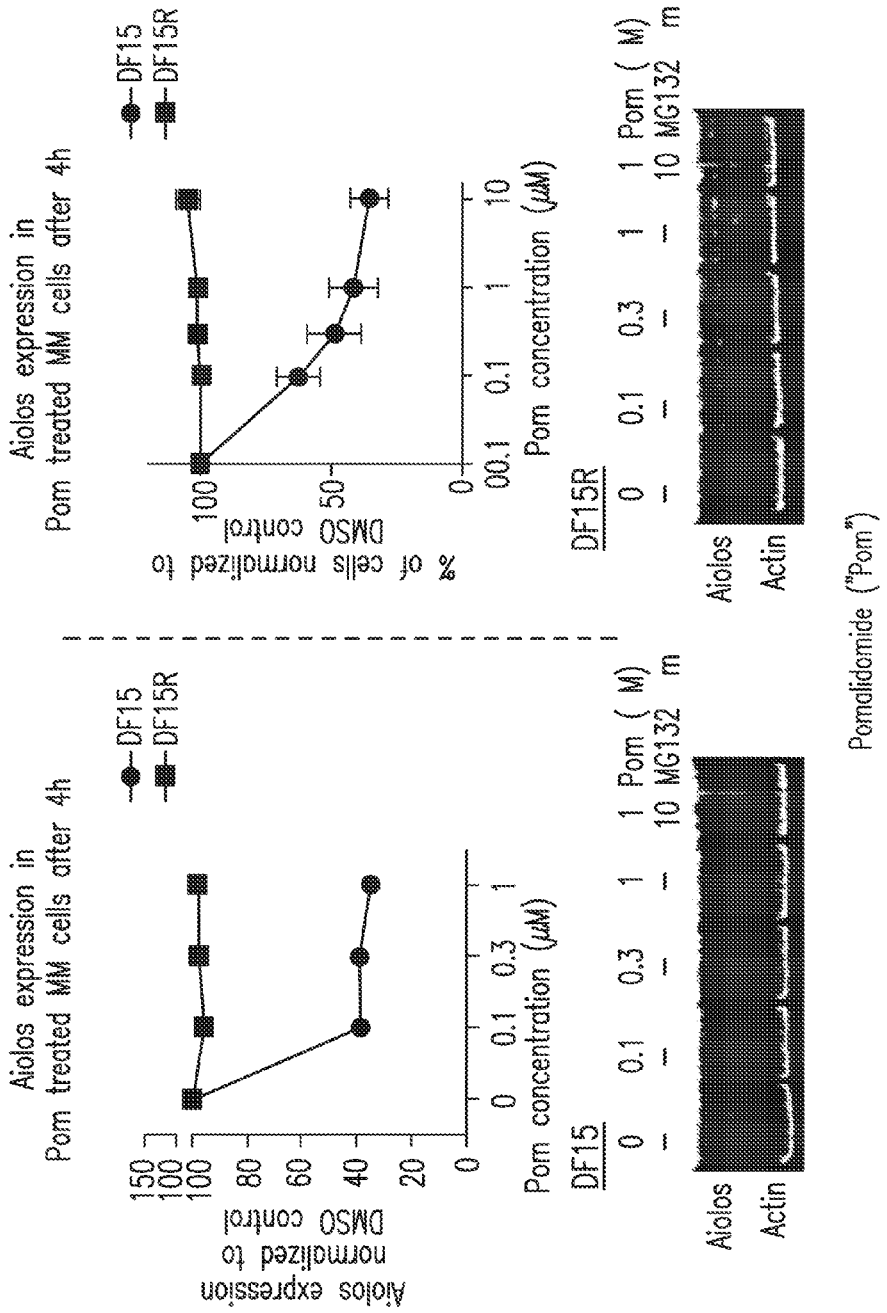
FIG. 11 illustrates dose response curves for pomalidomide treated cells lines with low cereblon (CRBN).
Figure 12:
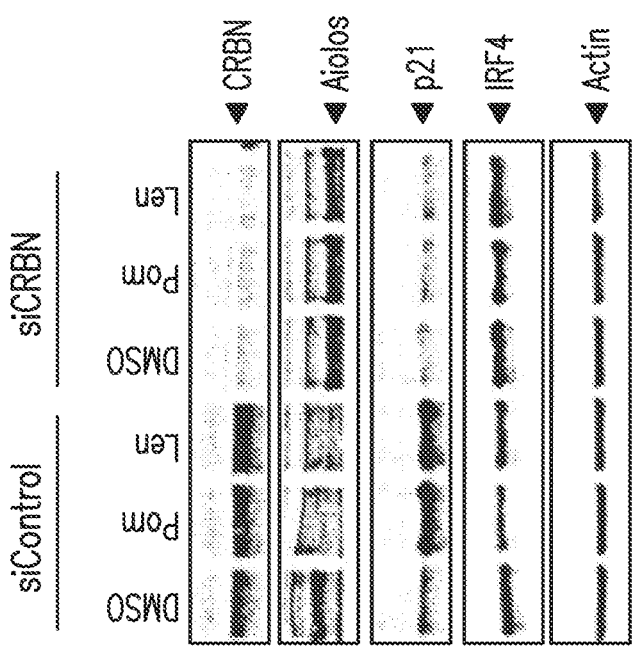
FIG. 12 illustrates that loss of CRBN prevents down-regulation of Aiolos by lenalidomide and pomalidomide.
Figure 13:
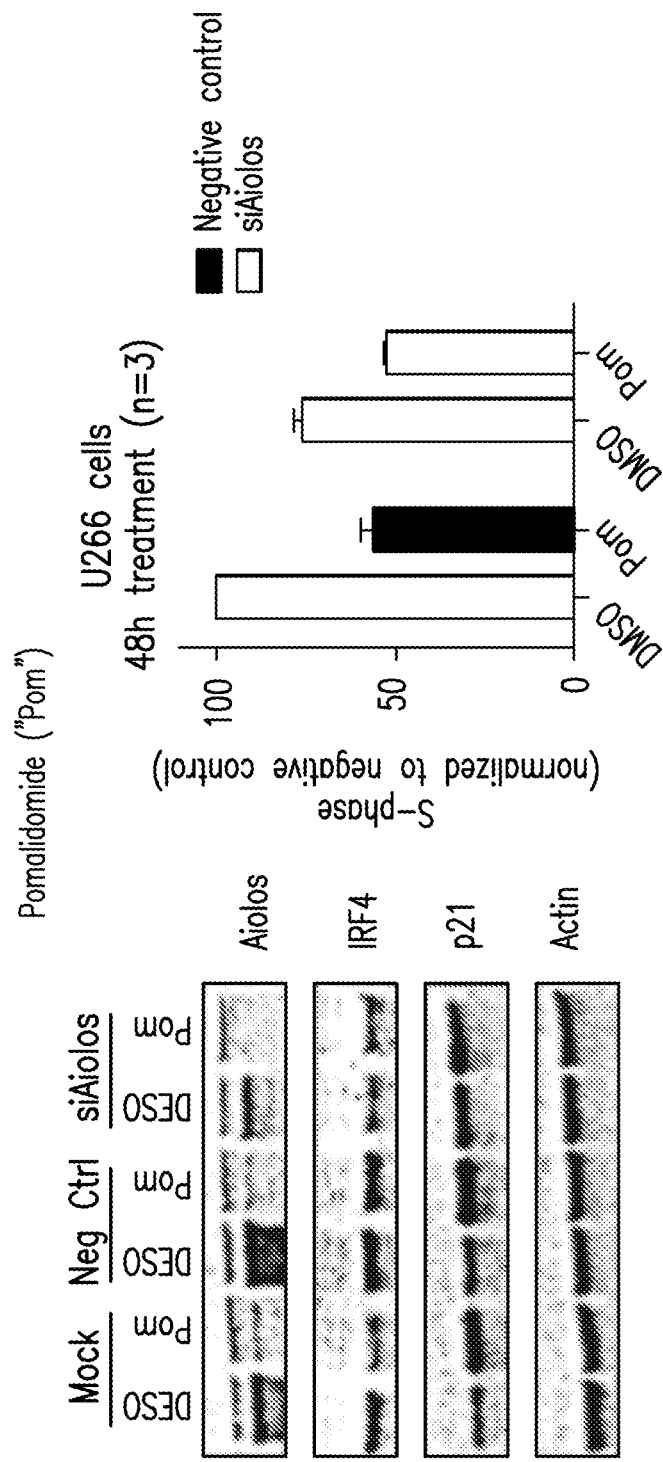
FIG. 13 illustrates that Aiolos knock-down induces p21 expression, decreases IRF4, and decreases number of cells in S phase.
Figure 14:
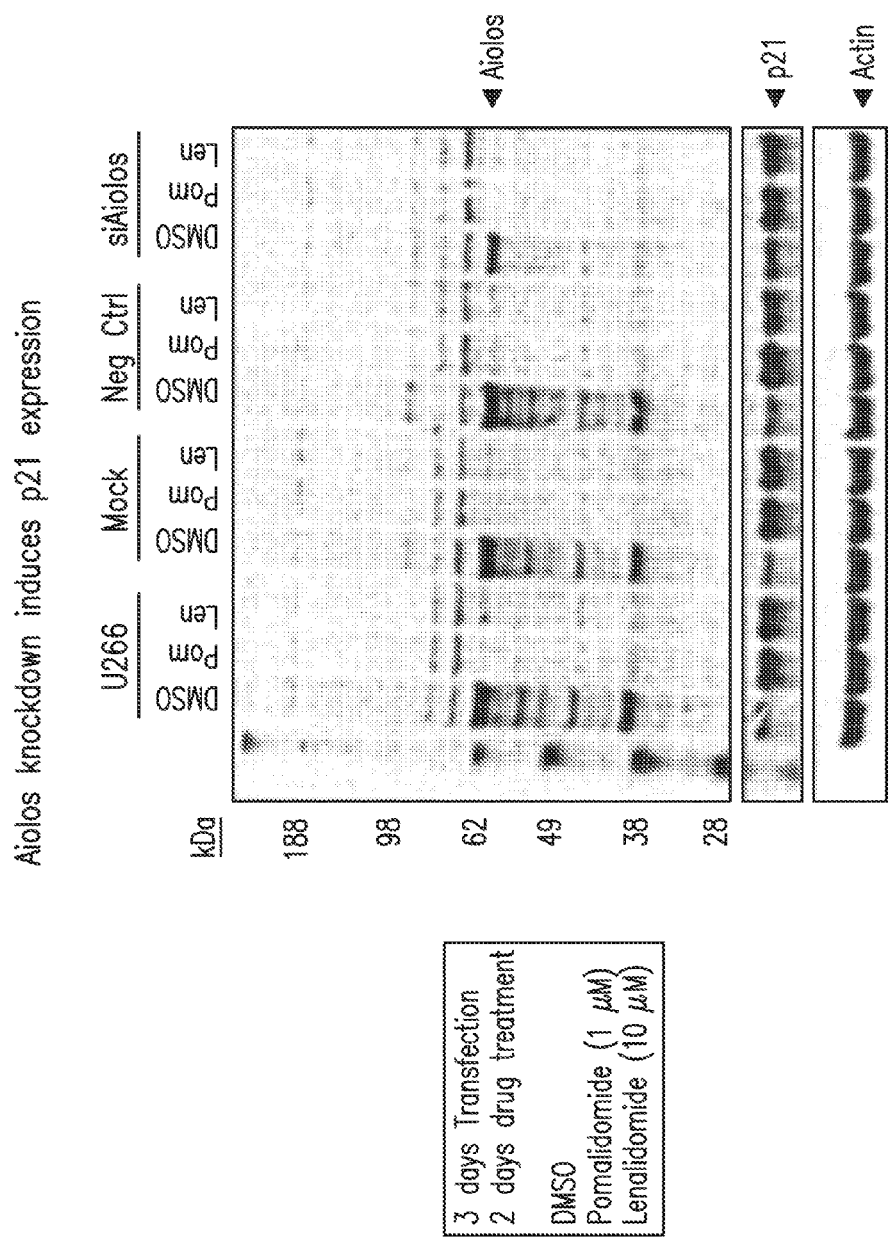
FIG. 14 illustrates that Aiolos knock-down induces p21 expression.

It was shown that little or no inhibition of Aiolos expression occurs in cells with low cereblon expression (FIG. 11) using pomalidomide. Similarly, loss of cereblon was shown to prevent the down-regulation of Aiolos expression with either lenalidomide or pomalidomide (FIG. 12), implying the involvement of cereblon in this process. Finally, it was shown that knock-down of Aiolos induces p21 expression, decreases IRF4, and decreases number of cells in S phase (FIGS. 13 and 14).

6.9.2 Effects of Compound A on Endogenous Aiolos in Breast Cancer Cells

Cell lines (AU565, ZR 75-1, BT-474, EFM-192A, HCC1954, HCC70, MB436 and BT549) were maintained using standard cell culture techniques. For endogenous Aiolos expression, cells were seeded in a 6 well plate at $0.5 \times 10^6$ cells per well in a 3 mL volume of media. Cells were allowed to adhere to the plate overnight. Cells were exposed to 0, 1, and 10 µM Compound A for the specified amounts of time.

In some experiments, cell lines were transfected with an Aiolos overexpression vector using Lipofectamine reagent in a batch method. Cells were seeded in a 12 well plate at $1 \times 10^5$ cells in a 3 mL volume per well. Where specified, cells were pretreated with MG132 at 10 uM for 1 hour, or DMSO was added as a control. Following the pretreatment, Compound A was added directly to the cell culture media at the specified concentration.

Cells were harvested and lysed in Pierce #89900 Ripa buffer containing 2× protease inhibitor cocktail from Pierce #78442. The lysate was applied to a QiaShredder to remove DNA. Total protein yield was measured using BioRad DC protein determination kit (Cat#500-0112). Lysates were stored at −80° C. until use. Samples were applied to BioRad Criterion PreCast gels, 10% (Bio-Rad#345-0010) and transferred to Bio-Rad Nitrocellulose/Filter Paper Sandwiches (#162-0233) for western blot analysis.

Figure 15:
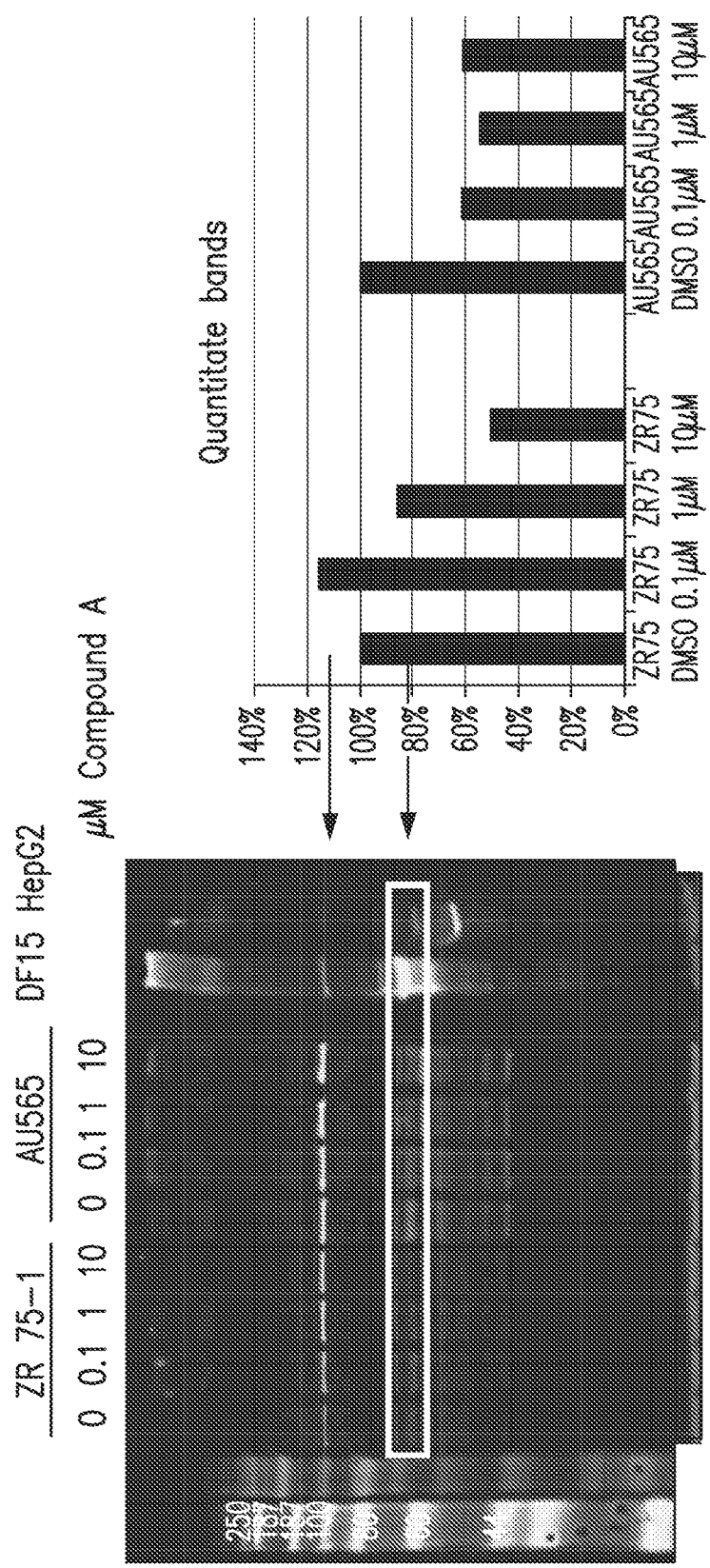
FIG. 15 illustrates the reduction of Aiolos in both ZR 75-1 and AU565 cell lines treated with Compound A.

As shown in FIG. 15, it was found that, at 24 hours after the treatment, Compound A reduced the levels of Aiolos (a band appearing around 60 kD) in both ZR 75-1 and AU565 cell lines. In certain experiments, flag-Aiolos-myc fusion protein was overexpressed in AU565 cells, and the cells were treated with Compound A. In such cases, it was found that western blot analysis using anti-myc antibody provided one Aiolos band around 65 KD, while the same analysis anti-flag antibody provided multiple bands. Further, it was found that the reduction of overexpressed Aiolos begins to show at about 5 hours after the treatment by Compound A, and inhibition of Aiolos by Compound A was rescued by the addition of proteasome inhibitor MG-132. Finally, it was shown that endogenous Aiolos is inhibited by Compound A in Her$^{2+}$ cells (AU565, BT-474, EFM-192A and HCC1954), but not in triple negative cells (HCC70, MB436 and BT549). These results suggest that Aiolos is inhibited by Compound A, and thus, can be used as a biomarker for the treatment by Compound A.

6.9.3 Effects of Compounds on Aiolos and Ikaros Expression

Effects of test compounds (pomalidomide, lenalidomide, Compound A and (S)-3-(4-((4-(morpholinomethyl)benzyl)oxy)-1-oxoisoindolin-2-yl)piperidine-2,6-dione) on expression of Aiolos and Ikaros expression were assessed by western blot analysis at 6 hours after the treatment by the compounds, using procedures similar to those use in connection with western blotting described above. It was shown that the test compounds, to varying degrees, inhibited the expression of both Aiolos and Ikaros. See FIG. 15.

6.10 Justification for Tumor Type Selection in Clinical Studies

There are differences in the in vitro and in vivo activities of Compound A. There is limited direct in vitro activity against tumor cells, while single agent activity was observed in xenografts including U87 (GBM), H929 (MM) and WSU-DLCL2 and DOHH2 (non-Hodgkin's Lymphoma [NHL]). These differences suggest that the activity of Compound A is in part mediated by an effect on the host either through immune modulation and/or anti-angiogenesis and stromal effects.

Compound A partially inhibits NFKB DNA binding activity in DLBCL cells. Compound A HCl will therefore be investigated in tumors where the NFKB pathway has been associated with oncogenesis such as breast cancer (Boehm, J. S.; Zhao, J. J.; Yao J. et al. *Cell* 2007, 129, 1065-1079). Compound A also inhibits HIF1α induction in response to hypoxia, providing a strong biological rationale for its exploration in inflammatory breast cancer (Brito, L. G. O., *Clinical Science* 2011, 66, 1313.). Further justification of tumor type selection may be achieved by signals of activity or data collected from pharmacodynamic (PD) marker analysis in clinical studies. PD marker analysis may include gene signature profiling or protein analysis (eg., NFKB, IRF4) before and after Compound A HCl dosing which may provide a predictive signature of response or changes that are predictive of response.

6.11 Solid Tumor Models

Compound A was evaluated for its effect on solid tumor cell lines from a variety of histologies (e.g., breast, ovarian, colorectal, HCC). Compound A inhibits hypoxia-induced HIF1-α expression in many such solid tumor cell lines. In addition, Compound A inhibits the invasion of solid tumor cells (Table 3) and cell colony formation (Table 4). The inhibition of solid tumor cell colony formation was studied by a single high concentration treatment of Compound A (10 μM) on day 1, followed by monitoring of cell colony formation over the course of 10 to 20 days.

TABLE 3

Effects of Compound A on Invasion of Solid Tumor Cells

| Tumor Cell Type | Cell Line (stimulation) | Invasion (IC$_{50}$) Compound A |
|---|---|---|
| hepatocellular | HepG2 (VEGF) | <0.001 |
|  | SK-HEP-1 (VEGF) | 0.0061 |
| glioblastoma | SNB-19 (PDGF) | 0.16 |
|  | SF-539 (PDGF) | 0.025 |
|  | U251 (PDGF) | 3.7 |
|  | SF-295 (PDGF) | 0.24 |
|  | U87 (PDGF) | 0.08 |
| colorectal | HCT15 (bFGF) | 0.0072 |

TABLE 4

Effects of Compound A in Solid Tumor Cell Colony Formation

| Tumor Cell Type | Cell Line | % Inhibition of Colony Formation[a] |
|---|---|---|
| hepatocellular | HCT15 | 3 |
|  | HCT116 | 13** |
|  | Colo-205 | 17** |
| ovarian | OVCAR-3 | 18* |
| HCC | SK-HEP-1 | 6 |
|  | HEP-G2 | 6.9 |
| glioblastoma | SF268 | 0.6 |
|  | SF295 | 12.9 |
|  | U251 | −6 |
|  | U87 | 2 |
| breast | MDA-MB-453 | −7 |
|  | MCF-7 | 1.4 |
|  | ZR-75-1 | 90** |
| prostate | PC-3 | 14.8 |

[a]10 μM of Compound A.
*p < 0.5;
**p < 0.001 (versus DMSO).

6.12 Dosage Study

Figure 16:
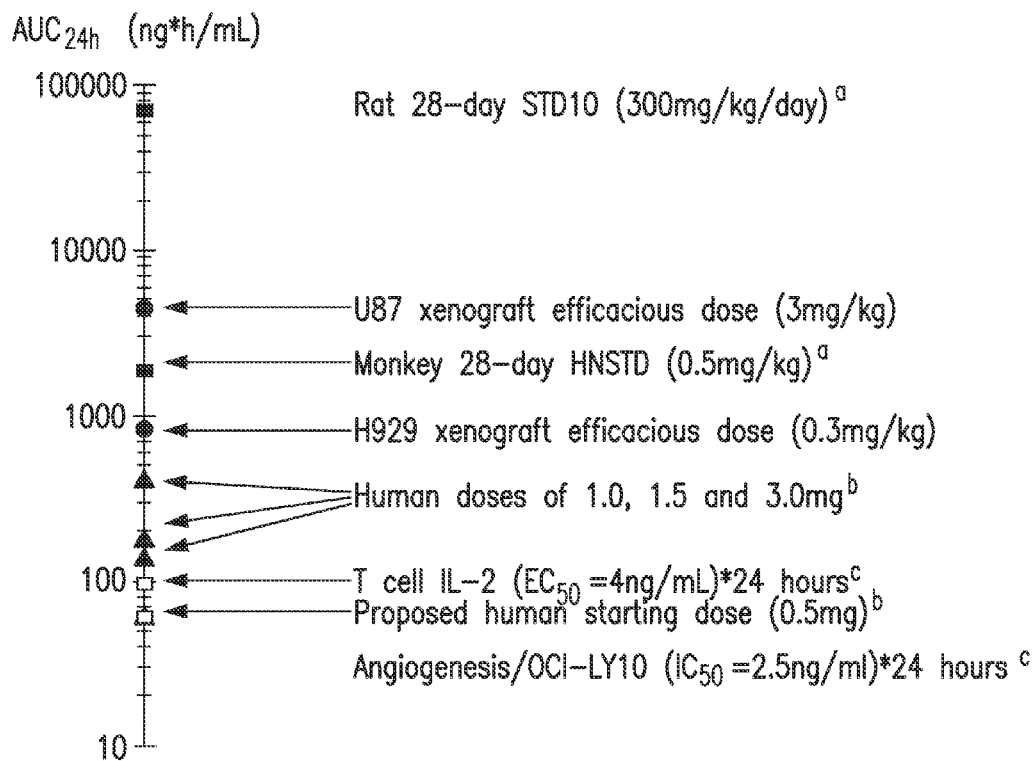
FIG. 16 illustrates comparison of Area Under Curve (AUC) values for rat Severly Toxic Dose at 10% (STD10), Monkey Highest Non-Severly Toxic Dose (HNSTD), and Efficacious Doses from in vivo Pharmacology Studies; Projected AUC Values Using in vitro Pharmacology Models; and Predicted Human AUC Values.

Based on the exposures at which the principal treatment-related effects occurred (Table 5) in the GLP 28-day rat and monkey studies, the cynomolgus monkey is considered more sensitive to the toxicities associated with administration of Compound A. Therefore, the HNSTD in monkeys (0.5 mg base/kg/day or 6 mg/m$^2$) is considered the appropriate dose for use in estimating a starting dose in the initial clinical study with Compound A HCl. Based on the HNSTD and the ICH S9 recommended 6-fold margin in oncology patients, a starting human dose could be as high as 1.7 mg base (Table 5). However, based upon pharmacology models and in vitro potency of Compound A, a starting dose of 0.5 mg Compound A HCl (0.44 mg free base equivalent) is proposed with a resulting predicted exposure margin of 30-fold. See FIG. 16.

TABLE 5

Clinical Starting Doses Based on Rat STD10 and Monkey HNSTD from 28-Day Toxicity Studies

| Species | Animal Dose | HED (mg/kg)[a] | HED (mg/person)[b] | Safety Factor[c] | Starting Dose (mg) |
|---|---|---|---|---|---|
| Rat STD10 | 300 mg base/kg/day | 48 mg base/kg | 2900 mg base/person | 10 | 290 mg base |
| Monkey HNSTD | 0.5 mg base/kg/day | 0.16 mg base/kg | 10 mg base/person | 6 | 1.7 mg base |

HNSTD = highest non-severely toxic dose; HED = human equivalent dose; STD10 = severely toxic dose in 10% of the animals.
[a]Conversion factors from the July 2005 FDA Guidance for Industry entitled, "Estimating the Maximum Safe Starting Dose in Initial Clinical Trials for Therapeutics in Adult Healthy Volunteers."
[b]The dose/person was calculated based on a 60-kg human body weight.
[c]Based on the October 2009 ICH Harmonized Tripartite Guideline: "S9 Nonclinical Evaluation for Anticancer Pharmaceuticals," a starting dose for first administration in humans should be either one-tenth the STD10 in rodents, or one-sixth of the HNSTD if the non-rodent is the most appropriate species.

Using derived plasma clearance and volume of distribution values based on allometric scaling and assuming 82% oral bioavailability in humans, the predicted C$_{max}$ and area under the curve from 0 to 24 hr (AUC$_{24hr}$) at the intended human starting dose of 0.5 mg Compound A HCl/day are 5.5 ng/mL and 62 ng·hr/mL, respectively. The systemic exposure (AUC$_{24hr}$) to Compound A HCl at the anticipated human starting dose is approximately 1160-fold lower than the STD10 in rats, and approximately 30-fold lower than that at the HNSTD in monkeys.

The predicted plasma concentrations (C$_{max}$ of 5.5 ng/mL and AUC$_{24hr}$ of 62 ng·hr/mL) at the intended human starting dose (0.5 mg Compound A HCl/day) are in the range of many of the in vitro EC$_{50}$ and IC$_{50}$ values for immune modulation (T cell IL-2 EC$_{50}$=14 nM; 4 ng/mL), anti-proliferation (OCI-LY10 cell line IC$_{50}$=8.5 nM; 2.4 ng/mL), and angiogenesis inhibition (human umbilical artery assay IC$_{50}$=9.4 nM; 2.7 ng/mL).

6.13 Clinical Protocol

A Phase 1a/1b, clinical study to determine the safety, tolerability, pharmacokinetics and efficacy of lenalidomide, pomalidomide, thalidomide, Compound A, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl}-piperidine-2,6-dione and/or other immunomodulatory compounds, or enantiomers or mixtures of enantiomers thereof; or pharmaceutically acceptable salts, solvates, hydrates, co-crystals, clathrates, or polymorphs thereof, and/or other immunomodulatory compounds when administered orally to subjects with IBC is provided. The non-tolerated dose (NTD), the maximum tolerated dose (MTD) and the recommended phase 2 dose (RP2D) are to be defined in the study. The effect of the compound on biomarkers of angiogenesis in pre- and during treatment tumor biopsies will be evaluated.

Study Design

The study is designed as a Phase 1a/1b study consisting of two parts: dose escalation (Part A), and dose expansion (Part B). In Part A, subjects will receive single and multiple ascending doses lenalidomide, pomalidomide, thalidomide, Compound A, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl}-piperidine-2,6-dione, and/or other immunomodulatory compounds to measure pharmacokinetics (PK) and identify the maximum tolerated dose (MTD) and the recommended phase 2 dose (RP2D). A standard dose (3+3) escalation design (Simon et al., 1997) will be used to identify initial toxicity. Initial cohorts of three subjects will be given lenalidomide, pomalidomide, thalidomide, Compound A, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl}-piperidine-2,6-dione, and/or other immunomodulatory compounds (0.5 mg once daily) in dose increments of 100% until the first instance of grade 3 or higher toxicity suspected to be drug-related in the first cycle, at which point the particular cohort will be expanded to a total of six subjects. This standard escalation schedule will be initiated in order to establish the non-tolerated dose (NTD) and MTD. Smaller increments and additional subjects within a dose cohort may also be evaluated for safety. Approximately 20 to 40 subjects will be treated and evaluated in Part A; however, the total number of subjects in Part A depends on the number of dose cohorts needed to establish the MTD. A dose will be considered the NTD when 2 or more out of 6 evaluable subjects in a cohort experience drug-related dose limiting toxicity (DLT) during Cycle 1. When the NTD is established, dose escalation will stop. The MTD is defined as the last dose level below the NTD with 0 or 1 out of 6 evaluable subjects experiencing DLT during Cycle 1. An intermediate dose (i.e., one between the NTD and the last dose level before the NTD) or additional subjects within any dose cohort may be required to more precisely determine the MTD and RP2D.

In Part B, subjects may start dosing at the MTD and/or a lower dose level based on safety, PK and/or PD data from Part A. Approximately 100 subjects (up to 20 per cohort), stratified by tumor type, will be treated and evaluated for safety and antitumor activity after every two cycles of therapy. The dose, doses, or schedule appropriate will also be determined. During Part B, safety data will be reviewed regularly regarding the study continuation, as appropriate.

Study Population

Women, 18 years or older, with breast cancer, including subjects who have progressed on (or not been able to tolerate) standard therapy or for whom no standard anticancer therapy exists.

Dosing and Length of Study

During the first cycle, only in Part A, each subject will be administered a single daily dose of lenalidomide, pomalidomide, thalidomide, Compound A, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl}-piperidine-2,6-dione, and/or other immunomodulatory compounds on Day 1 followed by a 48-hour observation and PK sampling period, followed on Day 1 by daily uninterrupted dosing for 28 days (Cycle 1=30 days). In subsequent Part A cycles, subjects are treated in 28-day cycles with continuous dosing from Day 1 to 28. The compounds lenalidomide, pomalidomide, thalidomide, Compound A, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl}-piperidine-2,6-dione, and/or other immunomodulatory compounds will be given once or twice a day at a dose of 0.1, 0.5, 1, 2, 4, 5, 7.5, 10, 20, 25, or 50 mg in an initial dose. The dose may be of 0.1, 0.5, 1, 2, 4, 5, 7.5, 10 mg given once a day. The dose may be 50, 25, or 10 mg given twice a day. The dose may be adjusted up, or down, from the starting dose during treatment. As described above, if needed, the drug may be given in a cyclical manner.

In Part B, subjects receive continuous dosing for 28 days from the beginning—there is no post initial, single dose 48-hour PK collection period.

Therapy will be discontinued if there is evidence of disease progression, unacceptable toxicity or subject/physician decision to stop. Subjects may continue to receive compound without interruption for as long as they derive benefit as judged by the Investigator.

Enrollment is expected to occur over approximately 24 months. Completion of active treatment and subject follow-up is expected to take an additional 3-6 months Study Treatments Celgene Corporation will supply the compounds, including, for example, lenalidomide, pomalidomide, thalidomide, Compound A, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl}-piperidine-2,6-dione, and/or other immunomodulatory compounds as 0.1 mg, 0.5 mg, 1 mg and 3 mg capsules for oral administration. The compound will be packaged in bottles inside boxes containing drug for 28 days.

In Part A (the dose escalation phase), the dose level will start at 0.5 mg once daily after the single PK dose. After the first dose is administered to the last subject in any cohort, subjects are observed for at least 30 days before the next higher, protocol-specified dose cohort can begin. Intra subject dose escalation is not permitted unless approved by the Safety Review Committee (SRC) which will consist of the principal investigator and Celgene's medical monitor.

In Part B, subjects may receive lenalidomide, pomalidomide, thalidomide, Compound A, 3-(4-((4-(morpholinomethyl)benzyl)oxy)-1-oxoisoindolin-2-yl)piperidine-2,6-dione, (S)-3-(4-((4-(morpholinomethyl)benzyl)oxy)-1-oxoisoindolin-2-yl)piperidine-2,6-dione, 3-(1-oxo-4-(4-(2-(pyrrolidin-1-yl)ethoxy)benzyloxy)isoindolin-2-yl)-piperidine-2,6-dione, 3-(4-(4-(2-morpholin-4-yl-ethoxy)-benzyloxy)-1-oxoisoindolin-2-yl)-piperidine-2,6-dione, 3-(4-(4-(2-morpholin-4-yl-ethyl)-benzyloxy)-1-oxo-1,3-dihydro-isoindol-2-yl}-piperidine-2,6-dione, and/or other immunomodulatory compounds at the MTD and/or a lower dose level, based on safety, PK and PD evaluations from Part A. Approximately 100 subjects (preselected tumor types in groups of up to 20) will be evaluated for safety and antitumor effects.

Overview of Efficacy Assessments

Subjects will be evaluated for efficacy after every 2 cycles. The primary efficacy variable is response. Tumor response will be based on Response Evaluation Criteria in Solid Tumors (RECIST 1.1), Responses Assessment for Neuro-Oncology (RANO) Working Group for GBM.

Secondary/exploratory endpoints include biomarker measurements in blood and tumor, histopathologic response and correlations with pharmacogenomic findings. Supplementary efficacy variables (e.g., ECOG performance status, PET outcomes) will also be examined; in addition, hypovascularization changes will be measured by volume transfer constant (Ktrans) and initial AUC (IAUC) using DCE-MRIs.

Overview of Safety Assessments

The safety variables for this study are adverse events, clinical laboratory variables, 12-lead ECGs (centrally reviewed), LVEF assessments, physical examinations and vital signs.

Overview of Pharmacokinetic Assessments

The PK profiles of the compounds provided herein and their metabolites will be determined from serial blood and urine collections during the first treatment cycle. These will be correlated with pharmacodynamic (PD) outcomes where possible.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating or managing locally advanced breast cancer comprising administering to a patient in need of such treatment or management a therapeutically effective amount of 3-(5-amino-2-methyl-4-oxo-4H-quinazolin-3-yl)-piperidine-2,6-dione, or an enantiomer or mixture of enantiomers thereof; or a pharmaceutically acceptable salt, co-crystal, or clathrate thereof.

2. The method of claim 1, wherein the locally advanced breast cancer is inflammatory breast cancer.

3. The method of claim 1, wherein the cancer is relapsed or refractory.

4. The method of claim 1, wherein the cancer is drug-resistant.

5. The method of claim 1, wherein the compound is 3-(5-amino-2-methyl-4-oxo-4H-quinazolin-3-yl)-piperidine-2,6-dione, or a salt thereof.

6. The method of claim 1, further comprising the administration of a therapeutically effective amount of one or more additional active agents.

7. The method of claim 6, wherein the additional active agent is selected from the group consisting of paclitaxel, docetaxel, protein-bound paclitaxel, 5-azacytidine, capecitabine, gemcitabine, romidepsin, vorinostat, panobinostat, valproic acid, belinostat, etinostat, trastuzumab, trastuzumab emtansine, lapatinib, bevacizumab, pertuzumab, doxorubicin, daunorubicin, mitoxantrone, amsacrine, aurintricarboxylic acid, irinotecan, topotecan, camtothecin, lamellarin D, etoposide, teniposide, tamoxifen, cisplatin, carboplatin, oxaliplatin, vinblastine, vincristine, vindesine, vinorelbine, navitoclax, a Bcl-2 inhibitor, and PI3K/AKT/mTOR pathway inhibitor.

8. The method of claim 1, wherein the compound, or a pharmaceutically acceptable salt thereof, is administered in an amount of from about 0.5 to about 50 mg per day.

9. The method of claim 8, wherein the compound, or a pharmaceutically acceptable salt thereof, is administered in an amount of about 0.5 to about 5 mg per day.

10. The method of claim 8, wherein the compound, or a pharmaceutically acceptable salt thereof, is administered in an amount of about 0.5, 1, 2, 4, 5, 10, 15, 20, 25 or 50 mg per day.

11. The method of claim 8, wherein the compound, or a pharmaceutically acceptable salt thereof, is orally administered.

12. The method of claim 8, wherein the compound, or a pharmaceutically acceptable salt thereof, is administered in a capsule or tablet.

13. The method of claim 8, wherein the compound is administered in 10 mg or 25 mg of a capsule.

14. The method of claim 1, wherein the compound is administered for 21 days followed by seven days rest in a 28 day cycle.

15. A method for treating or managing locally advanced breast cancer, comprising:
   (i) identifying a patient having locally advanced breast cancer sensitive to treatment with 3-(5-amino-2-methyl-4-oxo-4H-quinazolin-3-yl)-piperidine-2,6-dione, or an enantiomer or mixture of enantiomers thereof; or a pharmaceutically acceptable salt co-crystal, or clathrate thereof; and
   (ii) administering to the patient a therapeutically effective amount the compound selected in step (i).

16. The method of claim 15, wherein the locally advanced breast cancer is inflammatory breast cancer.

17. The method of claim 15, wherein identifying a patient having locally advanced breast cancer sensitive to treatment comprises detecting the level of expression of CRBN, Aiolos (IKZF3) or Ikaros (IKZF1) expression within the cancer.

* * * * *